United States Patent
Zhou et al.

(10) Patent No.: US 12,226,414 B2
(45) Date of Patent: Feb. 18, 2025

(54) 1-ISOPROPYL-3-METHYL-8-(PYRIDIN-3-YL)-1,3-DIHYDRO-2H-IMIDAZO[4,5-C] CINNOLIN-2-ONE AS SELECTIVE MODULATORS OF ATAXIA TELANGIECTASIA MUTATED (ATM) KINASE AND USES THEREOF

(71) Applicant: SUZHOU ZANRONG PHARMA LIMITED, Suzhou (CN)

(72) Inventors: Ding Zhou, Shanghai (CN); Ziqiang Cheng, Shanghai (CN)

(73) Assignee: SUZHOU ZANRONG PHARMA LIMITED, Suzhou (CN)

( * ) Notice: Subject to any disclaimer, the term of this patent is extended or adjusted under 35 U.S.C. 154(b) by 1017 days.

(21) Appl. No.: 17/274,781

(22) PCT Filed: Sep. 16, 2019

(86) PCT No.: PCT/CN2019/105951
§ 371 (c)(1),
(2) Date: Mar. 9, 2021

(87) PCT Pub. No.: WO2020/052688
PCT Pub. Date: Mar. 19, 2020

(65) Prior Publication Data
US 2022/0047595 A1 Feb. 17, 2022

(30) Foreign Application Priority Data

Sep. 14, 2018 (WO) ................ PCT/CN2018/105675

(51) Int. Cl.
*A61K 31/5025* (2006.01)
*A61K 31/5377* (2006.01)
*C07D 487/04* (2006.01)

(52) U.S. Cl.
CPC ...... *A61K 31/5025* (2013.01); *A61K 31/5377* (2013.01); *C07D 487/04* (2013.01)

(58) Field of Classification Search
None
See application file for complete search history.

(56) References Cited

FOREIGN PATENT DOCUMENTS

| CN | 106255692 A | 12/2016 |
| WO | 2017162605 A1 | 9/2017 |
| WO | WO-2019057757 A1 * | 3/2019 ........... A61K 31/175 |

OTHER PUBLICATIONS

Pike, Kurt G. et al., "The Identification of Potent, Selective, and Orally Available Inhibitors of Ataxia Telangiectasia Mutated (ATM) Kinase: The Discovery of AZD0156 (8-{6-[3-(Dimethylamino)propoxy]pyridin-3-yl}-3-methyl-1-(tetrahydro-2H-pyran-4-yl)-1,3-dihydro-2H-imidazo[4,5-c]quinolin-2-one)", Journal of Medicinal Chemistry, vol. 9, No. 61, Apr. 23, 2018 (Apr. 23, 2018), ISSN:0022-2623, p. 3823-3841.
International Search Report and Written Opinion of PCT/CN2019/105951, mailed on Dec. 20, 2019.

* cited by examiner

*Primary Examiner* — Gigi G Huang
(74) *Attorney, Agent, or Firm* — James J. Zhu; Jun He Law Offices P.C

(57) ABSTRACT

The present application relates to novel substituted imidazo [4,5-c]cinnolin-2-one compounds and pharmaceutically acceptable salts thereof, which selectively modulate ataxia telangiectasia mutated ("ATM") kinase. The present application also relates to pharmaceutical compositions comprising one or more of the compounds and salts thereof as an active ingredient, and to the use of the compounds and salts thereof in the treatment of ATM-associated diseases or conditions, including cancers.

16 Claims, No Drawings

1-ISOPROPYL-3-METHYL-8-(PYRIDIN-3-YL)-1,3-DIHYDRO-2H-IMIDAZO[4,5-C] CINNOLIN-2-ONE AS SELECTIVE MODULATORS OF ATAXIA TELANGIECTASIA MUTATED (ATM) KINASE AND USES THEREOF

FIELD OF THE DISCLOSURE

The present application relates to novel substituted imidazo[4,5-c]cinnolin-2-one compounds and pharmaceutically acceptable salts thereof, which selectively modulate ataxia telangiectasia mutated ("ATM") kinase. The present application also relates to pharmaceutical compositions comprising one or more of the compounds and salts thereof as an active ingredient, and to the use of the compounds and salts thereof in the treatment of ATM-associated diseases or conditions, including cancers.

BACKGROUND OF THE DISCLOSURE

ATM kinase, a serine/threonine kinase, is named after the autosomal recessive disorder ataxia-telangiectasia (A-T) (Paul, T. T, *Annu Rev Biochem* 2015, 711-38). ATM plays a central role in the repair of DNA double-strand breaks (DSB), which is very cytotoxic if not timely repaired. DSBs can be repaired by two major pathways: Non-Homologous End Joining (NHEJ) or Homologous Recombination (HR). NHEJ operates throughout the cell cycle, directly resealing the two broken ends with minimal processing. In contrast, HR takes place during the S and G2 phases of the cell cycle and necessitates extensive end processing (or resection). This generates single-stranded DNA that invades the homologous copy of the broken locus which is then used as a template for DNA synthesis (Clouaire, T. et al, *DNA Repair (Amst)* 2017, 84-91). In comparison, NHEJ is a fast process but error prone; whereas HR is a slower process than NHEJ, but error free. ATM fixes DSBs through HR.

Following DNA DSBs, ATM is recruited by the MRE11-RAD50-NBS1 (MRN) complex which senses and initiates DNA repair. As ATM is brought to the site of DNA damage, it dissociates from inactive homodimers into active monomers and is catalytically activated by autophosphorylation at Ser1981 and other sites, as well as acetylation at Lys3016. ATM then binds to the C terminus of NBS1, a component of the MRN complex, and serves as a transducer and phosphorylates and activates other protein kinases, for example the histone H2A.X (γH2A.X).

ATM is activated by DSBs which can be induced by ionizing radiation, chemotherapy drugs and PARP inhibition. Topoisomerase-I inhibitor (such as irinotecan, topotecan) and PARP inhibitor (such as Olaparib) cause single strand DNA breaks which are converted to DSBs during replication (Choi M. et al, *Mol Cancer Ther,* 2016, 1781-91). Other anti-cancer treatments such as ionizing radiation (IR), Platinum drugs (Cisplatin), topoisomerase-II inhibitors (doxorubicin, etoposide) directly induces DSBs. Combination of ATM inhibitor with chemotherapy, radiation and PARP inhibitors make cancer cells nearly impossible to repair DSBs which are very cytotoxic. Given the crucial role of ATM played during DSBs, ATM kinase inhibitors are expected to synergize with PARP or Topoisomerase inhibitors or ionizing radiation in the treatment of cancer.

A number of structurally distinct compounds have been reported by showing activity against ATM kinase. WO2015/170081, WO2017/046216 and WO2017/076895 (Astrazeneca AB) reported imidazo[4,5-c]quinolin-2-one compounds as selective modulators of ATM kinase, among which AZD0156 and AZD1390 are potent ATM inhibitors in phase 1 clinical trial:

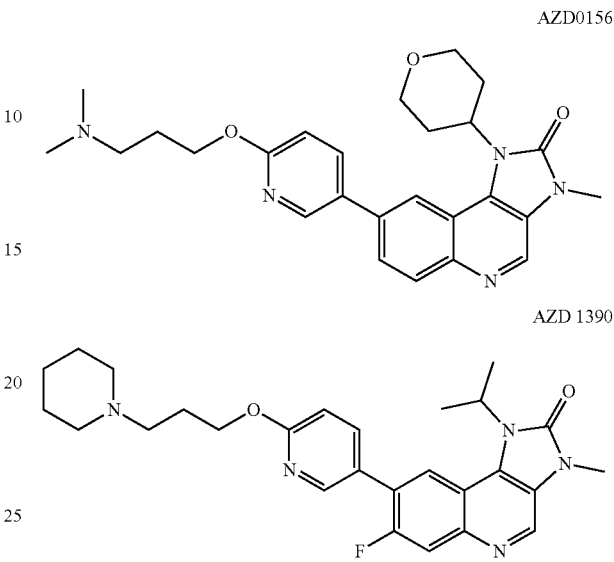

However, both compounds are aldehyde oxidase (AO) substrates with high activity. AO is highly expressed in humans and monkeys, not in dogs and has low expression level in rodents. Compounds metabolized by AO showed high clearance, high PK variability and low oral bioavailability in humans (Garattini, E. et al., *Expert Opin Drug Discovery,* 2013, 641-54; Zientek, M. et al., *Drug Metab Dispos* 2010, 1322-7). AO liability can be evaluated in human liver cytosol system. AZD0156's human PK is unexpectedly lower than prediction (Chen et al., *AACR,* 2018) and a phase 0 clinical PK study was conducted for AZD1390 before making commitment to phase 1 clinical study (NCT03215381 and NCT03423628), further alluding that both AZD0156 and AZD1390 suffer from AO mediated metabolism. Furthermore, AZD0156 is not capable of brain penetration limiting its use for treating tumors in the brain. AZD1390 shows hERG liability, which have cardiac adverse effects.

Accordingly, there remains a need to develop new compounds that act against ATM kinase, preferably being brain penetrable without AO and hEGR liability.

SUMMARY OF THE DISCLOSURE

Disclosed herein are novel substituted imidazo[4,5-c] cinnolin-2-one compounds that possess potent ATM kinase inhibitory activity, do not show AO liability in human liver cytosol and thus have good human pharmacokinetics (PK), low dose and low PK variablity. In addition, these compounds are neither human Pgp nor human BCRP substrates, demonstrate good brain penetration in animals, and possess favourable toxicity profiles (for example a decreased activity against hERG). As a result, the compounds of the present application are particularly useful in the treatment of ATM-associated diseases or conditions, including cancers (not only extracranial cancers, but also tumors in brains).

In one aspect, the present disclosure provides compounds of Formula (I):

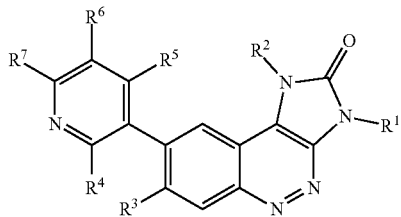

(I)

or a pharmaceutically acceptable salt thereof,
wherein:
$R^1$ is hydrogen or methyl;
$R^2$ is isopropyl or tetrahydropyranyl;
$R^3$ is hydrogen or fluoro;
$R^4$, $R^5$ and $R^6$ are each independently selected from hydrogen or fluoro;
$R^7$ is -L-$NR^8R^9$, wherein L is selected from a direct bond, —$(CH_2)_mO(CH_2)_n$— or —$CONR^{10}(CH_2)_p$—, wherein said —$(CH_2)_mO(CH_2)_n$— and —$CONR^{10}(CH_2)_p$— are optionally substituted by one or more $R^{11}$;
$R^8$ and $R^9$ are each independently selected from the group consisting of hydrogen, alkyl, alkenyl, alkynyl, saturated or unsaturated cycloalkyl, and saturated or unsaturated heterocyclyl, wherein said alkyl, alkenyl, alkynyl, saturated or unsaturated cycloalkyl, and saturated or unsaturated heterocyclyl are optionally substituted with one or more $R^{12}$; or
$R^8$ and $R^9$ together with the nitrogen atom to which they are attached form a saturated or unsaturated heterocyclyl optionally containing one or more additional heteroatoms selected from N, O and S and optionally substituted with one or more $R^{13}$;
$R^{10}$ is selected from the group consisting of hydrogen, alkyl, cycloalkyl, and saturated or unsaturated heterocyclyl which is carbon linked, wherein said heterocyclyl optionally contains one or more additional heteroatoms selected from N, O and S and is optionally substituted with one or more $R^{13}$;
$R^{11}$ is selected from the group consisting of hydrogen, halogen, alkyl, cycloalkyl, alkoxyl, and saturated or unsaturated heterocyclyl optionally containing one or more additional heteroatoms selected from N, O and S and optionally substituted with one or more $R^{13}$;
$R^{12}$ is selected from the group consisting of hydrogen, halogen, cyano, nitro, hydroxyl, alkyl, alkenyl, alkynyl, and alkoxy;
$R^{13}$ is selected from the group consisting of acyl, alkyl, alkenyl, alkynyl, alkoxy, amide, amino, aryl, cyano, cycloalkyl, halogen, haloalkyl, haloalkoxy, heteroaryl, hydroxy, nitro, and —$(CH_2)_qNR^{14}R^{15}$;
$R^{14}$ and $R^{15}$ are each independently selected from the group consisting of hydrogen, alkyl, and cycloalkyl; or
$R^{14}$ and $R^{15}$ together with the nitrogen atom to which they are attached form a saturated or unsaturated heterocyclyl optionally containing one or more additional heteroatoms selected from N, O and S and optionally substituted with one or more $R^{16}$;

$R^{16}$ is selected from the group consisting of acyl, alkyl, alkenyl, alkynyl, alkoxy, amide, amino, aryl, cyano, cycloalkyl, halogen, haloalkyl, haloalkoxy, heteroaryl, hydroxy, and nitro;
m is 0, 1, or 2;
n is an integer in the range of 2 to 4;
p is an integer in the range of 2 to 4; and
q is 0, 1 or 2;
provided that, when $R^2$ is tetrahydropyran-3-yl and $R^3$ is hydrogen, $R^7$ is not —$O(CH_2)_3N(CH_3)_2$.

In another aspect, there is provided a pharmaceutical composition comprising the compound of Formula (I) or a pharmaceutically acceptable salt thereof, and at least one pharmaceutically acceptable excipient.

In a further aspect, there is provided a method of treating ATM-associated diseases or conditions in a subject in need thereof, comprising administering to the subject a therapeutically effective amount of the compound of Formula (I) or a pharmaceutically acceptable salt thereof.

In a further aspect, there is provided a method of treating Huntingdon's disease in a subject in need thereof, comprising administering to the subject a therapeutically effective amount of the compound of Formula (I) or a pharmaceutically acceptable salt thereof.

In a further aspect, there is provided a compound of Formula (I) or a pharmaceutically acceptable salt thereof, for use in the treatment of ATM-associated diseases or conditions.

In a further aspect, there is provided use of a compound of Formula (I) or a pharmaceutically acceptable salt thereof, in the manufacture of a medicament for the treatment of ATM-associated diseases or conditions.

In a further aspect, there is provided a compound of Formula (I) or a pharmaceutically acceptable salt thereof for use in the treatment of ATM-associated diseases or conditions, wherein the compound of Formula (I) is administered simultaneously, separately or sequentially with radiotherapy.

In a further aspect, there is provided a compound of Formula (I) or a pharmaceutically acceptable salt thereof, administered simultaneously, separately or sequentially with at least one additional anti-tumor agent.

DETAILED DESCRIPTION OF THE DISCLOSURE

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature and similar materials differs from or contradicts this application, including but not limited to defined terms, term usage, described techniques, or the like, this application controls.

It is appreciated that certain features of the present disclosure, which are, for clarity, described in the context of separate embodiments, can also be provided in combination in a single embodiment. Conversely, various features of the present disclosure, which are, for brevity, described in the context of a single embodiment, can also be provided separately or in any suitable sub-combination.

Definitions

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, 5$^{th}$ Edition, John Wiley & Sons, Inc., New York, 2001; Larock, Comprehensive Organic Transformations, VCH Publishers, Inc., New York, 1989; Carruthers, Some Modern Methods of Organic Synthesis, 3$^{rd}$ Edition, Cambridge University Press, Cambridge, 1987; the entire contents of each of which are incorporated herein by reference.

At various places in the present disclosure, linking substituents are described. Where the structure clearly requires a linking group, the Markush variables listed for that group are understood to be linking groups. For example, if the structure requires a linking group and the Markush group definition for that variable lists "alkyl", then it is understood that the "alkyl" represents a linking alkylene group.

As used herein, the term "substituted", when refers to a chemical group, means the chemical group has one or more hydrogen atoms that is/are removed and replaced by substituents. The term "substituent", as used herein, has the ordinary meaning known in the art and refers to a chemical moiety that is covalently attached to, or if appropriate, fused to, a parent group. As used herein, the term "optionally substituted" or "optionally . . . substituted" means that the chemical group may have no substituents (i.e. unsubstituted) or may have one or more substituents (i.e. substituted). It is to be understood that substitution at a given atom is limited by valency.

As used herein, the term "$C_{i-j}$" indicates a range of the carbon atoms numbers, wherein i and j are integers and the range of the carbon atoms numbers includes both the endpoints (i.e. i and j) and each integer point in between, and wherein j is greater than i. For examples, $C_{1-6}$ indicates a range of one to six carbon atoms, including one carbon atom, two carbon atoms, three carbon atoms, four carbon atoms, five carbon atoms and six carbon atoms. In some embodiments, the term "$C_{1-12}$" indicates 1 to 12, particularly 1 to 10, particularly 1 to 8, particularly 1 to 6, particularly 1 to 5, particularly 1 to 4, particularly 1 to 3 or particularly 1 to 2 carbon atoms.

As used herein, the term "alkyl", whether as part of another term or used independently, refers to a saturated linear or branched-chain hydrocarbon chain, which may be optionally substituted independently with one or more substituents described below. The term "$C_{i-j}$ alkyl" refers to an alkyl having i to j carbon atoms. In some embodiments, alkyl groups contain 1 to 12 carbon atoms. In some embodiments, alkyl groups contain 1 to 11 carbon atoms. In some embodiments, alkyl groups contain 1 to 11 carbon atoms, 1 to 10 carbon atoms, 1 to 9 carbon atoms, 1 to 8 carbon atoms, 1 to 7 carbon atoms, 1 to 6 carbon atoms, 1 to 5 carbon atoms, 1 to 4 carbon atoms, 1 to 3 carbon atoms, or 1 to 2 carbon atoms. Examples of alkyl group include, but are not limited to, methyl, ethyl, 1-propyl (n-propyl), 2-propyl (isopropyl), 1-butyl (n-butyl), 2-methyl-1-propyl (i-butyl), 2-butyl (s-butyl), 2-methyl-2-propyl (t-butyl), 1-pentyl (n-pentyl), 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, 1-octyl, and the like. Examples of "$C_{1-12}$ alkyl" include, but are not limited to, methyl, ethyl, propyl, butyl, pentyl, hexyl, heptyl, octyl, nonyl, decyl, undecyl, dodecyl. Examples of "$C_{1-6}$ alkyl" are methyl, ethyl, propyl, isopropyl, n-butyl, i-butyl, s-butyl, t-butyl, n-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, and the like.

The alkyl groups can be further substituted by substituents which independently replace one or more hydrogen atoms on one or more carbons of the alkyl groups. Examples of such substituents can include, but are not limited to, acyl, alkyl, alkenyl, alkynyl, halogen, hydroxyl, alkoxyl, haloalkyl, haloalkoxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonate, sulfamoyl, sulfonamido, nitro, trifluoromethyl, cyano, nitro, azido, heterocyclyl, alkylaryl, or an aromatic or heteroaromatic moiety. Alkenyl, alkynyl, saturated or partially unsaturated cycloalkyl, heteroalkyl, heterocyclyl, arylalkyl, heteroarylalkyl, heterocyclylalkyl, cycloalkylalkyl, aryl and heteroaryl groups as described below may also be similarly substituted.

As used herein, the term "alkenyl", whether as part of another term or used independently, refers to linear or branched-chain hydrocarbon radical having at least one carbon-carbon double bond, which may be optionally substituted independently with one or more substituents described herein, and includes radicals having "cis" and "trans" orientations, or alternatively, "E" and "Z" orientations. In some embodiments, alkenyl groups contain 2 to 12 carbon atoms. In some embodiments, alkenyl groups contain 2 to 11 carbon atoms. In some embodiments, alkenyl groups contain 2 to 11 carbon atoms, 2 to 10 carbon atoms, 2 to 9 carbon atoms, 2 to 8 carbon atoms, 2 to 7 carbon atoms, 2 to 6 carbon atoms, 2 to 5 carbon atoms, 2 to 4 carbon atoms, 2 to 3 carbon atoms, and in some embodiments, alkenyl groups contain 2 carbon atoms. Examples of alkenyl group include, but are not limited to, ethylenyl (or vinyl), propenyl, butenyl, pentenyl, 1-methyl-2 buten-1-yl, 5-hexenyl, and the like.

As used herein, the term "alkynyl", whether as part of another term or used independently, refers to a linear or branched hydrocarbon radical having at least one carbon-carbon triple bond, which may be optionally substituted independently with one or more substituents described herein. In some embodiments, alkenyl groups contain 2 to 12 carbon atoms. In some embodiments, alkynyl groups contain 2 to 11 carbon atoms. In some embodiments, alkynyl groups contain 2 to 11 carbon atoms, 2 to 10 carbon atoms, 2 to 9 carbon atoms, 2 to 8 carbon atoms, 2 to 7 carbon atoms, 2 to 6 carbon atoms, 2 to 5 carbon atoms, 2 to 4 carbon atoms, 2 to 3 carbon atoms, and in some embodiments, alkynyl groups contain 2 carbon atoms. Examples of alkynyl group include, but are not limited to, ethynyl, 1-propynyl, 2-propynyl, and the like.

As used herein, the term "alkoxy" or "alkoxyl", whether as part of another term or used independently, refers to an alkyl group, as previously defined, attached to the parent molecule through an oxygen atom. The term "$C_{i-j}$ alkoxy" means that the alkyl moiety of the alkoxy group has i to j carbon atoms. In some embodiments, alkoxy groups contain 1 to 12 carbon atoms. In some embodiments, alkoxy groups contain 1 to 11 carbon atoms. In some embodiments, alkoxy groups contain 1 to 11 carbon atoms, 1 to 10 carbon atoms, 1 to 9 carbon atoms, 1 to 8 carbon atoms, 1 to 7 carbon atoms, 1 to 6 carbon atoms, 1 to 5 carbon atoms, 1 to 4 carbon atoms, 1 to 3 carbon atoms, or 1 to 2 carbon atoms. Examples of "$C_{1-12}$ alkoxyl" include, but are not limited to, methoxy, ethoxy, propoxy (e.g. n-propoxy and isopropoxy), t-butoxy, neopentoxy, n-hexoxy, and the like.

As used herein, the term "acyl" refers to a carbonyl-containing functionality, e.g., —C(═O)R, wherein R is hydrogen or an optionally substituted aliphatic, heteroaliphatic, heterocyclic, aryl, heteroaryl group, or is a substituted (e.g., with hydrogen or aliphatic, heteroaliphatic, aryl, or heteroaryl moieties) oxygen or nitrogen containing functionality (e.g., forming a carboxylic acid, ester, or amide functionality). As used herein, the term "acyloxy" refers to an acyl group attached to the parent molecule through an oxygen atom.

As used herein, the term "amino" or "amine" refers to moieties where a nitrogen atom is covalently bonded to at least one carbon or heteroatom. "Alkylamino" includes groups of compounds wherein nitrogen is bound to at least one alkyl group. Examples of alkylamino groups include benzylamino, methylamino, ethylamino, phenethylamino, etc. "Dialkylamino" includes groups wherein the nitrogen atom is bound to at least two additional alkyl groups. Examples of dialkylamino groups include, but are not limited to, dimethylamino and diethylamino. "Arylamino" and "diarylamino" include groups wherein the nitrogen is bound to at least one or two aryl groups, respectively. "Alkylarylamino", "alkylaminoaryl" or "arylaminoalkyl" refers to an amino group which is bound to at least one alkyl group and at least one aryl group. "Alkaminoalkyl" refers to an alkyl, alkenyl, or alkynyl group bound to a nitrogen atom which is also bound to an alkyl group. "Acylamino" includes groups wherein nitrogen is bound to an acyl group. Examples of acylamino include, but are not limited to, alkylcarbonylamino, arylcarbonylamino, carbamoyl and ureido groups.

As used herein, the term "amide" or "aminocarboxy" refers to compounds or moieties that contain a nitrogen atom that is bound to the carbon of a carbonyl or a thiocarbonyl group. The term includes "alkaminocarboxy" groups that include alkyl, alkenyl or alkynyl groups bound to an amino group which is bound to the carbon of a carbonyl or thiocarbonyl group. It also includes "arylaminocarboxy" groups that include aryl or heteroaryl moieties bound to an amino group that is bound to the carbon of a carbonyl or thiocarbonyl group. The terms "alkylaminocarboxy", "alkenylaminocarboxy", "alkynylaminocarboxy" and "arylaminocarboxy" include moieties wherein alkyl, alkenyl, alkynyl and aryl moieties, respectively, are bound to a nitrogen atom which is in turn bound to the carbon of a carbonyl group. Amides can be substituted with substituents such as straight chain alkyl, branched alkyl, cycloalkyl, aryl, heteroaryl or heterocycle. Substituents on amide groups may be further substituted.

As used herein, the term "aryl", whether as part of another term or used independently, refers to monocyclic and polycyclic ring systems having a total of 5 to 20 ring members, wherein at least one ring in the system is aromatic and wherein each ring in the system contains 3 to 12 ring members. Examples of "aryl" include, but are not limited to, phenyl, biphenyl, naphthyl, anthracyl and the like, which may bear one or more substituents. Also included within the scope of the term "aryl", as it is used herein, is a group in which an aromatic ring is fused to one or more additional rings. In the case of polycyclic ring system, only one of the rings needs to be aromatic (e.g., 2,3-dihydroindole), although all of the rings may be aromatic (e.g., quinoline). The second ring can also be fused or bridged. Examples of polycyclic aryl include, but are not limited to, benzofuranyl, indanyl, phthalimidyl, naphthimidyl, phenanthridinyl, or tetrahydronaphthyl, and the like. Aryl groups can be substituted at one or more ring positions with substituents as described above.

As used herein, the terms "cycloalkyl", "carbocyclyl" and "carbocycle" are interchangeable and whether as part of another term or used independently, refer to a monovalent non-aromatic, saturated or partially unsaturated monocyclic and polycyclic ring system, in which all the ring atoms are carbon and which contains at least three ring forming carbon atoms. In some embodiments, the cycloalkyl may contain 3 to 12 ring forming carbon atoms, 3 to 10 ring forming carbon atoms, 3 to 9 ring forming carbon atoms, 3 to 8 ring forming carbon atoms, 3 to 7 ring forming carbon atoms, 3 to 6 ring forming carbon atoms, 3 to 5 ring forming carbon atoms, 4 to 12 ring forming carbon atoms, 4 to 10 ring forming carbon atoms, 4 to 9 ring forming carbon atoms, 4 to 8 ring forming carbon atoms, 4 to 7 ring forming carbon atoms, 4 to 6 ring forming carbon atoms, 4 to 5 ring forming carbon atoms. Cycloalkyl groups may be saturated or partially unsaturated. Cycloalkyl groups may be substituted. In some embodiments, the cycloalkyl group may be a saturated cyclic alkyl group. In some embodiments, the cycloalkyl group may be a partially unsaturated cyclic alkyl group that contains at least one double bond or triple bond in its ring system.

In some embodiments, the cycloalkyl group may be saturated or partially unsaturated monocyclic carbocyclic ring system, examples of which include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl and cyclododecyl.

In some embodiments, the cycloalkyl group may be saturated or partially unsaturated polycyclic (e.g., bicyclic and tricyclic) carbocyclic ring system, which can be arranged as a fused, spiro or bridged ring system. As used herein, the term "fused ring" refers to a ring system having two rings sharing two adjacent atoms, the term "spiro ring" refers to a ring systems having two rings connected through one single common atom, and the term "bridged ring" refers to a ring system with two rings sharing three or more atoms. Examples of fused carbocyclyl include, but are not limited to, naphthyl, benzopyrenyl, anthracenyl, acenaphthenyl, fluorenyl and the like. Examples of spiro carbocyclyl include, but are not limited to, spiro[5.5]undecanyl, spiropentadienyl, spiro[3.6]-decanyl, and the like. Examples of bridged carbocyclyl include, but are not limited to bicyclo[1,1,1]pentenyl, bicyclo[2,2,1]heptenyl, bicyclo[2.2.1]heptanyl, bicyclo[2.2.2]octanyl, bicyclo[3.3.1]nonanyl, bicyclo[3.3.3]undecanyl, and the like.

As used herein, the term "cyano" refers to —CN.

As used herein, the term "halo" or "halogen" refers to an atom selected from fluorine (or fluoro), chlorine (or chloro), bromine (or bromo) and iodine (or iodo).

As used herein, the term "haloalkyl" refers to an alkyl group substituted with one or more halogen atoms.

As used herein, the term "haloalkoxy" or "haloalkoxyl" refers to an alkoxyl group substituted with one or more halogen atoms.

As used herein, the term "heteroaryl", whether as part of another term or used independently, refers to an aryl group having, in addition to carbon atoms, one or more heteroatoms. As used herein, the term "heteroatom" refers to nitrogen, oxygen, or sulfur, and includes any oxidized form of nitrogen or sulfur, and any quaternized form of a basic nitrogen. Examples of heteroaryl include, but are not limited to, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, benzofuranyl and pteridinyl. The heteroaryl also includes groups in which a heteroaromatic ring is fused to one or more aryl, cycloaliphatic, or heterocyclyl rings, where the radical or point of attachment is on the heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. In some embodiments, the term "5- to 10-membered heteroaryl" refers to a 5- to 6-membered heteroaryl ring having 1 to 3 heteroatoms independently selected from nitrogen, oxygen, or sulfur, or an 8- to 10-membered bicyclic heteroaryl ring having 1 to 4 heteroatoms independently selected from nitrogen, oxygen, or sulfur. In certain embodiments, the term "5- to 12-membered heteroaryl" refers to a 5- to 6-membered heteroaryl ring having 1 to 3 heteroatoms independently selected from nitrogen, oxygen, or sulfur, or an 8- to 12-membered bicyclic heteroaryl ring having 1 to 4 heteroatoms independently selected from nitrogen, oxygen, or sulfur.

As used herein, the term "heterocycle" or "heterocyclyl" refers to a saturated or unsaturated carbocyclyl group in which one or more ring atoms are heteroatoms independently selected from oxygen, sulfur, nitrogen, phosphorus, and the like, the remaining ring atoms being carbon, wherein one or more ring atoms may be optionally substituted independently with one or more substitutents. In some embodiments, the heterocyclyl is a saturated heterocyclyl. In some embodiments, the heterocyclyl is a partially unsaturated heterocyclyl having one or more double bonds in its ring system. In some embodiments, the heterocyclyl may contains any oxidized form of carbon, nitrogen or sulfur, and any quaternized form of a basic nitrogen. "Heterocyclyl" also includes radicals wherein the heterocyclyl radicals are fused with a saturated, partially unsaturated, or fully unsaturated (i.e., aromatic) carbocyclic or heterocyclic ring. The heterocyclyl radical may be carbon linked or nitrogen linked where such is possible. In some embodiments, the heterocycle is carbon linked. In some embodiments, the heterocycle is nitrogen linked. For example, a group derived from pyrrole may be pyrrol-1-yl (nitrogen linked) or pyrrol-3-yl (carbon linked). Further, a group derived from imidazole may be imidazol-1-yl (nitrogen linked) or imidazol-3-yl (carbon linked).

In some embodiments, the term "3- to 12-membered heterocyclyl" refers to a 3- to 12-membered saturated or partially unsaturated monocyclic or polycyclic heterocyclic ring system having 1 to 3 heteroatoms independently selected from nitrogen, oxygen, or sulfur. The fused, spiro and bridged ring systems are also included within the scope of this definition. Examples of monocyclic heterocyclyl include, but are not limited to oxetanyl, 1,1-dioxothietanyl pyrrolidyl, tetrahydrofuryl, tetrahydrothienyl, pyrrolyl, furanyl, thienyl, pyrazolyl, imidazolyl, triazolyl, oxazolyl, thiazolyl, piperidyl, piperazinyl, morpholinyl, pyridinyl, pyrazinyl, pyrimidinyl, pyridazinyl, triazinyl, pyridonyl, pyrimidonyl, pyrazinonyl, pyrimidonyl, pyridazonyl, pyrrolidinyl, triazinonyl, and the like. Examples of fused heterocyclyl include, but are not limited to, phenyl fused ring or pyridinyl fused ring, such as quinolinyl, isoquinolinyl, quinoxalinyl, quinolizinyl, quinazolinyl, azaindolizinyl, pteridinyl, chromenyl, isochromenyl, indolyl, isoindolyl, indolizinyl, indazolyl, purinyl, benzofuranyl, isobenzofuranyl, benzimidazolyl, benzothienyl, benzothiazolyl, carbazolyl, phenazinyl, phenothiazinyl, phenanthridinyl, imidazo[1,2-a]pyridinyl, [1,2,4]triazolo[4,3-a]pyridinyl, [1,2,3]triazolo[4,3-a]pyridinyl groups, and the like. Examples of spiro heterocyclyl include, but are not limited to, spiropyranyl, spirooxazinyl, and the like. Examples of bridged heterocyclyl include, but are not limited to, morphanyl, hexamethylenetetraminyl, 3-aza-bicyclo[3.1.0]hexane, 8-aza-bicyclo[3.2.1]octane, 1-aza-bicyclo[2.2.2]octane, 1,4-diazabicyclo[2.2.2]octane (DABCO), and the like.

As used herein, the term "partially unsaturated" refers to a radical that includes at least one double or triple bond. The term "partially unsaturated" is intended to encompass rings having multiple sites of unsaturation, but is not intended to include aromatic (i.e., fully unsaturated) moieties.

As used herein, the term "substituted", whether preceded by the term "optionally" or not, means that one or more hydrogens of the designated moiety are replaced with a suitable substituent. It will be understood that "substitution" or "substituted with" includes the implicit proviso that such substitution is in accordance with permitted valence of the substituted atom and that the substitution results in a stable or chemically feasible compound, e.g., which does not spontaneously undergo transformation such as by rearrangement, cyclization, elimination, etc. Unless otherwise indicated, an "optionally substituted" group may have a suitable substituent at each substitutable position of the group, and when more than one position in any given structure may be substituted with more than one substituent selected from a specified group, the substituent may be either the same or different at every position. It will be understood by those skilled in the art that substituents can themselves be substituted, if appropriate. Unless specifically stated as "unsubstituted", references to chemical moieties herein are understood to include substituted variants. For example, reference to an "aryl" group or moiety implicitly includes both substituted and unsubstituted variants.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., $R^i$) occurs more than one time in any constituent or formula for a compound, its definition at each occurrence is independent of its definition at every other occurrence. Thus, for example, if a group is shown to be substituted with 0-2 $R^i$ moieties, then the group may optionally be substituted with up to two $R^i$ moieties and $R^i$ at each occurrence is selected independently from the definition of $R^i$. Also, combinations of substituents and/or variables are permissible, but only if such combinations result in stable compounds.

Compound

The present disclosure provides novel substituted imidazo [4,5-c]cinnolin-2-one compounds and pharmaceutically acceptable salts thereof, synthetic methods for making the compounds, pharmaceutical compositions containing them and various uses of the disclosed compounds.

In one aspect, the present disclosure provides a compound of Formula (I):

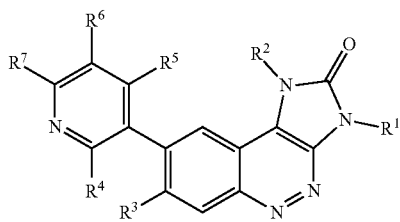

or a pharmaceutically acceptable salt thereof, wherein:
$R^1$ is hydrogen or methyl;
$R^2$ is isopropyl or tetrahydropyranyl;
$R^3$ is hydrogen or fluoro;
$R^4$, $R^5$ and $R^6$ are each independently selected from hydrogen or fluoro;
$R^7$ is -L-$NR^8R^9$, wherein L is selected from a direct bond, $-(CH_2)_mO(CH_2)_n-$ or $-CONR^{10}(CH_2)_p-$, wherein said $-(CH_2)_mO(CH_2)_n-$ and $-CONR^{10}(CH_2)_p-$ are optionally substituted by one or more $R^{11}$;
$R^8$ and $R^9$ are each independently selected from the group consisting of hydrogen, alkyl, alkenyl, alkynyl, saturated or unsaturated cycloalkyl, and saturated or unsaturated heterocyclyl, wherein said alkyl, alkenyl, alkynyl, saturated or unsaturated cycloalkyl, and saturated or unsaturated heterocyclyl are optionally substituted with one or more $R^{12}$; or
$R^8$ and $R^9$ together with the nitrogen atom to which they are attached form a saturated or unsaturated heterocyclyl optionally containing one or more additional heteroatoms selected from N, O and S and optionally substituted with one or more $R^{13}$;
$R^{10}$ is selected from the group consisting of hydrogen, alkyl, cycloalkyl, and saturated or unsaturated heterocyclyl which is carbon linked, wherein said heterocyclyl optionally contains one or more additional heteroatoms selected from N, O and S and is optionally substituted with one or more $R^{13}$;
$R^{11}$ is selected from the group consisting of hydrogen, halogen, alkyl, cycloalkyl, alkoxyl, and saturated or unsaturated heterocyclyl optionally containing one or more additional heteroatoms selected from N, O and S and optionally substituted with one or more $R^{13}$;
$R^{12}$ is selected from the group consisting of hydrogen, halogen, cyano, nitro, hydroxyl, alkyl, alkenyl, alkynyl, and alkoxy;
$R^{13}$ is selected from the group consisting of acyl, alkyl, alkenyl, alkynyl, alkoxy, amide, amino, aryl, cyano, cycloalkyl, halogen, haloalkyl, haloalkoxy, heteroaryl, hydroxy, nitro, and $-(CH_2)_qNR^{14}R^{15}$;
$R^{14}$ and $R^{15}$ are each independently selected from the group consisting of hydrogen, alkyl, and cycloalkyl; or
$R^{14}$ and $R^{15}$ together with the nitrogen atom to which they are attached form a saturated or unsaturated heterocyclyl optionally containing one or more additional heteroatoms selected from N, O and S and optionally substituted with one or more $R^{16}$;
$R^{16}$ is selected from the group consisting of acyl, alkyl, alkenyl, alkynyl, alkoxy, amide, amino, aryl, cyano, cycloalkyl, halogen, haloalkyl, haloalkoxy, heteroaryl, hydroxy, and nitro;
m is 0, 1, or 2;
n is an integer in the range of 2 to 4;
p is an integer in the range of 2 to 4; and
q is 0, 1 or 2;
provided that, when $R^2$ is tetrahydropyran-3-yl and $R^3$ is hydrogen, $R^7$ is not $-O(CH_2)_3N(CH_3)_2$.

In some embodiments, $R^1$ is hydrogen.
In some embodiments, $R^1$ is methyl.
In some embodiments, $R^2$ is isopropyl.
In some embodiments, $R^2$ is tetrahydropyranyl.
In some embodiments, $R^2$ is tetrahydropyran-3-yl.
In some embodiments, $R^3$ is hydrogen.
In some embodiments, $R^3$ is fluoro.
In some embodiments, where $R^2$ is tetrahydropyran-3-yl and $R^3$ is hydrogen, then $R^7$ is not $-O(CH_2)_3N(CH_3)_2$.
In some embodiments, $R^4$, $R^5$ and $R^6$ are hydrogen.
In some embodiments, $R^4$ is fluoro, and $R^5$ and $R^6$ are hydrogen.
In some embodiments, $R^7$ is -L-$NR^8R^9$, L is $-(CH_2)_mO(CH_2)_n-$ optionally substituted by one or more $R^{11}$; wherein m is 0, 1, or 2, n is an integer in the range of 2 to 4, wherein $R^{11}$ is selected from the group consisting of hydrogen, halogen, alkyl, cycloalkyl, alkoxyl, and saturated or unsaturated heterocyclyl.
In some embodiments, $R^7$ is -L-$NR^8R^9$, L is $-(CH_2)_mO(CH_2)_n-$, $R^8$ and $R^9$ are each independently selected from $C_{1-6}$ alkyl optionally substituted with one or more $R^{12}$, wherein the combination of m and n is selected from m is 0 and n is 3, or m is 1 and n is 2; $R^{12}$ is selected from the group consisting of hydrogen, halogen, cyano, nitro, hydroxyl, alkyl, alkenyl, alkynyl, and alkoxy.
In some embodiments, $R^7$ is -L-$NR^8R^9$, L is $-(CH_2)_mO(CH_2)_n-$, $R^8$ and $R^9$ are independently selected from methyl, ethyl, propyl, or butyl, wherein the combination of m and n is selected from m is 0 and n is 3, or m is 1 and n is 2.
In certain embodiments, $R^7$ is -L-$NR^8R^9$, L is $-(CH_2)_mO(CH_2)_n-$, $R^8$ and $R^9$ are methyl, the combination of m and n is selected from m is 0 and n is 3, or m is 1 and n is 2.
In some embodiments, $R^7$ is -L-$NR^8R^9$, L is $-(CH_2)_mO(CH_2)_n-$, $R^8$ and $R^9$ together with the nitrogen atom to which they are attached form:

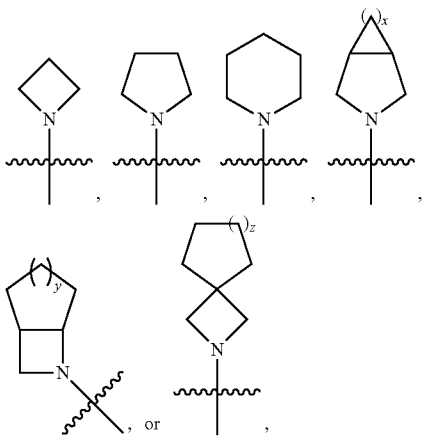

, or ,

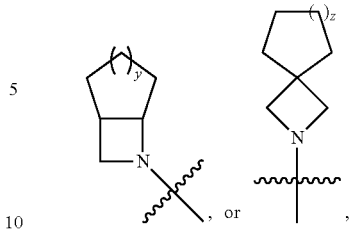

, or , each of which is optionally substituted with one or more $R^{13}$, wherein the combination of m and n is selected from m is 0 and n is 3, or m is 1 and n is 2; x is 1, 2, 3 or 4; y is 0, 1 or 2; z is 0, 1 or 2; and $R^{13}$ is selected from the group consisting of acyl, alkyl, alkenyl, alkynyl, alkoxy, amide, amino, alkylamino, aryl, cyano, cycloalkyl, halogen, haloalkyl, haloalkoxy, heteroaryl, hydroxy, and nitro.

In some embodiments, $R^7$ is -L-$NR^8R^9$, L is —$(CH_2)_mO(CH_2)_n$—, the combination of m and n is selected from m is 0 and n is 3, or m is 1 and n is 2; and $R^8$ and $R^9$ together with the nitrogen atom to which they are attached form azetidinyl, pyrrolidinyl, piperidinyl or azabicyclo[3.1.0]hexan-3-yl, said azetidinyl, pyrrolidinyl, piperidinyl or azabicyclo[3.1.0]hexan-3-yl is optionally substituted with one or more $R^{13}$, wherein $R^{13}$ is halogen. In certain embodiments, $R^{13}$ is fluoro. In certain embodiments, $R^7$ is -L-$NR^8R^9$, L is —$(CH_2)_mO(CH_2)_n$—, the combination of m and n is selected from m is 0 and n is 3, or m is 1 and n is 2; and $R^8$ and $R^9$ together with the nitrogen atom to which they are attached form pyrrolidinyl optionally substituted with one or more fluoro.

In certain embodiments, $R^7$ is -L-$NR^8R^9$, L is —$(CH_2)_mO(CH_2)_n$—, the combination of m and n is selected from m is 0 and n is 3, or m is 1 and n is 2; and $R^8$ and $R^9$ together with the nitrogen atom to which they are attached form piperidinyl optionally substituted with one or more fluoro.

In certain embodiments, $R^7$ is -L-$NR^8R^9$, L is —$(CH_2)_mO(CH_2)_n$—, the combination of m and n is selected from m is 0 and n is 3, or m is 1 and n is 2; and $R^8$ and $R^9$ together with the nitrogen atom to which they are attached form azabicyclo[3.1.0]hexan-3-yl optionally substituted with fluoro.

In some embodiments, when m is 0 and n is 3, $R^{13}$ is not halogen.

In some embodiments, when m is 0 and n is 3, $R^{13}$ is not azabicyclo[3.1.0]hexan-3-yl.

In some embodiments, $R^7$ is -L-$NR^8R^9$, L is a direct bond, and $R^8$ and $R^9$ together with the nitrogen atom to which they are attached form:

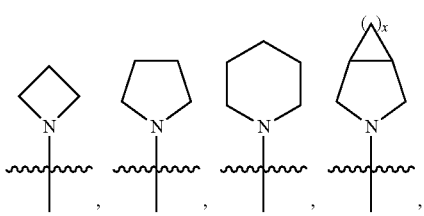

, each of which is optionally substituted with one or more $R^{13}$, wherein x is 1, 2, 3 or 4; y is 0, 1 or 2; z is 0, 1 or 2; $R^{13}$ is selected from the group consisting of acyl, alkyl, alkenyl, alkynyl, alkoxy, amide, amino, alkylamino, aryl, cyano, cycloalkyl, halogen, haloalkyl, haloalkoxy, heteroaryl, hydroxy, nitro and —$(CH_2)_qNR^{14}R^{15}$; wherein q is 0, 1 or 2; $R^{14}$ and $R^{15}$ are each independently selected from the group consisting of hydrogen, alkyl, and cycloalkyl, or $R^{14}$ and $R^{15}$ together with the nitrogen atom to which they are attached form a saturated or unsaturated heterocyclyl optionally containing one or more additional heteroatoms selected from N, O and S and optionally substituted with one or more $R^{16}$; wherein $R^{16}$ is selected from the group consisting of acyl, alkyl, alkenyl, alkynyl, alkoxy, amide, amino, aryl, cyano, cycloalkyl, halogen, haloalkyl, haloalkoxy, heteroaryl, hydroxy, and nitro.

In some embodiments, $R^7$ is -L-$NR^8R^9$, L is a direct bond, and $R^8$ and $R^9$ together with the nitrogen atom to which they are attached form azetidinyl, pyrrolidinyl, or piperidinyl, said azetidinyl, pyrrolidinyl, or piperidinyl is optionally substituted with one or more $R^{13}$ wherein $R^{13}$ is selected from the group consisting of alkyl, alkenyl, alkynyl, alkoxy, amide, amino, alkylamino, aryl, cyano, cycloalkyl, halogen, haloalkyl, haloalkoxy, heteroaryl, hydroxy, nitro and —$(CH_2)_qNR^{14}R^{15}$; wherein q is 0, 1 or 2; $R^{14}$ and $R^{15}$ are each independently selected from the group consisting of hydrogen, alkyl, and cycloalkyl.

In some embodiments, $R^7$ is -L-$NR^8R^9$, L is a direct bond, and $R^8$ and $R^9$ together with the nitrogen atom to which they are attached form azetidinyl, pyrrolidinyl, or piperidinyl, said azetidinyl, pyrrolidinyl, or piperidinyl is optionally substituted with one or more $R^{13}$ wherein $R^{13}$ is —$(CH_2)_qNR^{14}R^{15}$; wherein q is 0, 1 or 2; $R^{14}$ and $R^{15}$ are each independently selected from $C_{1-6}$ alkyl. In certain embodiments, $R^{14}$ and $R^{15}$ are methyl.

In certain embodiments, $R^7$ is -L-$NR^8R^9$, L is a direct bond, and $R^8$ and $R^9$ together with the nitrogen atom to which they are attached form pyrrolidinyl optionally substituted with one or more —$N(CH_3)_2$ or —$(CH_2)N(CH_3)_2$ groups.

In certain embodiments, $R^7$ is -L-$NR^8R^9$, L is a direct bond, and $R^8$ and $R^9$ together with the nitrogen atom to which they are attached form piperidinyl optionally substituted with one or more —$N(CH_3)_2$ or —$(CH_2)N(CH_3)_2$ groups.

In some embodiments, $R^7$ is -L-$NR^8R^9$, L is —$CONR^{10}(CH_2)_p$—, $R^8$ and $R^9$ are each independently selected from $C_{1-6}$ alkyl optionally substituted with one or more $R^{12}$, wherein p is an integer in the range of 2 to 4, $R^{10}$ is selected from the group consisting of hydrogen, alkyl, cycloalkyl, and saturated or unsaturated heterocyclyl which is carbon linked, $R^{12}$ is selected from the group consisting of hydrogen, halogen, cyano, nitro, hydroxyl, alkyl, alkenyl, alkynyl, and alkoxy.

In some embodiments, $R^7$ is -L-$NR^8R^9$, L is —$CONR^{10}$($CH_2$)$_p$—, $R^8$ and $R^9$ are selected from methyl, ethyl, propyl, or butyl; p is 2; $R^{10}$ is hydrogen.

In certain embodiments, $R^7$ is -L-$NR^8R^9$, L is —CONH($CH_2$)$_2$—, $R^8$ and $R^9$ are methyl.

In one aspect, the present disclosure provides a compound of Formula (I):

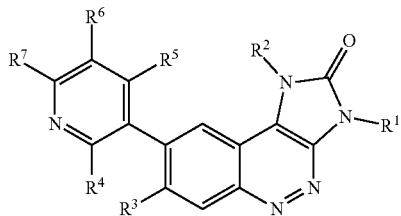

(I)

or a pharmaceutically acceptable salt thereof, wherein:
$R^1$ is methyl;
$R^2$ is isopropyl;
$R^3$ is fluoro;
$R^4$, $R^5$ and $R^6$ are hydrogen;
$R^7$ is -L-$NR^8R^9$, wherein L, $R^8$, and $R^9$ are defined as supra.

In certain embodiments, L is —($CH_2$)$_m$O($CH_2$)$_n$— optionally substituted by one or more $R^{11}$;
$R^8$ and $R^9$ are each independently selected from $C_{1-6}$ alkyl optionally substituted with one or more $R^{12}$; or
$R^8$ and $R^9$ together with the nitrogen atom to which they are attached form

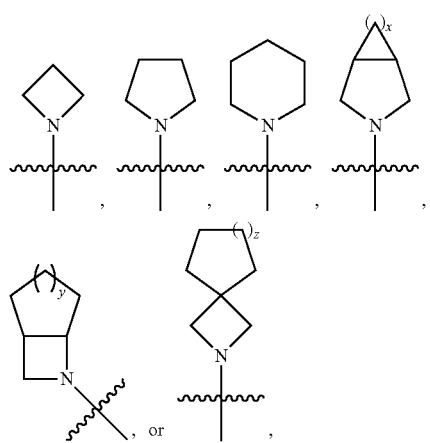

each of which is optionally substituted with one or more $R^{13}$, wherein x is 1, 2, 3 or 4; y is 0, 1 or 2; and z is 0, 1 or 2;
$R^{11}$ is hydrogen;
$R^{12}$ is hydrogen;
$R^{13}$ is halogen;
m is 0, 1, or 2;
n is an integer in the range of 2 to 4.

In certain embodiments, L is —$CONR^{10}$($CH_2$)$_p$—, optionally substituted by one or more $R^{11}$;
$R^8$ and $R^9$ are each independently selected from $C_{1-6}$ alkyl optionally substituted with one or more $R^2$;
$R^{10}$ is hydrogen;
$R^{12}$ is hydrogen; and p is an integer in the range of 2 to 4.

In certain embodiments, L is a direct bond; and
$R^8$ and $R^9$ together with the nitrogen atom to which they are attached form pyrrolidinyl or piperidinyl, optionally substituted with one or more $R^{13}$;
$R^{13}$ is —($CH_2$)$_q$$NR^{14}R^{15}$;
$R^{14}$ and $R^{15}$ are each independently selected from $C_{1-6}$ alkyl; and
q is 0, 1 or 2.

In one aspect, the present disclosure provides a compound of Formula (I) or a pharmaceutically acceptable salt thereof selected from the group consisting of:
7-fluoro-1-isopropyl-3-methyl-8-(6-(3-(piperidin-1-yl)propoxy)pyridin-3-yl)-1,3-dihydro-2H-imidazo[4,5-c]cinnolin-2-one;
8-(6-(3-(dimethylamino)propoxy)pyridin-3-yl)-7-fluoro-1-isopropyl-3-methyl-1,3-dihydro-2H-imidazo[4,5-c]cinnolin-2-one;
7-fluoro-1-isopropyl-3-methyl-8-(6-(3-(pyrrolidin-1-yl)propoxy)pyridin-3-yl)-1,3-dihydro-2H-imidazo[4,5-c]cinnolin-2-one;
8-(6-(4-(dimethylamino)piperidin-1-yl)pyridin-3-yl)-7-fluoro-1-isopropyl-3-methyl-1,3-dihydro-2H-imidazo[4,5-c]cinnolin-2-one;
8-(6-(3-((dimethylamino)methyl)pyrrolidin-1-yl)pyridin-3-yl)-7-fluoro-1-isopropyl-3-methyl-1,3-dihydro-2H-imidazo[4,5-c]cinnolin-2-one;
8-(6-((2-(dimethylamino)ethoxy)methyl)pyridin-3-yl)-7-fluoro-1-isopropyl-3-methyl-1,3-dihydro-2H-imidazo[4,5-c]cinnolin-2-one;
7-fluoro-1-isopropyl-3-methyl-8-(6-((2-(piperidin-1-yl)ethoxy)methyl)pyridin-3-yl)-1,3-dihydro-2H-imidazo[4,5-c]cinnolin-2-one;
7-fluoro-1-isopropyl-3-methyl-8-(6-((2-(pyrrolidin-1-yl)ethoxy)methyl)pyridin-3-yl)-1,3-dihydro-2H-imidazo[4,5-c]cinnolin-2-one;
(R)-7-fluoro-8-(6-((2-(3-fluoropyrrolidin-1-yl)ethoxy)methyl)pyridin-3-yl)-1-isopropyl-3-methyl-1,3-dihydro-2H-imidazo[4,5-c]cinnolin-2-one;
7-fluoro-8-(6-((2-(4-fluoropiperidin-1-yl)ethoxy)methyl)pyridin-3-yl)-1-isopropyl-3-methyl-1,3-dihydro-2H-imidazo[4,5-c]cinnolin-2-one;
8-(6-((2-(3-azabicyclo[3.1.0]hexan-3-yl)ethoxy)methyl)pyridin-3-yl)-7-fluoro-1-isopropyl-3-methyl-1,3-dihydro-2H-imidazo[4,5-c]cinnolin-2-one;
N-(2-(dimethylamino)ethyl)-5-(7-fluoro-1-isopropyl-3-methyl-2-oxo-2,3-dihydro-1H-imidazo[4,5-c]cinnolin-8-yl)picolinamide;
7-fluoro-8-(6-(3-(4-fluoropiperidin-1-yl)propoxy)pyridin-3-yl)-1-isopropyl-3-methyl-1,3-dihydro-2H-imidazo[4,5-c]cinnolin-2-one;
(S)-7-fluoro-8-(6-(3-(3-fluoropyrrolidin-1-yl)propoxy)pyridin-3-yl)-1-isopropyl-3-methyl-1,3-dihydro-2H-imidazo[4,5-c]cinnolin-2-one;
(R)-7-fluoro-8-(6-(3-(3-fluoropyrrolidin-1-yl)propoxy)pyridin-3-yl)-1-isopropyl-3-methyl-1,3-dihydro-2H-imidazo[4,5-c]cinnolin-2-one;
8-(6-(3-(3-azabicyclo[3.1.0]hexan-3-yl)propoxy)pyridin-3-yl)-7-fluoro-1-isopropyl-3-methyl-1,3-dihydro-2H-imidazo[4,5-c]cinnolin-2-one;
8-(6-(3-(dimethylamino)propoxy)-2-fluoropyridin-3-yl)-7-fluoro-1-isopropyl-3-methyl-1,3-dihydro-2H-imidazo[4,5-c]cinnolin-2-one;
7-fluoro-3-methyl-8-(6-(3-(piperidin-1-yl)propoxy)pyridin-3-yl)-1-(tetrahydro-2H-pyran-4-yl)-1,3-dihydro-2H-imidazo[4,5-c]cinnolin-2-one;
8-(6-(3-(dimethylamino)propoxy)pyridin-3-yl)-7-fluoro-3-methyl-1-(tetrahydro-2H-pyran-4-yl)-1,3-dihydro-2H-imidazo[4,5-c]cinnolin-2-one;

7-fluoro-3-methyl-8-(6-(3-(pyrrolidin-1-yl)propoxy)pyridin-3-yl)-1-(tetrahydro-2H-pyran-4-yl)-1,3-dihydro-2H-imidazo[4,5-c]cinnolin-2-one;

8-(6-(3-((dimethylamino)methyl)pyrrolidin-1-yl)pyridin-3-yl)-7-fluoro-3-methyl-1-(tetrahydro-2H-pyran-4-yl)-1,3-dihydro-2H-imidazo[4,5-c]cinnolin-2-one;

8-(6-(4-(dimethylamino)piperidin-1-yl)pyridin-3-yl)-7-fluoro-3-methyl-1-(tetrahydro-2H-pyran-4-yl)-1,3-dihydro-2H-imidazo[4,5-c]cinnolin-2-one;

8-(6-((2-(dimethylamino)ethoxy)methyl)pyridin-3-yl)-7-fluoro-3-methyl-1-(tetrahydro-2H-pyran-4-yl)-1,3-dihydro-2H-imidazo[4,5-c]cinnolin-2-one;

7-fluoro-8-(6-(3-(4-fluoropiperidin-1-yl)propoxy)pyridin-3-yl)-3-methyl-1-(tetrahydro-2H-pyran-4-yl)-1,3-dihydro-2H-imidazo[4,5-c]cinnolin-2-one;

(R)-7-fluoro-8-(6-(3-(3-fluoropyrrolidin-1-yl)propoxy)pyridin-3-yl)-3-methyl-1-(tetrahydro-2H-pyran-4-yl)-1,3-dihydro-2H-imidazo[4,5-c]cinnolin-2-one;

8-(6-((2-(diethylamino)ethoxy)methyl)pyridin-3-yl)-7-fluoro-1-isopropyl-3-methyl-1,3-dihydro-2H-imidazo[4,5-c]cinnolin-2-one;

8-(6-((2-(ethyl(methyl)amino)ethoxy)methyl)pyridin-3-yl)-7-fluoro-1-isopropyl-3-methyl-1,3-dihydro-2H-imidazo[4,5-c]cinnolin-2-one;

7-fluoro-1-isopropyl-3-methyl-8-(6-((2-morpholinoethoxy)methyl)pyridin-3-yl)-1,3-dihydro-2H-imidazo[4,5-c]cinnolin-2-one;

7-fluoro-1-isopropyl-3-methyl-8-(6-((2-(piperazin-1-yl)ethoxy)methyl)pyridin-3-yl)-1,3-dihydro-2H-imidazo[4,5-c]cinnolin-2-one;

7-fluoro-1-isopropyl-3-methyl-8-(6-((2-(4-methylpiperazin-1-yl)ethoxy)methyl)pyridin-3-yl)-1,3-dihydro-2H-imidazo[4,5-c]cinnolin-2-one;

8-(6-((2-(4-cyclopropylpiperazin-1-yl)ethoxy)methyl)pyridin-3-yl)-7-fluoro-1-isopropyl-3-methyl-1,3-dihydro-2H-imidazo[4,5-c]cinnolin-2-one;

8-(6-((2-(2-azaspiro[3.3]heptan-2-yl)ethoxy)methyl)pyridin-3-yl)-7-fluoro-1-isopropyl-3-methyl-1,3-dihydro-2H-imidazo[4,5-c]cinnolin-2-one;

8-(6-((2-(2-oxa-6-azaspiro[3.3]heptan-6-yl)ethoxy)methyl)pyridin-3-yl)-7-fluoro-1-isopropyl-3-methyl-1,3-dihydro-2H-imidazo[4,5-c]cinnolin-2-one;

8-(6-((2-(2-azaspiro[3.4]octan-2-yl)ethoxy)methyl)pyridin-3-yl)-7-fluoro-1-isopropyl-3-methyl-1,3-dihydro-2H-imidazo[4,5-c]cinnolin-2-one;

8-(6-((2-(6-azabicyclo[3.2.0]heptan-6-yl)ethoxy)methyl)pyridin-3-yl)-7-fluoro-1-isopropyl-3-methyl-1,3-dihydro-2H-imidazo[4,5-c]cinnolin-2-one;

8-(6-(3-(diethylamino)propoxy)pyridin-3-yl)-7-fluoro-1-isopropyl-3-methyl-1,3-dihydro-2H-imidazo[4,5-c]cinnolin-2-one;

8-(6-(3-(ethyl(methyl)amino)propoxy)pyridin-3-yl)-7-fluoro-1-isopropyl-3-methyl-1,3-dihydro-2H-imidazo[4,5-c]cinnolin-2-one 7-fluoro-1-isopropyl-3-methyl-8-(6-(3-morpholinopropoxy)pyridin-3-yl)-1,3-dihydro-2H-imidazo[4,5-c]cinnolin-2-one;

7-fluoro-1-isopropyl-3-methyl-8-(6-(3-(piperazin-1-yl)propoxy)pyridin-3-yl)-1,3-dihydro-2H-imidazo[4,5-c]cinnolin-2-one;

7-fluoro-1-isopropyl-3-methyl-8-(6-(3-(4-methylpiperazin-1-yl)propoxy)pyridin-3-yl)-1,3-dihydro-2H-imidazo[4,5-c]cinnolin-2-one;

8-(6-(3-(4-cyclopropylpiperazin-1-yl)propoxy)pyridin-3-yl)-7-fluoro-1-isopropyl-3-methyl-1,3-dihydro-2H-imidazo[4,5-c]cinnolin-2-one;

8-(6-(3-(2-azaspiro[3.3]heptan-2-yl)propoxy)pyridin-3-yl)-7-fluoro-1-isopropyl-3-methyl-1,3-dihydro-2H-imidazo[4,5-c]cinnolin-2-one;

8-(6-(3-(2-oxa-6-azaspiro[3.3]heptan-6-yl)propoxy)pyridin-3-yl)-7-fluoro-1-isopropyl-3-methyl-1,3-dihydro-2H-imidazo[4,5-c]cinnolin-2-one;

8-(6-(3-(2-azaspiro[3.4]octan-2-yl)propoxy)pyridin-3-yl)-7-fluoro-1-isopropyl-3-methyl-1,3-dihydro-2H-imidazo[4,5-c]cinnolin-2-one and 8-(6-(3-(6-azabicyclo[3.2.0]heptan-6-yl)propoxy)pyridin-3-yl)-7-fluoro-1-isopropyl-3-methyl-1,3-dihydro-2H-imidazo[4,5-c]cinnolin-2-one.

Exemplary compounds of Formula (I) are set forth in Table 1 below.

TABLE 1

| Cmpd No. | Compound Structure and Name |
| --- | --- |
| 1 | 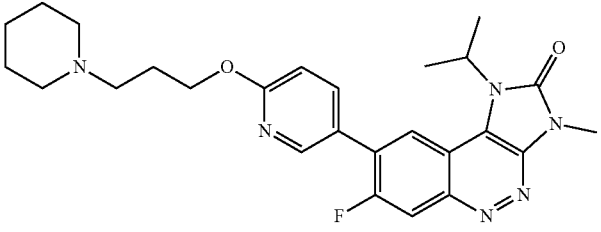 [SMILES: CC(C)n1c(=O)n(C)c2nnc3cc(F)c(-c4ccc(OCCCN5CCCCC5)nc4)cc3c21]<br>7-fluoro-1-isopropyl-3-methyl-8-(6-(3-(piperidin-1-yl)propoxy)pyridin-3-yl)-1H-imidazo[4,5-c]cinnolin-2(3H)-one |
| 2 | 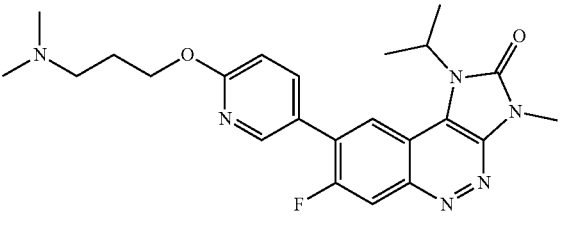<br>8-(6-(3-(dimethylamino)propoxy)pyridin-3-yl)-7-fluoro-1-isopropyl-3-methyl-1H-imidazo[4,5-c]cinnolin-2(3H)-one |

TABLE 1-continued

| Cmpd No. | Compound Structure and Name |
|---|---|
| 3 | 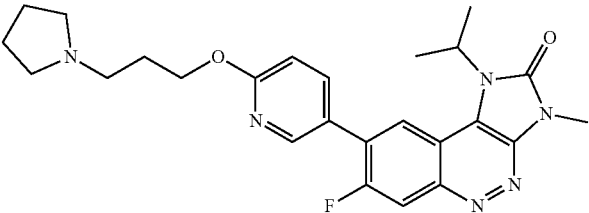 [SMILES: CC(C)n1c(=O)n(C)c2nnc3cc(F)c(-c4ccc(OCCCN5CCCC5)nc4)cc3c21]<br>7-fluoro-1-isopropyl-3-methyl-8-(6-(3-(pyrrolidin-1-yl)propoxy)pyridin-3-yl)-1H-imidazo[4,5-c]cinnolin-2(3H)-one |
| 4 | 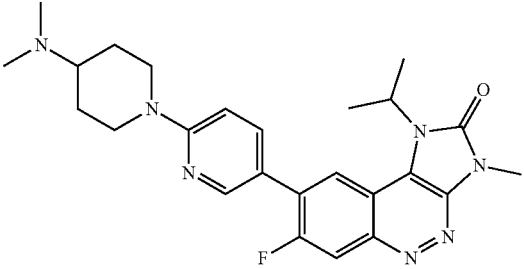<br>8-(6-(4-(dimethylamino)piperidin-1-yl)pyridin-3-yl)-7-fluoro-1-isopropyl-3-methyl-1H-imidazo[4,5-c]cinnolin-2(3H)-one |
| 5 | 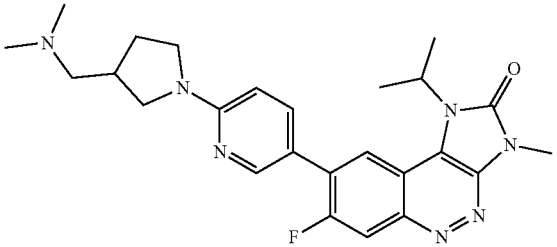<br>8-(6-(3-((dimethylamino)methyl)pyrrolidin-1-yl)pyridin-3-yl)-7-fluoro-1-isopropyl-3-methyl-1H-imidazo[4,5-c]cinnolin-2(3H)-one |
| 6 | 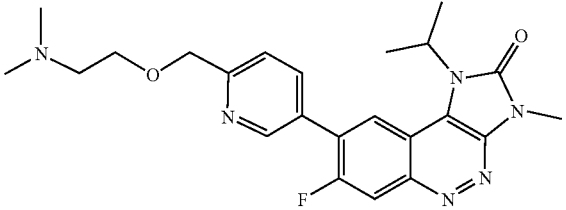<br>8-(6-((2-(dimethylamino)ethoxy)methyl)pyridin-3-yl)-7-fluoro-1-isopropyl-3-methyl-1H-imidazo[4,5-c]cinnolin-2(3H)-one |
| 7 | 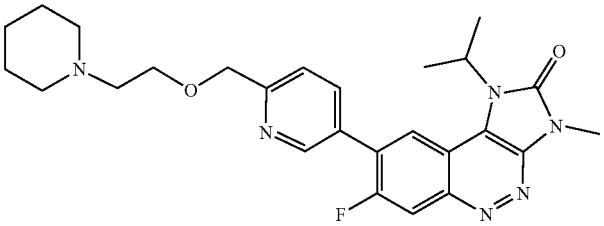 [SMILES: CC(C)n1c(=O)n(C)c2nnc3cc(F)c(-c4ccc(COCCN5CCCCC5)nc4)cc3c21]<br>7-fluoro-1-isopropyl-3-methyl-8-(6-((2-(piperidin-1-yl)ethoxy)methyl)pyridin-3-yl)-1H-imidazo[4,5-c]cinnolin-2(3H)-one |

TABLE 1-continued

| Cmpd No. | Compound Structure and Name |
|---|---|
| 8 | 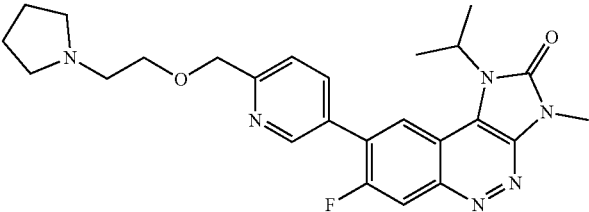 [SMILES: CC(C)n1c(=O)n(C)c2nnc3cc(F)c(-c4ccc(COCCN5CCCC5)nc4)cc3c21]<br>7-fluoro-1-isopropyl-3-methyl-8-(6-((2-(pyrrolidin-1-yl)ethoxy)methyl)pyridin-3-yl)-1H-imidazo[4,5-c]cinnolin-2(3H)-one |
| 9 | 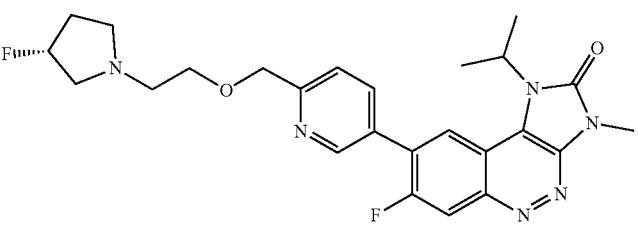 [SMILES: CC(C)n1c(=O)n(C)c2nnc3cc(F)c(-c4ccc(COCCN5CC[C@@H](F)C5)nc4)cc3c21]<br>(R)-7-fluoro-8-(6-((2-(3-fluoropyrrolidin-1-yl)ethoxy)methyl)pyridin-3-yl)-1-isopropyl-3-methyl-1H-imidazo[4,5-c]cinnolin-2(3H)-one |
| 10 | 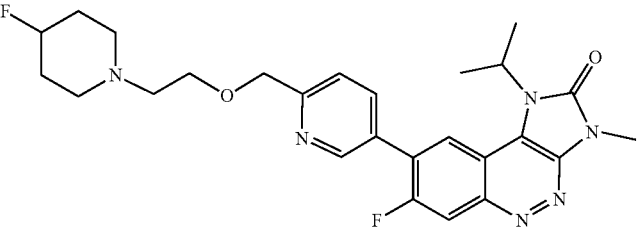 [SMILES: CC(C)n1c(=O)n(C)c2nnc3cc(F)c(-c4ccc(COCCN5CCC(F)CC5)nc4)cc3c21]<br>7-fluoro-8-(6-((2-(4-fluoropiperidin-1-yl)ethoxy)methyl)pyridin-3-yl)-1-isopropyl-3-methyl-1H-imidazo[4,5-c]cinnolin-2(3H)-one |
| 11 | 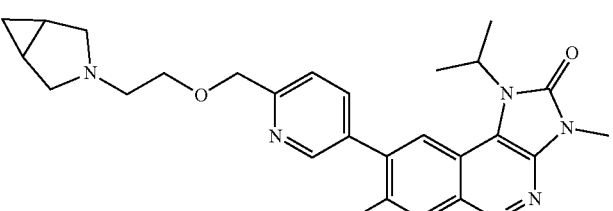<br>8-(6-((2-(3-azabicyclo[3.1.0]hexan-3-yl)ethoxy)methyl)pyridin-3-yl)-7-fluoro-1-isopropyl-3-methyl-1H-imidazo[4,5-c]cinnolin-2(3H)-one |
| 12 | 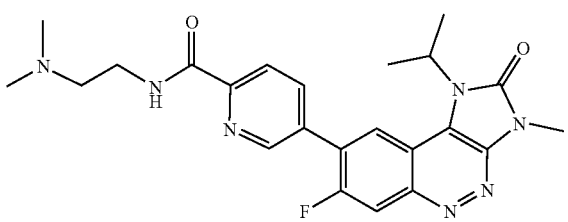<br>N-(2-(dimethylamino)ethyl)-5-(7-fluoro-1-isopropyl-3-methyl-2-oxo-2,3-dihydro-1H-imidazo[4,5-c]cinnolin-8-yl)picolinamide |

TABLE 1-continued

| Cmpd No. | Compound Structure and Name |
|---|---|
| 13 | 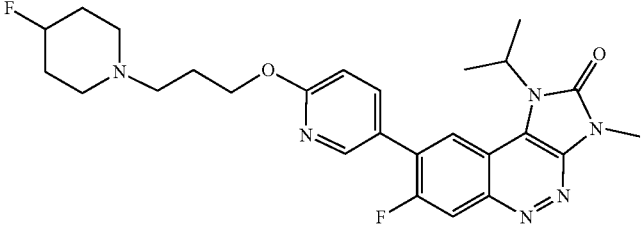 [SMILES: CC(C)n1c(=O)n(C)c2nnc3cc(F)c(-c4ccc(OCCCN5CCC(F)CC5)nc4)cc3c21]<br>7-fluoro-8-(6-(3-(4-fluoropiperidin-1-yl)propoxy)pyridin-3-yl)-1-isopropyl-3-methyl-1H-imidazo[4,5-c]cinnolin-2(3H)-one |
| 14 | 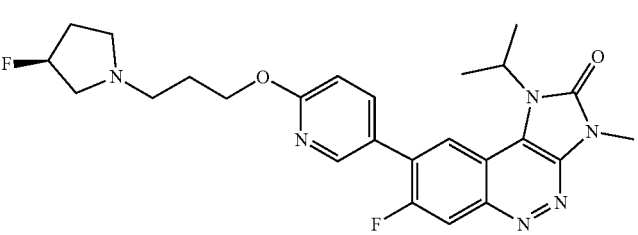 [SMILES: CC(C)n1c(=O)n(C)c2nnc3cc(F)c(-c4ccc(OCCCN5CC[C@H](F)C5)nc4)cc3c21]<br>(S)-7-fluoro-8-(6-(3-(3-fluoropyrrolidin-1-yl)propoxy)pyridin-3-yl)-1-isopropyl-3-methyl-1H-imidazo[4,5-c]cinnolin-2(3H)-one |
| 15 | 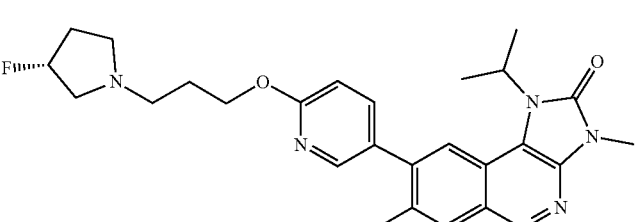<br>(R)-7-fluoro-8-(6-(3-(3-fluoropyrrolidin-1-yl)propoxy)pyridin-3-yl)-1-isopropyl-3-methyl-1H-imidazo[4,5-c]cinnolin-2(3H)-one |
| 16 | 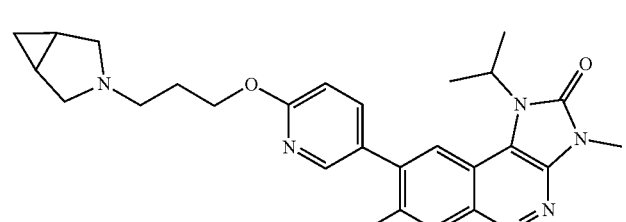<br>8-(6-(3-(3-azabicyclo[3.1.0]hexan-3-yl)propoxy)pyridin-3-yl)-7-fluoro-1-isopropyl-3-methyl-1H-imidazo[4,5-c]cinnolin-2(3H)-one |
| 17 | 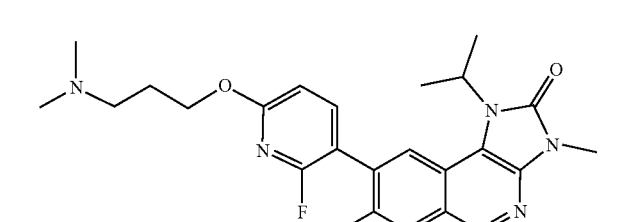<br>8-(6-(3-(dimethylamino)propoxy)-2-fluoropyridin-3-yl)-7-fluoro-1-isopropyl-3-methyl-1,3-dihydro-2H-imidazo[4,5-c]cinnolin-2-one |

TABLE 1-continued

| Cmpd No. | Compound Structure and Name |
|---|---|
| 18 | 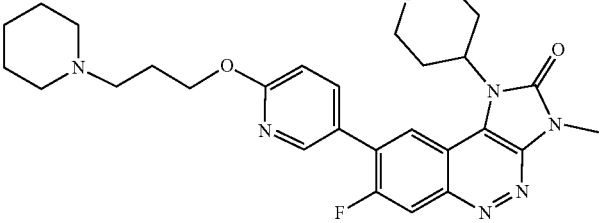<br>7-fluoro-3-methyl-8-(6-(3-(piperidin-1-yl)propoxy)pyridin-3-yl)-1-(tetrahydro-2H-pyran-4-yl)-1H-imidazo[4,5-c]cinnolin-2(3H)-one |
| 19 | 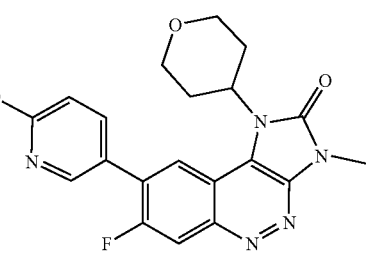<br>8-(6-(3-(dimethylamino)propoxy)pyridin-3-yl)-7-fluoro-3-methyl-1-(tetrahydro-2H-pyran-4-yl)-1H-imidazo[4,5-c]cinnolin-2(3H)-one |
| 20 | 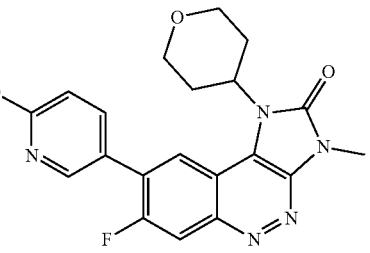<br>7-fluoro-3-methyl-8-(6-(3-(pyrrolidin-1-yl)propoxy)pyridin-3-yl)-1-(tetrahydro-2H-pyran-4-yl)-1H-imidazo[4,5-c]cinnolin-2(3H)-one |
| 21 | 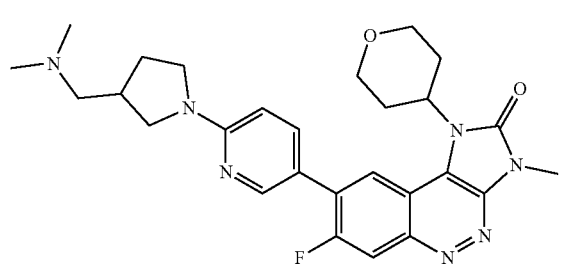<br>8-(6-(3-((dimethylamino)methyl)pyrrolidin-1-yl)pyridin-3-yl)-7-fluoro-3-methyl-1-(tetrahydro-2H-pyran-4-yl)-1H-imidazo[4,5-c]cinnolin-2(3H)-one |
| 22 | 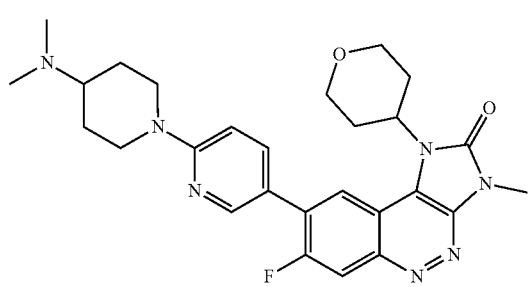<br>8-(6-(4-(dimethylamino)piperidin-1-yl)pyridin-3-yl)-7-fluoro-3-methyl-1-(tetrahydro-2H-pyran-4-yl)-1H-imidazo[4,5-c]cinnolin-2(3H)-one |

TABLE 1-continued

| Cmpd No. | Compound Structure and Name |
|---|---|
| 23 | 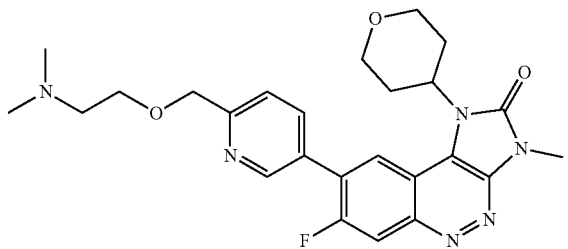<br>8-(6-((2-(dimethylamino)ethoxy)methyl)pyridin-3-yl)-7-fluoro-3-methyl-1-(tetrahydro-2H-pyran-4-yl)-1H-imidazo[4,5-c]cinnolin-2(3H)-one |
| 24 | 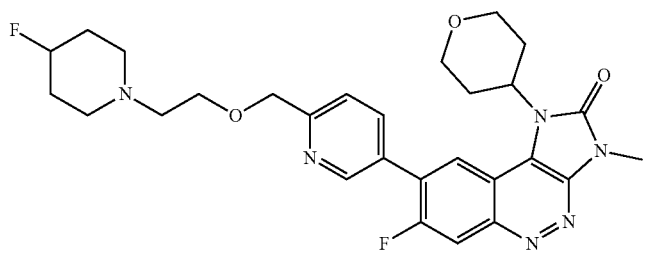 [SMILES: Cn1c(=O)n(C2CCOCC2)c2c3cc(-c4ccc(COCCN5CCC(F)CC5)nc4)c(F)cc3nnc21]<br>7-fluoro-8-(6-(3-(4-fluoropiperidin-1-yl)propoxy)pyridin-3-yl)-3-methyl-1-(tetrahydro-2H-pyran-4-yl)-1H-imidazo[4,5-c]cinnolin-2(3H)-one |
| 25 | 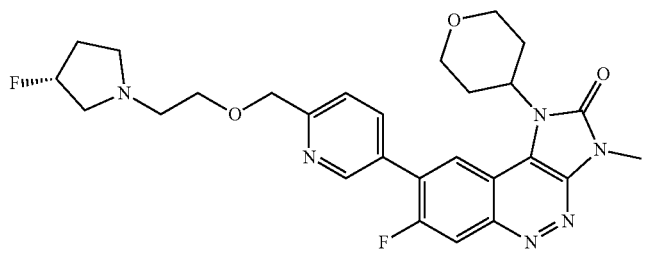 [SMILES: Cn1c(=O)n(C2CCOCC2)c2c3cc(-c4ccc(COCCN5CC[C@@H](F)C5)nc4)c(F)cc3nnc21]<br>(R)-7-fluoro-8-(6-(3-(3-fluoropyrrolidin-1-yl)propoxy)pyridin-3-yl)-3-methyl-1-(tetrahydro-2H-pyran-4-yl)-1H-imidazo[4,5-c]cinnolin-2(3H)-one |
| 26 | 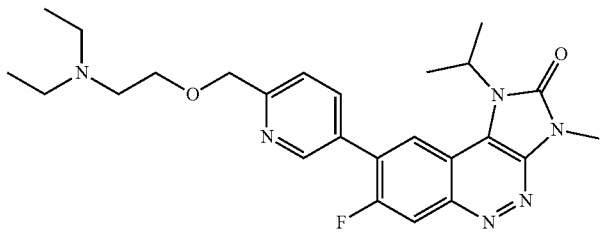 [SMILES: CCN(CC)CCOCc1ccc(-c2cc3c(cc2F)nnc2c3n(C(C)C)c(=O)n2C)cn1]<br>8-(6-((2-(diethylamino)ethoxy)methyl)pyridin-3-yl)-7-fluoro-1-isopropyl-3-methyl-1,3-dihydro-2H-imidazo[4,5-c]cinnolin-2-one |
| 27 | 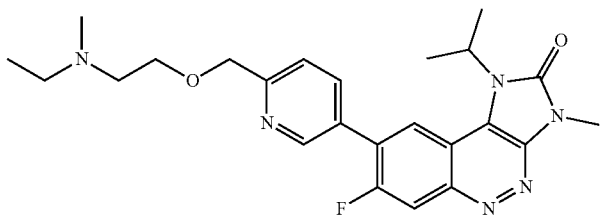 [SMILES: CCN(C)CCOCc1ccc(-c2cc3c(cc2F)nnc2c3n(C(C)C)c(=O)n2C)cn1]<br>8-(6-((2-(ethyl(methyl)amino)ethoxy)methyl)pyridin-3-yl)-7-fluoro-1-isopropyl-3-methyl-1,3-dihydro-2H-imidazo[4,5-c]cinnolin-2-one |

TABLE 1-continued

| Cmpd No. | Compound Structure and Name |
|---|---|
| 28 | 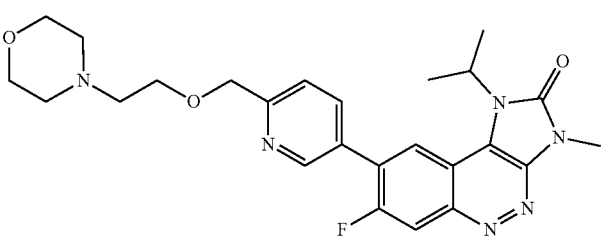 [SMILES: CC(C)n1c(=O)n(C)c2nnc3cc(F)c(-c4ccc(COCCN5CCOCC5)nc4)cc3c21]<br>7-fluoro-1-isopropyl-3-methyl-8-(6-((2-morpholinoethoxy)methyl)pyridin-3-yl)-1,3-dihydro-2H-imidazo[4,5-c]cinnolin-2-one |
| 29 | 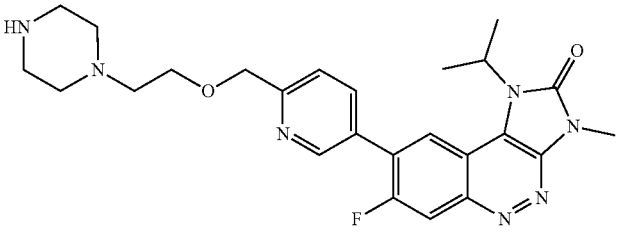 [SMILES: CC(C)n1c(=O)n(C)c2nnc3cc(F)c(-c4ccc(COCCN5CCNCC5)nc4)cc3c21]<br>7-fluoro-1-isopropyl-3-methyl-8-(6-((2-(piperazin-1-yl)ethoxy)methyl)pyridin-3-yl)-1,3-dihydro-2H-imidazo[4,5-c]cinnolin-2-one |
| 30 | 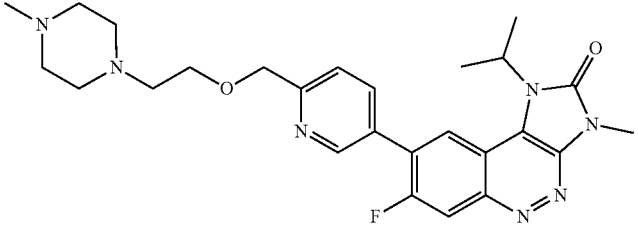<br>7-fluoro-1-isopropyl-3-methyl-8-(6-((2-(4-methylpiperazin-1-yl)ethoxy)methyl)pyridin-3-yl)-1,3-dihydro-2H-imidazo[4,5-c]cinnolin-2-one |
| 31 | 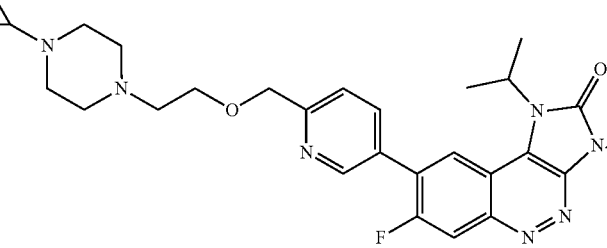<br>8-(6-((2-(4-cyclopropylpiperazin-1-yl)ethoxy)methyl)pyridin-3-yl)-7-fluoro-1-isopropyl-3-methyl-1,3-dihydro-2H-imidazo[4,5-c]cinnolin-2-one |
| 32 | 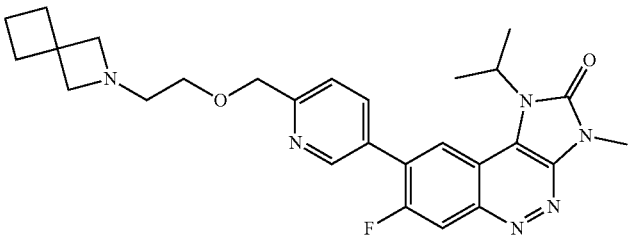 [SMILES: CC(C)n1c(=O)n(C)c2nnc3cc(F)c(-c4ccc(COCCN5CC6(CCC6)C5)nc4)cc3c21]<br>8-(6-((2-(2-azaspiro[3.3]heptan-2-yl)ethoxy)methyl)pyridin-3-yl)-7-fluoro-1-isopropyl-3-methyl-1,3-dihydro-2H-imidazo[4,5-c]cinnolin-2-one |

TABLE 1-continued

| Cmpd No. | Compound Structure and Name |
|---|---|
| 33 | 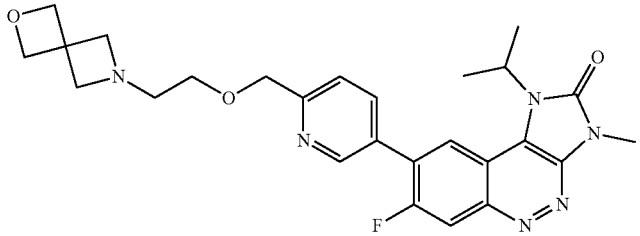 [SMILES: CC(C)n1c(=O)n(C)c2nnc3cc(F)c(-c4ccc(COCCN5CC6(COC6)C5)nc4)cc3c21]<br>8-(6-((2-(2-oxa-6-azaspiro[3.3]heptan-6-yl)ethoxy)methyl)pyridin-3-yl)-7-fluoro-1-isopropyl-3-methyl-1,3-dihydro-2H-imidazo[4,5-c]cinnolin-2-one |
| 34 | 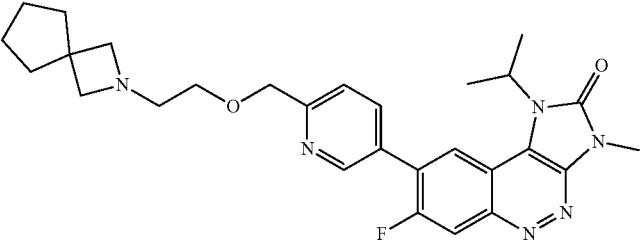 [SMILES: CC(C)n1c(=O)n(C)c2nnc3cc(F)c(-c4ccc(COCCN5CC6(CCCC6)C5)nc4)cc3c21]<br>8-(6-((2-(2-azaspiro[3.4]octan-2-yl)ethoxy)methyl)pyridin-3-yl)-7-fluoro-1-isopropyl-3-methyl-1,3-dihydro-2H-imidazo[4,5-c]cinnolin-2-one |
| 35 | 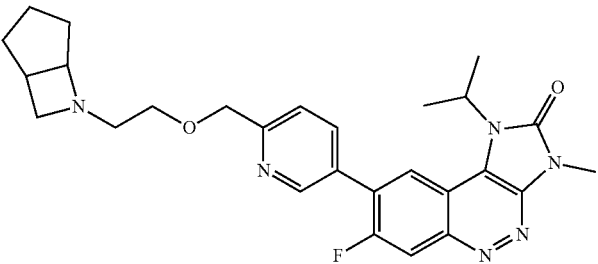 [SMILES: CC(C)n1c(=O)n(C)c2nnc3cc(F)c(-c4ccc(COCCN5CC6CCCC65)nc4)cc3c21]<br>8-(6-((2-(6-azabicyclo[3.2.0]heptan-6-yl)ethoxy)methyl)pyridin-3-yl)-7-fluoro-1-isopropyl-3-methyl-1,3-dihydro-2H-imidazo[4,5-c]cinnolin-2-one |
| 36 | 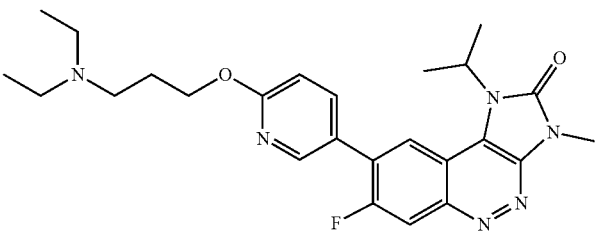 [SMILES: CCN(CC)CCCOc1ccc(-c2cc3c(cc2F)nnc2c3n(C(C)C)c(=O)n2C)cn1]<br>8-(6-(3-(diethylamino)propoxy)pyridin-3-yl)-7-fluoro-1-isopropyl-3-methyl-1,3-dihydro-2H-imidazo[4,5-c]cinnolin-2-one |
| 37 | 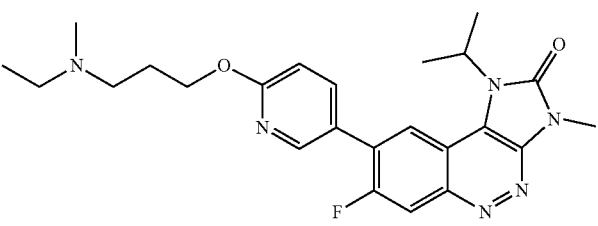 [SMILES: CCN(C)CCCOc1ccc(-c2cc3c(cc2F)nnc2c3n(C(C)C)c(=O)n2C)cn1]<br>8-(6-(3-(ethyl(methyl)amino)propoxy)pyridin-3-yl)-7-fluoro-1-isopropyl-3-methyl-1,3-dihydro-2H-imidazo[4,5-c]cinnolin-2-one |

TABLE 1-continued

| Cmpd No. | Compound Structure and Name |
|---|---|
| 38 | 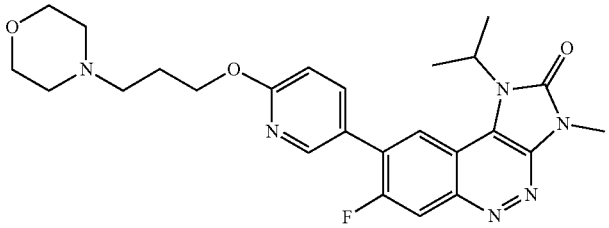 [SMILES: CC(C)n1c(=O)n(C)c2nnc3cc(F)c(-c4ccc(OCCCN5CCOCC5)nc4)cc3c21]<br>7-fluoro-1-isopropyl-3-methyl-8-(6-(3-morpholinopropoxy)pyridin-3-yl)-1,3-dihydro-2H-imidazo[4,5-c]cinnolin-2-one |
| 39 | 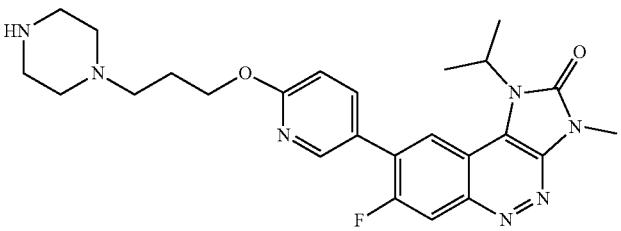 [SMILES: CC(C)n1c(=O)n(C)c2nnc3cc(F)c(-c4ccc(OCCCN5CCNCC5)nc4)cc3c21]<br>7-fluoro-1-isopropyl-3-methyl-8-(6-(3-(piperazin-1-yl)propoxy)pyridin-3-yl)-1,3-dihydro-2H-imidazo[4,5-c]cinnolin-2-one |
| 40 | 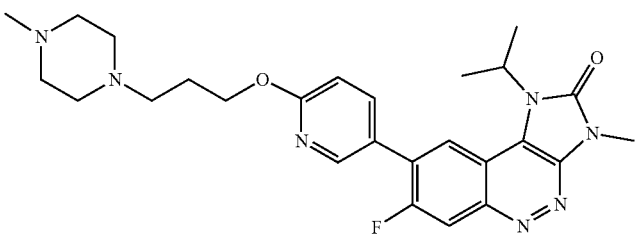<br>7-fluoro-1-isopropyl-3-methyl-8-(6-(3-(4-methylpiperazin-1-yl)propoxy)pyridin-3-yl)-1,3-dihydro-2H-imidazo[4,5-c]cinnolin-2-one |
| 41 | 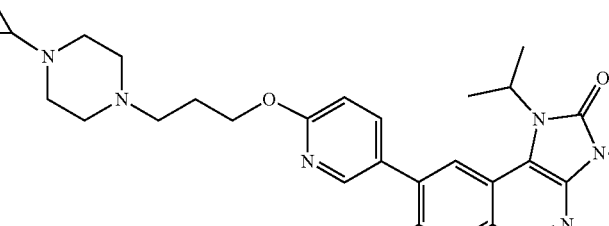<br>8-(6-(3-(4-cyclopropylpiperazin-1-yl)propoxy)pyridin-3-yl)-7-fluoro-1-isopropyl-3-methyl-1,3-dihydro-2H-imidazo[4,5-c]cinnolin-2-one |
| 42 | 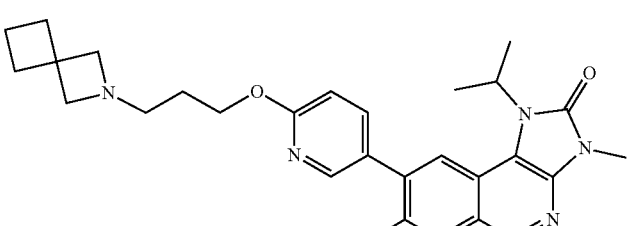<br>8-(6-(3-(2-azaspiro[3.3]heptan-2-yl)propoxy)pyridin-3-yl)-7-fluoro-1-isopropyl-3-methyl-1,3-dihydro-2H-imidazo[4,5-c]cinnolin-2-one |

TABLE 1-continued

| Cmpd No. | Compound Structure and Name |
|---|---|
| 43 | 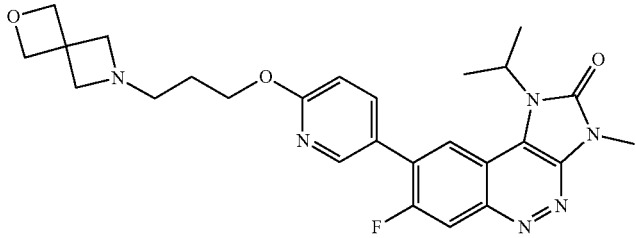 [SMILES: CC(C)n1c(=O)n(C)c2nnc3cc(F)c(-c4ccc(OCCCN5CC6(COC6)C5)nc4)cc3c21]<br>8-(6-(3-(2-oxa-6-azaspiro[3.3]heptan-6-yl)propoxy)pyridin-3-yl)-7-fluoro-1-isopropyl-3-methyl-1,3-dihydro-2H-imidazo[4,5-c]cinnolin-2-one |
| 44 | 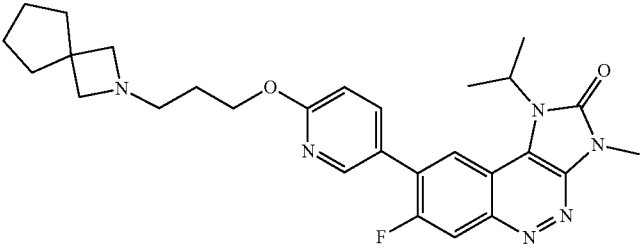 [SMILES: CC(C)n1c(=O)n(C)c2nnc3cc(F)c(-c4ccc(OCCCN5CC6(CCCC6)C5)nc4)cc3c21]<br>8-(6-(3-(2-azaspiro[3.4]octan-2-yl)propoxy)pyridin-3-yl)-7-fluoro-1-isopropyl-3-methyl-1,3-dihydro-2H-imidazo[4,5-c]cinnolin-2-one |
| 45 | 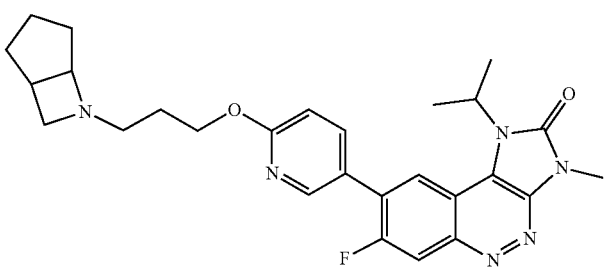 [SMILES: CC(C)n1c(=O)n(C)c2nnc3cc(F)c(-c4ccc(OCCCN5CC6CCCC65)nc4)cc3c21]<br>8-(6-(3-(6-azabicyclo[3.2.0]heptan-6-yl)propoxy)pyridin-3-yl)-7-fluoro-1-isopropyl-3-methyl-1,3-dihydro-2H-imidazo[4,5-c]cinnolin-2-one |

Compounds provided herein are described with reference to both generic formulae and specific compounds. In addition, compounds of the present disclosure may exist in a number of different forms or derivatives, all within the scope of the present disclosure. These include, for example, tautomers, stereoisomers, racemic mixtures, regioisomers, salts, prodrugs, solvated forms, different crystal forms or polymorphs, and active metabolites.

The compounds of present disclosure can comprise one or more asymmetric centers, and thus can exist in various stereoisomeric forms, e.g., enantiomers and/or diastereomers. Thus, inventive compounds and compositions thereof may be in the form of an individual enantiomer, diastereomer or geometric isomer, or may be in the form of a mixture of stereoisomers. In certain embodiments, the compounds of the present disclosure are enantiopure compounds. In certain embodiments, mixtures of enantiomers or diastereomers are provided.

The term "enantiomer" refers to two stereoisomers of a compound which are non-superimposable mirror images of one another. The term "diastereomer" refers to a pair of optical isomers which are not mirror images of one another. Diastereomers have different physical properties, e.g. melting points, boiling points, spectral properties, and reactivities.

Furthermore, certain compounds, as described herein may have one or more double bonds that can exist as either the Z or E isomer, unless otherwise indicated. The present disclosure additionally encompasses the compounds as individual isomers substantially free of other isomers and alternatively, as mixtures of various isomers, e.g., racemic mixtures of enantiomers. In addition to the above-mentioned compounds per se, this disclosure also encompasses compositions comprising one or more compounds.

As used herein, the term "isomers" includes any and all geometric isomers and stereoisomers. For example, "isomers" include cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, a stereoisomer may, in some embodiments, be provided substantially free of one or more corresponding stereoisomers, and may also be referred to as "stereochemically enriched".

Where a particular enantiomer is preferred, it may, in some embodiments be provided substantially free of the opposite enantiomer, and may also be referred to as "optically enriched". "Optically enriched", as used herein, means that the compound is made up of a significantly greater proportion of one enantiomer. In certain embodiments, the compound is made up of at least about 90% by weight of a preferred enantiomer. In other embodiments, the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, N Y, 1962); Wilen, S. H. Tables of Resolving Agents and Optical Resolutions p. 268 (E. L. Eliel, Ed., Univ. of Notre Dame Press, Notre Dame, Ind. 1972).

The compounds of the present disclosure may also exist in different tautomeric forms, and all such forms are embraced within the scope of the present disclosure. The term "tautomer" or "tautomeric form" refers to structural isomers of different energies which are interconvertible via a low energy barrier. For example, proton tautomers (also known as prototropic tautomers) include interconversions via migration of a proton, such as keto-enol, amide-imidic acid, lactam-lactim, imine-enamine isomerizations and annular forms where a proton can occupy two or more positions of a heterocyclic system (for example, 1H- and 3H-imidazole, 1H-, 2H- and 4H-1,2,4-triazole, 1H- and 2H-isoindole, and 1H- and 2H-pyrazole). Valence tautomers include interconversions by reorganization of some of the bonding electrons. Tautomers can be in equilibrium or sterically locked into one form by appropriate substitution. Compounds of the present disclosure identified by name or structure as one particular tautomeric form are intended to include other tautomeric forms unless otherwise specified.

The compounds of the present disclosure also include prodrugs, active metabolic derivatives (active metabolites), active intermediates, and their pharmaceutically acceptable salts.

As used herein, the term "prodrugs" refers to compounds or pharmaceutically acceptable salts thereof which, when metabolized under physiological conditions or when converted by solvolysis, yield the desired active compound. Prodrugs include, without limitation, esters, amides, carbamates, carbonates, ureides, solvates, or hydrates of the active compound. Typically, the prodrug is inactive, or less active than the active compound, but may provide one or more advantageous handling, administration, and/or metabolic properties. For example, some prodrugs are esters of the active compound; during metabolysis, the ester group is cleaved to yield the active drug. Also, some prodrugs are activated enzymatically to yield the active compound, or a compound which, upon further chemical reaction, yields the active compound. Prodrugs may proceed from prodrug form to active form in a single step or may have one or more intermediate forms which may themselves have activity or may be inactive. Preparation and use of prodrugs is discussed in T. Higuchi and V. Stella, "Pro-drugs as Novel Delivery Systems", Vol. 14 of the A.C.S. Symposium Series, and in Bioreversible Carriers in Drug Design, ed. Edward B. Roche, American Pharmaceutical Association and Pergamon Press, 1987, both of which are hereby incorporated by reference in their entirety.

As used herein, the term "metabolite", e.g., active metabolite overlaps with prodrug as described above. Thus, such metabolites are pharmacologically active compounds or compounds that further metabolize to pharmacologically active compounds that are derivatives resulting from metabolic process in the body of a subject. For example, such metabolites may result from oxidation, reduction, hydrolysis, amidation, deamidation, esterification, deesterification, enzymatic cleavage, and the like, of the administered compound or salt or prodrug. Of these, active metabolites are such pharmacologically active derivative compounds. For prodrugs, the prodrug compound is generally inactive or of lower activity than the metabolic product. For active metabolites, the parent compound may be either an active compound or may be an inactive prodrug.

Prodrugs and active metabolites may be identified using routine techniques know in the art. See, e.g., Bertolini et al, 1997, J Med Chem 40:2011-2016; Shan et al., J Pharm Sci 86:756-757; Bagshawe, 1995, Drug Dev Res 34:220-230; Wermuth, supra.

As used herein, the term "active intermediate" refers to intermediate compound in the synthetic process, which exhibits the same or essentially the same biological activity as the final synthesized compound.

Compounds of the present disclosure can be formulated as or be in the form of pharmaceutically acceptable salts. Unless specified to the contrary, a compound provided herein includes pharmaceutically acceptable salts of such compound.

As used herein, the term "pharmaceutically acceptable" indicates that the substance or composition is compatible chemically and/or toxicologically, with the other ingredients comprising a formulation, and/or the subjects being treated therewith.

As used herein, the term "pharmaceutically acceptable salt", unless otherwise indicated, includes salts that retain the biological effectiveness of the free acids and bases of the specified compound and that are not biologically or otherwise undesirable. Contemplated pharmaceutically acceptable salt forms include, but are not limited to, mono, bis, tris, tetrakis, and so on. Pharmaceutically acceptable salts are non-toxic in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering higher concentrations of the drug.

Pharmaceutically acceptable salts include acid addition salts such as those containing sulfate, chloride, hydrochloride, fumarate, maleate, phosphate, sulfamate, acetate, citrate, lactate, tartrate, methanesulfonate, ethanesulfonate, benzenesulfonate, p-toluenesulfonate, cyclohexyl sulfamate and quinate. Pharmaceutically acceptable salts can be obtained from acids such as hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexyl sulfamic acid, fumaric acid, and quinic acid.

Pharmaceutically acceptable salts also include basic addition salts such as those containing benzathine, chloroprocaine, choline, diethanolamine, ethanolamine, t-butylamine, ethylenediamine, meglumine, procaine, aluminum, calcium, lithium, magnesium, potassium, sodium, ammonium, alkylamine, and zinc, when acidic functional groups, such as carboxylic acid or phenol are present. For example, see Remington's Pharmaceutical Sciences, 19$^{th}$ ed., Mack Publishing Co., Easton, Pa., Vol. 2, p. 1457, 1995; "Handbook of Pharmaceutical Salts: Properties, Selection, and Use" by Stahl and Wermuth, Wiley-VCH, Weinheim, Germany, 2002. Such salts can be prepared using the appropriate corresponding bases.

Pharmaceutically acceptable salts can be prepared by standard techniques. For example, the free-base form of a compound can be dissolved in a suitable solvent, such as an aqueous or aqueous-alcohol solution containing the appropriate acid and then isolated by evaporating the solution. Thus, if the particular compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

Similarly, if the particular compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as L-glycine, L-lysine, and L-arginine, ammonia, primary, secondary, and tertiary amines, and cyclic amines, such as hydroxyethylpyrrolidine, piperidine, morpholine or piperazine, and inorganic salts derived from sodium, calcium, potassium, magnesium, manganese, iron, copper, zinc, aluminum and lithium.

It is also to be understood that the compounds of present disclosure can exist in unsolvated forms, solvated forms (e.g., hydrated forms), and solid forms (e.g., crystal or polymorphic forms), and the present disclosure is intended to encompass all such forms.

As used herein, the term "solvate" or "solvated form" refers to solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the terms "crystal form", "crystalline form", "polymorphic forms" and "polymorphs" can be used interchangeably, and mean crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The present disclosure is also intended to include include all isotopes of atoms in the compounds. Isotopes of an atom include atoms having the same atomic number but different mass numbers. For example, unless otherwise specified, hydrogen, carbon, nitrogen, oxygen, phosphorous, sulphur, fluorine, chlorine, bromide or iodine in the compounds of present disclosure are meant to also include their isotopes, such as but not limited to $^{1}H$, $^{2}H$, $^{3}H$, $^{11}C$, $^{12}C$, $^{13}C$, $^{11}C$, $^{14}N$, $^{15}N$, $^{16}O$, $^{17}O$, $^{18}O$, $^{31}P$, $^{32}P$, $^{32}S$, $^{33}S$, $^{34}S$, $^{36}S$, $^{17}F$, $^{19}F$, $^{35}Cl$, $^{37}Cl$, $^{79}Br$, $^{81}Br$, $^{127}I$ and $^{131}I$. In some embodiments, hydrogen includes protium, deuterium and tritium. In some embodiments, carbon includes $^{12}C$ and $^{13}C$.

Synthesis of the Compounds

Synthesis of the compounds provided herein, including pharmaceutically acceptable salts thereof, are illustrated in the synthetic schemes in the examples. The compounds provided herein can be prepared using any known organic synthesis techniques and can be synthesized according to any of numerous possible synthetic routes, and thus these schemes are illustrative only and are not meant to limit other possible methods that can be used to prepare the compounds provided herein. Additionally, the steps in the Schemes are for better illustration and can be changed as appropriate. The embodiments of the compounds in examples were synthesized for the purposes of research and potentially submission to regulatory agencies.

The reactions for preparing compounds of the present disclosure can be carried out in suitable solvents, which can be readily selected by one skilled in the art of organic synthesis. Suitable solvents can be substantially non-reactive with the starting materials (reactants), the intermediates, or products at the temperatures at which the reactions are carried out, e.g. temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected by one skilled in the art.

Preparation of compounds of the present disclosure can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, Protective Groups in Organic Synthesis, 3rd Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g. $^{1}H$ or $^{13}C$), infrared spectroscopy, spectrophotometry (e.g. UV-visible), mass spectrometry, or by chromatographic methods such as high performance liquid chromatography (HPLC), liquid chromatography-mass spectroscopy (LCMS), or thin layer chromatography (TLC). Compounds can be purified by one skilled in the art by a variety of methods, including high performance liquid chromatography (HPLC) ("Preparative LC-MS Purification: Improved Compound Specific Method Optimization" Karl F. Blom, Brian Glass, Richard Sparks, Andrew P. Combs J. Combi. Chem. 2004, 6(6), 874-883, which is incorporated herein by reference in its entirety), and normal phase silica chromatography.

The structures of the compounds in the examples are characterized by nuclear magnetic resonance (NMR) or/and liquid chromatography-mass spectrometry (LC-MS). NMR chemical shift (δ) is given in the unit of $10^{-6}$ (ppm). $^{1}H$-NMR spectra is recorded in $CDCl_3$, $CD_3OD$ or DMSO- $d_6$ solutions (reported in ppm) on a Varian instrument (400 MHz), using tetramethylsilane (TMS) as the reference standard (0.0 ppm).

MS measurement is carried out using Shimadzu 2010 Mass Spectrometer or Agilent 6110A MSD or 1969A TOF mass spectrometer using electrospray, chemical and electron impact ionization methods from a range of instruments.

TLC measurement is carried out using Yantai Huanghai HSGF254 silica gel or Anhui Liang Chen Gui Yuan plates. The silica gel plates used for TLC are 0.15 mm~0.2 mm. The silica gel plates used for separating and purifying products by TLC are 0.4 mm~0.5 mm.

Column chromatography was done on a Biotage system (Manufacturer: Dyax Corporation) having a silica gel column or on a silica SepPak cartridge (Waters).

The known starting materials of the present disclosure can be synthesized by using or according to the known methods in the art, or can be purchased from commercial suppliers such as Aldrich Chemical Company, Adamas-beta, TCI or Accela ChemBio Co., Ltd, and were used without further purification unless otherwise indicated. Tetrahydrofuran (THF), N,N-dimethylformamide (DMF), dichloromethane (DCM), dichloroethane (DCE), dioxane and 1,1,2,2-tetrachloroethane were purchased from Aldrich in Sure seal bottles and used as received.

Unless otherwise specified, the reactions of the present disclosure were all done under a positive pressure of nitrogen or argon or with a drying tube in anhydrous solvents, and the reaction flasks were typically fitted with rubber septa for the introduction of substrates and reagents via syringe. Glassware was oven dried and/or heat dried.

For illustrative purposes, the following shows general synthetic route for preparing the compounds of the present disclosure as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

General Synthetic Route

In some embodiments, compounds of Formula (I) may be prepared by the reaction of a compound of Formula (IIa) or (IIb).

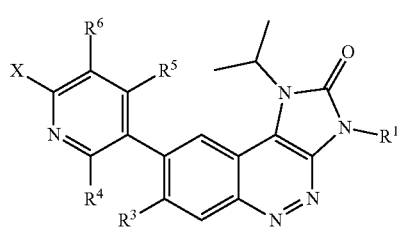

IIa

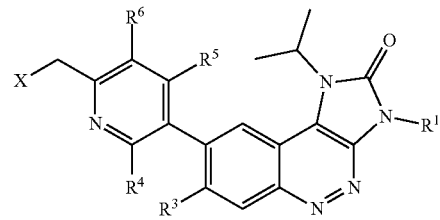

IIb wherein X is a leaving group (for example a halogen atom such as a fluorine atom) with a compound of formula (IIIa) or (IIIb):

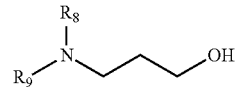

IIIa

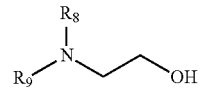

IIIb or a salt thereof. The reaction is conveniently performed in a suitable solvent (for example DMF or THF) and in the presence of a base (for example sodium hydride or t-BuOK) at a suitable temperature (for example a temperature in the range of about 20-100° C.).

In some embodiments, compounds of Formula (I) may be prepared by the reaction of a compound of Formula IIa with IIIc:

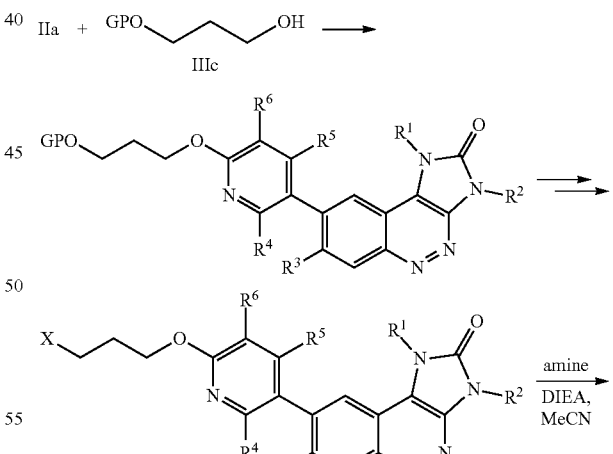

wherein PG is the proper protecting groups (for example, THP) and cleaved in acid condition (for example PTSA) and then followed by the conversion into a good leaving group X (for example mesylate or tosylate), which was finally reacted with variant amines in the presence of a base (triethylamime or DIEA) to obtain Formula (I).

Compounds of Formula (IIa) and (IIb) may be prepared by the reaction of a compound of Formula (IV):

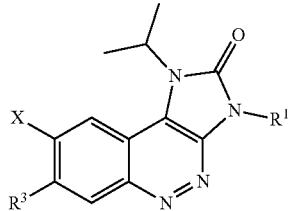

(IV)

wherein X is a leaving group (for example a halogen atom such as a chlorine, an iodine, or a bromine atom, or a triflate group) with a compound of formula (Va) or (Vb):

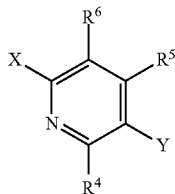

Va

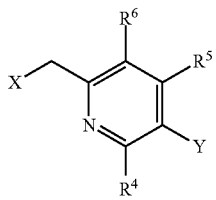

Vb or a salt thereof, where X is a leaving group (for example a halogen atom such as a chlorine, an iodine, or a bromine atom, or a triflate group), and Y is a boronic acid, boronic ester (e.g., boronic acid pinacol ester) or potassium trifluoroborate group. The reaction may be performed under standard conditions well known to those skilled in the art, for example in the presence of a palladium source (e.g., tetrakis triphenylphosphine palladium or palladium(II) acetate), optionally a phosphine ligand (e.g., Xantphos or S-phos), and a suitable base (e.g., cesium carbonate or triethylamine).

Compounds of formula (IV) can be prepared by methods similar to those shown in the Examples section.

In some embodiments, compounds of Formula (I) may also be prepared by the reaction of a compound of Formula (IV) with a compound of formula (VIa) or (VIb):

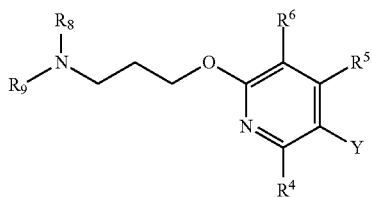

VIa

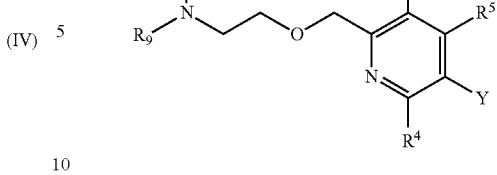

VIb wherein Y is a boronic acid, boronic ester (e.g., boronic acid pinacol ester) or potassium trifluoroborate group. The reaction may be performed under standard conditions well known to those skilled in the art, for example in the presence of a palladium source (e.g., tetrakis triphenylphosphine palladium or palladium(II) acetate), optionally a phosphine ligand (e.g., Xantphos or S-phos), and a suitable base (e.g., cesium carbonate or triethylamine).

Compounds of formula (VIa) or (VIb) can be prepared by methods similar to those shown in the Examples section.

Use of Compounds

In an aspect, the present disclosure provides compounds of formula (I) or pharmaceutically acceptable salts thereof, which show ATM kinase inhibitory activity.

As used herein, the term "ATM kinase inhibitory activity" refers to a decrease in the activity of ATM kinase as a direct or indirect response to the presence of a compound of Formula (I), or pharmaceutically acceptable salt thereof, relative to the activity of ATM kinase in the absence of compound of Formula (I), or pharmaceutically acceptable salt thereof. Such a decrease in activity may be due to the direct interaction of the compound of Formula (I), or pharmaceutically acceptable salt thereof with ATM kinase, or due to the interaction of the compound of Formula (I), or pharmaceutically acceptable salt thereof with one or more other factors that in turn affect ATM kinase activity. For example, the compound of Formula (I), or pharmaceutically acceptable salt thereof may decrease ATM kinase by directly binding to the ATM kinase, by causing (directly or indirectly) another factor to decrease ATM kinase activity, or by (directly or indirectly) decreasing the amount of ATM kinase present in the cell or organism.

In some embodiments, the compounds of the present disclosure are selective inhibitors of ATM kinase.

As used herein, the term "selective inhibitor" or "selectively inhibits" means that a provided compound inhibits ATM kinase in at least one assay described herein (e.g., biochemical or cellular). In some embodiments, the term "selective inhibitor" or "selectively inhibits" means that a provided compound has the $IC_{50}$ for inhibiting the enzymes in PIKK family closely related to ATM kinase (such as PI3K, mTOR and ATR) at least 5000 fold higher, at least 4000 fold higher, at least 3000 fold higher, at least 2000 fold higher, at least 1000 fold higher, at least 500 fold higher, at least 400 fold higher, at least 300 fold higher, at least 200 fold higher, at least 100 fold higher, at least 90 fold higher, at least 80 fold higher, at least 70 fold higher, at least 60 fold higher, at least 50 fold higher, at least 40 fold higher, at least 30 fold higher, at least 20 fold higher, at least 10 fold higher, than the $IC_{50}$ for inhibiting ATM kinase.

In some embodiments, the compounds of the present disclosure are not AO substrates, as determined in human liver cytosol.

As used herein, the term "AO substrate" means that a given compound is susceptible to oxidation by aldehyde oxidase ("AO") and thus highly susceptible to AO mediated clearance. In some embodiments, the AO susceptibility of a compound can be evaluated by intrinsic clearance ($CL_{int}$) in human liver cytosol system (Zientek M. et al, *Drug Metab Dispos*, 2010, 1322-27), as described in detail in Example section below. Human liver cytosol system useful in the evaluation is commercially available, for example, from Xenotech with catalog number H0606.C (AX) and lot number 1710130. In general, human liver cytosolic extracts can be prepared by ultra-centrifugation of liver homogenates obtained from human donors. In certain embodiments, the human liver cytosolic extracts (e.g. H0606.C (AX) from Xenotech) can be made specifically from donors with high AO activity to minimize under prediction of AO mediated clearance. In some embodiments, PF-04217903 (2-[4-[3-(quinolin-6-ylmethyl)triazolo[4,5-b]pyrazin-5-yl]pyrazol-1-yl]ethanol, reported as a weak AO substrate) and Zaleplon (N-[3-(3-cyanopyrazolo[1,5-a]pyrimidin-7-yl)phenyl]-N-ethylacetamide, considered as a strong AO substrate) are both used as references in human liver cytosolic system. In certain embodiments, a compound will not be considered as an AO substrate if the compound shows an $CL_{int}$ lower than that of PF-04217903 (1.8 µL/min/mg protein), while a compound will be considered as a strong AO substrate if the compound shows an $CL_{int}$ higher than that of Zaleplon (3.1 µL/min/mg protein), wherein the $CL_{int}$ is determined by the AO assay described in the AO assay described in Example section below.

In some embodiments, the compounds of the present disclosure show low AO susceptibility with a $CL_{int}$ in human hepatocyte of less than about 1.8 µL/min/mg protein, 1.7 µL/min/mg protein, 1.6 µL/min/mg protein, 1.5 µL/min/mg protein, 1.4 µL/min/mg protein, 1.3 µL/min/mg protein, 1.2 µL/min/mg protein, 1.1 µL/min/mg protein, 1 µL/min/mg protein, 0.9 µL/min/mg protein, 0.8 µL/min/mg protein, 0.7 µL/min/mg protein, 0.6 µL/min/mg protein, 0.5 µL/min/mg protein, 0.4 µL/min/mg protein, 0.3 µL/min/mg protein, 0.2 µL/min/mg protein, or 0.1 µL/min/mg protein.

AOs are cytosolic molybdo-flavoenzymes, a group of proteins that require a flavin adenine dinucleotide (FAD) and a molybdopterin [molybdenum cofactor (MoCo)] for their catalytic activity. AOs oxidize aromatic aldehydes into the corresponding carboxylic acids and heterocycles into hydroxylated derivatives. The potential of AO to oxidize heterocycles is of particular importance in the context of drug design and development, as these chemical groups are popular synthetic blocks in medicinal chemistry. AO mediated metabolism is often overlooked during drug discovery stage, and high clearance issue is not revealed until in phase 1 clinical trial. AO is a cytosolic enzyme and thus its potential contribution to the metabolic clearance of new compounds is not addressed in standard metabolic stability screens using liver microsomes. Hepatocytes are a whole cell system which contains both microsomes and cytosol. However, AO is an unstable protein with substantial loss in activity during hepatocytes preparation (Hutzler, J. M. et al., *Drug Metab Dispos*, 2014, 1090-7). In vivo studies on AO mediated metabolism in animal models are also highly problematic, as the components liver AOs in humans and in popular experimental animals are different (Garattini, E. et al., *Expert Opin Drug Discovery*, 2013, 641-54). Human liver is characterized by a single and active AO isozyme, that is, AOX1. The predominant AOX form expressed in many mouse and rat strains is AOX3. Two other experimental animals, cats and dogs, are characterized by absence of AO enzymatic activity. AO activity has been found to be much more active in higher primates (humans and monkeys) compared to rodents. AO is very concentrated in the liver, where it oxidizes multiple aldehydes and nitrogenous heterocyclic compounds, such as anti-cancer and immunosuppressive drugs (see, for example, Gordon A H, Green D E, Subrahmanyan, "Liver aldehyde oxidase", *The Biochemical Journal*. 1940, 34(5): 764-74). Human liver cytosolic extracts, which contain AO, but not significant amount of contaminating CYP450, has been shown to be a valuable tool to predict in vivo clearance mediated by human AO. Human liver cytosol purchased from Xenotech was used immediately after thawing, and not reused as AO is an unstable enzyme and becomes rapidly inactivated upon freezing-thawing. In light of highly variable AO activity, a high activity lot of human liver cytosol, was chosen for AO assay to minimize underprediction of clearance. Reference compounds Zaleplon (high clearance by AO) and PF-04217903 (low clearance by AO) were used as controls in the AO assay.

Without wishing to be bound by any particular theory, it is believed that AO has a significant impact on pharmacokinetics. AO is capable of oxidizing many drugs in the liver, because of its broad substrate specificity (Strelevitz T J, Orozco C C, Obach R S. "Hydralazine as a selective probe inactivator of aldehyde oxidase in human hepatocytes: estimation of the contribution of aldehyde oxidase to metabolic clearance". Drug Metabolism and Disposition. 2012, 40 (7): 1441-8). AO greatly contributes to the hepatic clearance of drugs and other compounds (Hartmann T, Terao M, Garattini E, Teutloff C, Alfaro J F, Jones J P, Leimkühler S. "The impact of single nucleotide polymorphisms on human aldehyde oxidase", *Drug Metabolism and Disposition*. 2012, 40 (5): 856-64). AO mediated metabolism tends to lead to high clearance in humans. For high clearance compounds, small change in intrinsic clearance due to different enzyme expression level among patients causes large change of bioavailability. The human AOX1 is highly polymorphic and some inactivating missense as well as nonsense polymorphic sites have been described in the human population (Garattini, E. et al, *Expert Opin Drug Discovery*, 2012, 487-503; Hartmann, T. et al, *Drug Metab Dispos*, 2012, 856-64). Such polymorphism results in reduced levels of the encoded AOX1 protein and explains the reported interindividual variability in AOX activity. Additionally many factors may affect AO activity, such as gender, age, cigarette smoking, drug usage, and disease states. Therefore, compounds with AO mediated high clearance have large inter-patients PK variability which results in unexpected toxicities in some individuals whereas efficacy is not achieved in other patients (Garattini, E. et al, *Expert Opin Drug Discovery*, 2013, 641-54; Hutzler, J. M. et al, *Drug Metab Dispos* 2014, 1090-7).

In contrast to the previously reported ATM inhibitors AZD0156 and AZD1390 that are strong AO substrate, the compounds of the present disclosure have surprisingly low susceptibility to AO oxidation. Therefore, in one aspect, the compounds and pharmaceutically acceptable salts thereof provided herein are not AO substrates, and consequently show better PK profile than compounds that are AO substrates. For example, the compounds provided herein have low PK variability, among humans that have different levels of AO activity.

In some embodiments, the compounds of the present disclosure are not P-glycoprotein (Pgp) substrates, nor ATP-binding cassette sub-family G member 2 (ABCG2, or BCRP) substrates. As used herein, the term "Pgp substrate" means that a given compound is susceptible to transporation back into the intestinal lumen (in the case of Pgp distributed in intestinal epithelium), bile ducts (in the case of Pgp distributed in liver cells), urinar filtrate (in the case of Pgp distributed in the cells of the proximal tubule of the kidney), capillaries (in the case of Pgp distributed in the capillary endothelial cells composing the blood-brain barrier and blood-testis barrier) and the like, by Pgp. As used herein, the term "BCRP substrate" means that a given compound is blocked from being absorption at the apical membrane of the intestine, the blood-testis barrier, the blood-brain barrier, and the membranes of hematopoietic progenitor and other stem cells, in particular the blood-brain barrier, by BCRP. Therefore, there is provided compounds or pharmaceutically acceptable salts thereof, which demonstrate good brain penetration in subjects, allowing for applications in treating both extracranial cancers and metastatic cancer, such as brain metastases.

In some embodiments, the Pgp and BCRP susceptibility of a compound can be evaluated by MDCK-MDR1 Pgp permeability assay and Caco-2 BCRP permeability assay, respectively, as described in detail in Example section below. In some embodiments, the compounds of the present disclosure show no Pgp susceptibility with a MDCK-Pgp efflux ratio (MDCK-Pgp ER) of less than about 2.5.

In some embodiments, the compounds of the present disclosure are capable of crossing blood-brain barrier (BBB) without the need of an agent to facilitate BBB entry.

In some embodiments, the compounds of the present disclosure show low hERG inhibition, as determined by hEGR inhibition assay described in detail in Example section below. In some embodiments, the compounds of the present disclosure show a hERG inhibition at 10 µM is less than 70%, less than 65%, less than 60%, less than 55%, less than 50%, less than 45%, less than 40%, less than 35%, less than 30%, less than 25%, less than 20%.

In some embodiments, the compounds of the present disclosure show good solubility in water. In some embodiments, the compounds of the present disclosure show a solubility in water of above 90 µM, above 100 µM, above 200 µM, above 300 µM, above 400 µM, above 500 µM, above 600 µM, above 700 µM, above 800 µM, above 900 µM, or above 1000 µM.

As a result of their ATM kinase inhibitory activity (optionally selective ATM kinase inhibitory activity), the compounds of Formula (I), and pharmaceutically acceptable salts thereof are useful in therapy, for example in the treatment of diseases or medical conditions mediated at least in part by ATM kinase, including cancer.

As used herein, the term "cancer" is intended to encompass both non-metastatic cancer and metastatic cancer. In this context, treating cancer involves treatment of both primary tumors and tumor metastases.

As used herein, the term "therapy" is intended to have its normal meaning of dealing with a disease in order to entirely or partially relieve one, some or all of its symptoms, or to correct or compensate for the underlying pathology. The term "therapy" also includes "prophylaxis" unless there are specific indications to the contrary. The terms "therapeutic" and "therapeutically" should be interpreted in a corresponding manner.

As used herein, the term "prophylaxis" is intended to have its normal meaning and includes primary prophylaxis to prevent the development of the disease and secondary prophylaxis whereby the disease has already developed and the patient is temporarily or permanently protected against exacerbation or worsening of the disease or the development of new symptoms associated with the disease.

The term "treatment" is used synonymously with "therapy". Similarly the term "treat" can be regarded as "applying therapy" where "therapy" is as defined herein.

Therefore, in one aspect, there is provided a compound of Formula (I), or a pharmaceutically acceptable salt thereof, for use in therapy.

In some embodiments, there is provided a compound of Formula (I), or a pharmaceutically acceptable salt thereof, for use as a medicament.

In some embodiments, there is provided a compound of Formula (I), or a pharmaceutically acceptable salt thereof, for use in the treatment of ATM-associated diseases or conditions. In some embodiments, the ATM-associated disease or condition is cancer. In some embodiments, the cancer is selected from the group consisting of colorectal cancer, glioblastoma, gastric cancer, ovarian cancer, diffuse large B-cell lymphoma, chronic lymphocytic leukaemia, acute myeloid leukaemia, head and neck squamous cell carcinoma, breast cancer, hepatocellular carcinoma, small cell lung cancer and non-small cell lung cancer. In some embodiments, the cancer is selected from the group consisting of colorectal cancer, glioblastoma, gastric cancer, ovarian cancer, diffuse large B-cell lymphoma, chronic lymphocytic leukaemia, head and neck squamous cell carcinoma and lung cancer.

In some embodiments, there is provided a compound of Formula (I), or a pharmaceutically acceptable salt thereof, for use in the treatment of Huntingdon's disease.

In some embodiments, there is provided a compound of Formula (I), or a pharmaceutically acceptable salt thereof, for use in the manufacture of a medicament for the treatment of ATM-associated diseases or conditions.

In some embodiments, there is provided a compound of Formula (I), or a pharmaceutically acceptable salt thereof, for use in the manufacture of a medicament for the treatment of cancer.

In some embodiments, there is provided a compound of Formula (I), or a pharmaceutically acceptable salt thereof, for use in the manufacture of a medicament for the treatment of Huntingdon's disease.

Pharmaceutical Composition

The present disclosure provides pharmaceutical compositions comprising one or more compound of the present disclosure, or a pharmaceutically acceptable salt thereof. In some embodiments, the pharmaceutical composition comprises one or more compounds of the present disclosure, or a pharmaceutically acceptable salt thereof, and at lease one pharmaceutical acceptable excipient.

A "pharmaceutical composition", as used herein, is a formulation containing the compounds of the present disclosure in a form suitable for administration to a subject. In some embodiments, the pharmaceutical composition is in bulk or in unit dosage form. The unit dosage form is any of a variety of forms, including, for example, tablets, capsules, pills, powders, granules, sachets, cachets, lozenges, suspensions, emulsions, solutions, syrups, aerosols (as a solid or in a liquid medium), spray, ointment, paste, cream, lotion, gel, patch, inhalant, or suppository. The quantity of active ingredient (e.g., a formulation of the disclosed compound or salt, hydrate, solvate or isomer thereof) in a unit dose of composition is a therapeutically effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In some embodiments, the compound of the present disclosure is mixed under sterile conditions with a pharmaceutically acceptable excipient, and with any preservatives, buffers or propellants that are required.

As used herein, the term "pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

As used herein, the term "therapeutically effective amount" refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

In some embodiments, the pharmaceutical compositions can be formulated so that a dosage of between 0.01-500 mg/kg body weight/day, for example, 0.05-500 mg/kg body weight/day, 0.1-500 mg/kg body weight/day, 0.1-400 mg/kg body weight/day, 0.1-300 mg/kg body weight/day, 0.1-200 mg/kg body weight/day, 0.1-100 mg/kg body weight/day, 0.1-80 mg/kg body weight/day, 1-100 mg/kg body weight/day or 1-80 mg/kg body weight/day of the compounds of the present disclosure, or a pharmaceutically acceptable salt thereof, can be administered.

In some embodiments, the pharmaceutical compositions comprise one or more compounds of the present disclosure, or a pharmaceutically acceptable salt thereof, as a first active ingredient, and further comprise a second active ingredient. The second active ingredient can be any anti-tumor agent known in the art, for example, antineoplastic agents, anti-angiogenic agents, immunotherapy approaches, efficacy enhancers, and the like.

Examples of the antineoplastic agents include, but are not limited to, DNA alkylating agents (for example cisplatin, oxaliplatin, carboplatin, cyclophosphamide, nitrogen mustards like ifosfamide, bendamustine, melphalan, chlorambucil, busulphan, temozolamide and nitrosoureas like carmustine); antimetabolites (for example gemcitabine and antifolates such as fluoropyrimidines like 5-fluorouracil and tegafur, raltitrexed, methotrexate, cytosine arabinoside, and hydroxyurea); anti-tumor antibiotics (for example anthracyclines like adriamycin, bleomycin, doxorubicin, liposomal doxorubicin, pirarubicin, daunomycin, valrubicin, epirubicin, idarubicin, mitomycin-C, dactinomycin, amrubicin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, irinotecan, topotecan and camptothecin); inhibitors of DNA repair mechanisms such as CHK kinase; DNA-dependent protein kinase inhibitors; inhibitors of poly (ADP-ribose) polymerase (PARP inhibitors, including olaparib); and Hsp90 inhibitors such as tanespimycin and retaspimycin, inhibitors of ATR kinase (such as AZD6738); and inhibitors of WEE 1 kinase (such as AZD1775/MK-1775).

Examples of antiangiogenic agents include those that inhibit the effects of vascular endothelial growth factor, such as but not limited to, the anti-vascular endothelial cell growth factor antibody bevacizumab, a VEGF receptor tyrosine kinase inhibitor such as vandetanib (ZD6474), sorafenib, vatalanib (PTK787), sunitinib (SU11248), axitinib (AG-013736), pazopanib (GW 786034) and cediranib (AZD2171); compounds such as those disclosed in International Patent Applications WO 97/22596, WO 97/30035, WO 97/32856 and WO 98/13354; and compounds that work by other mechanisms (for example linomide, inhibitors of integrin $\alpha v\beta 3$ function and angiostatin), or inhibitors of angiopoietins and their receptors (Tie-1 and Tie-2), inhibitors of PLGF, inhibitors of delta-like ligand (DLL-4).

Examples of immunotherapy approaches include, but are not limited to, ex-vivo and in-vivo approaches to increase the immunogenicity of patient tumor cells, such as transfection with cytokines such as interleukin 2, interleukin 4 or granulocyte-macrophage colony stimulating factor; approaches to decrease T-cell anergy or regulatory T-cell function; approaches that enhance T-cell responses to tumors, such as blocking antibodies to CTLA4 (for example ipilimumab and tremelimumab), B7H1, PD-1 (for example BMS-936558 or AMP-514), PD-L1 (for example MEDI4736) and agonist antibodies to CD 137; approaches using transfected immune cells such as cytokine-transfected dendritic cells; approaches using cytokine-transfected tumor cell lines, approaches using antibodies to tumor associated antigens, and antibodies that deplete target cell types (e.g., unconjugated anti-CD20 antibodies such as Rituximab, radiolabeled anti-CD20 antibodies Bexxar and Zevalin, and anti-CD54 antibody Campath); approaches using anti-idiotypic antibodies; approaches that enhance Natural Killer cell function; and approaches that utilize antibody-toxin conjugates (e.g. anti-CD33 antibody Mylotarg); immunotoxins such as moxetumumab pasudotox; agonists of toll-like receptor 7 or toll-like receptor 9.

Examples of efficacy enhancers include leucovorin.

Therefore, in some embodiments, there is provided pharmaceutical composition comprising a compound of Formula (I), or a pharmaceutically acceptable salt thereof, and at least one additional anti-tumor agent. In some embodiments, there is one additional anti-tumor agent. In some embodiments, there are two additional anti-tumor agents. In some embodiments, there are three or more additional anti-tumor agents.

In some embodiments, the amount of additional anti-tumor agent present in the composition of the present disclosure can be no more than the amount that would normally be administered in a composition comprising that anti-tumor agent as the only active agent. In certain embodiments, the amount of the additional anti-tumor agent in the composition of the present disclosure will range from about 50% to 100% of the amount normally present in a composition comprising that anti-tumor agent as the only therapeutically active agent.

Therefore, in another aspect, there is provided a compound of formula (I) or a pharmaceutically acceptable salt thereof in combination with one or more anti-tumor agents listed above.

As used herein, the term "combination" refers to simultaneous, separate or sequential administration. In some embodiments, "combination" refers to simultaneous administration. In some embodiments, "combination" refers to separate administration. In some embodiments, "combination" refers to sequential administration. Where the administration is sequential or separate, the delay in administering the second component should not be such as to lose the beneficial effect of the combination.

In a further aspect, there is provided a pharmaceutical composition comprising a compound of formula (I) or a pharmaceutically acceptable salt thereof in combination with one or more anti-tumor agents listed above, in association with a pharmaceutically acceptable excipient.

In a further aspect, there is provided a kit comprising a compound of formula (I) or a pharmaceutically acceptable salt thereof in combination with one or more anti-tumor agents listed above.

In a further aspect, there is provided a kit comprising:
(a) a compound of formula (I) or a pharmaceutically acceptable salt thereof in a first unit dosage form;
(b) an anti-tumor agent selected from those listed above in a second unit dosage form; and
(c) container for containing the first and second unit dosage forms.

Method for Treatment

In a further aspect, there is provided a method of treating ATM-associated diseases or conditions in a subject in need thereof, which comprises administering to the subject a therapeutically effective amount of a compound of Formula (I) or a pharmaceutically acceptable salt thereof, or a pharmaceutical composition of the present disclosure, owning to the selective ATM kinase inhibitory activity, non-AO, non-Pgp and non-BCRP liability and brain penetration capability of the compounds of the present disclosure.

In some embodiments, the ATM-associated disease or condition is cancer. In some embodiments, the cancer is selected from the group consisting of colorectal cancer, glioblastoma, gastric cancer, ovarian cancer, diffuse large B-cell lymphoma, chronic lymphocytic leukaemia, acute myeloid leukaemia, head and neck squamous cell carcinoma, breast cancer, hepatocellular carcinoma, small cell lung cancer and non-small cell lung cancer. In some embodiments, the cancer is metastatic cancer. In some embodiments, the metastatic cancer comprises metastases of the central nervous system. In some embodiments, the metastases of the central nervous system comprise brain metastases. In some embodiments, the metastases of the central nervous system comprise leptomeningeal metastases. "Leptomeningeal metastases" occur when cancer spreads to the meninges, the layers of tissue that cover the brain and the spinal cord. Metastases can spread to the meninges through the blood or they can travel from brain metastases, carried by the cerebrospinal fluid (CSF) that flows through the meninges.

In a further aspect, there is provided a method of treating Huntingdon's disease in a subject in need thereof, which comprises administering to the subject a therapeutically effective amount of a compound of Formula (I) or a pharmaceutically acceptable salt thereof, or a pharmaceutical composition of the present disclosure.

As used herein, the term "subject in need thereof" is a subject having an ATM-associated disease or condition (e.g., cancer), or a subject having an increased risk of developing an ATM-associated disease or condition (e.g., cancer) relative to the population at large. In the case of cancer, a subject in need thereof can have a precancerous condition. A "subject" includes a warm-blooded animal. In some embodiments, the warm-blooded animal is a human.

In this context, the term "therapeutically effective amount" refers to an amount of a compound of Formula (I) or pharmaceutically acceptable salts thereof which is effective to provide "therapy" in a subject, or to "treat" an ATM-associated disease or disorder in a subject. In the case of cancer, the therapeutically effective amount may cause any of the changes observable or measurable in a subject as described in the definition of "therapy", "treatment" and "prophylaxis" above. For example, the effective amount can reduce the number of cancer or tumor cells; reduce the overall tumor size; inhibit or stop tumor cell infiltration into peripheral organs including, for example, the soft tissue and bone; inhibit and stop tumor metastasis; inhibit and stop tumor growth; relieve to some extent one or more of the symptoms associated with the cancer; reduce morbidity and mortality; improve quality of life; or a combination of such effects. An effective amount may be an amount sufficient to decrease the symptoms of a disease responsive to inhibition of ATM kinase activity. For cancer therapy, efficacy in-vivo can, for example, be measured by assessing the duration of survival, time to disease progression (TTP), the response rates (RR), duration of response, and/or quality of life. As recognized by those skilled in the art, effective amounts may vary depending on route of administration, excipient usage, and co-usage with other agents. For example, where a combination therapy is used, the amount of the compound of formula (I) or pharmaceutically acceptable salt described in this specification and the amount of the other pharmaceutically active agent(s) are, when combined, jointly effective to treat a targeted disorder in the animal patient. In this context, the combined amounts are in a "therapeutically effective amount" if they are, when combined, sufficient to decrease the symptoms of a disease responsive to inhibition of ATM activity as described above.

In generally, "therapeutically effective amount" may be determined by one skilled in the art by, for example, starting with the dosage range described in this specification for the compound of formula (I) or pharmaceutically acceptable salt thereof and an approved or otherwise published dosage range(s) of the other pharmaceutically active compound(s).

The method of treating ATM-associated diseases or conditions described in this specification may be used as a monotherapy. As used herein, the term "monotherapy" refers to the administration of a single active or therapeutic compound to a subject in need thereof. In some embodiments, monotherapy will involve administration of a therapeutically effective amount of one of the compounds of the present disclosure, or a pharmaceutically acceptable salt thereof, to a subject in need of such treatment.

Depending upon the particular diseases or conditions to be treated, the method of treating ATM-associated diseases or conditions described in this specification may involve, in addition to administration of the compound of Formula (I), one or more additional therapies, for example, conventional surgery, radiotherapy, chemotherapy, or a combination of such additional therapies. As used herein, the term"combination therapy" refers to the administration of a combination of multiple active compounds.

The additional therapies, such as additional anti-tumor agents, may be administered separately from the compounds of the present disclosure, as part of a multiple dosage regimen. Alternatively, these additional therapies may be part of a single dosage form, mixed with the compounds of the present disclosure in a single composition.

In some embodiments, the compounds of the present disclosure may be administered simultaneously, sequentially or separately to treatment with the conventional surgery, radiotherapy or chemotherapy.

Radiotherapy may include one or more of the following categories of therapy: (i) external radiation therapy using electromagnetic radiation, and intraoperative radiation therapy using electromagnetic radiation; (ii) internal radiation therapy or brachytherapy; including interstitial radiation therapy or intraluminal radiation therapy; or (iii) systemic radiation therapy, including but not limited to iodine 131 and strontium 89.

Chemotherapy may include anti-tumor agents known in the art, for example, antineoplastic agents, antiangiogenic agents, immunotherapy approaches, efficacy enhancers, and the like described in this specification.

Therefore, in one aspect, there is provided a method of treating ATM-associated diseases or conditions in a subject in need thereof, wherein the compound of Formula (I) or pharmaceutically acceptable salts thereof is administered simultaneously, separately or sequentially with radiotherapy.

In some embodiments, the radiotherapy is brain radiation.

In some embodiments, the ATM-associated disease or condition is cancer. In some embodiments, the cancer is selected from glioblastoma, lung cancer (for example small cell lung cancer or non-small cell lung cancer), breast cancer (for example triple negative breast cancer), head and neck squamous cell carcinoma, oesophageal cancer, cervical cancer and endometrial cancer. In some embodiments, the cancer is glioblastoma. In some embodiment, the cancer is metastatic cancer. In some embodiments, the metastatic cancer is metastases of the central nervous system. In some embodiments, the metastases of the central nervous system is brain metastases.

In some embodiments, there is provided a method of treating glioblastoma in a subject in need thereof, wherein the compound of Formula (I) or pharmaceutically acceptable salts thereof is administered simultaneously, separately or sequentially with brain radiation.

In another aspect, there is provided a method of treating ATM-associated diseases or conditions in a subject in need thereof, wherein the compound of Formula (I) or pharmaceutically acceptable salts thereof is administered simultaneously, separately or sequentially with one or more additional anti-tumor agents.

In some embodiments, the ATM-associated disease or condition is cancer. In certain embodiments, the amounts of the compound of Formula (I), or a pharmaceutically acceptable salt thereof, and the one or more additional anti-tumor agents are jointly effective in producing an anti-cancer effect.

In some embodiments, the additional anti-tumor agent includes antineoplastic agents, antiangiogenic agents, immunotherapy approaches, efficacy enhancers and the like.

In some embodiments, the additional anti-tumor agent is selected from the group consisting of doxorubicin, irinotecan, topotecan, etoposide, mitomycin, bendamustine, chlorambucil, cyclophosphamide, ifosfamide, carmustine, melphalan and bleomycin.

EXAMPLES

For the purpose of illustration, the following examples are included. However, it is to be understood that these examples do not limit the invention and are only meant to suggest a method of practicing the present disclosure. Persons skilled in the art will recognize that the chemical reactions described may be readily adapted to prepare a number of other compounds of the present disclosure, and alternative methods for preparing the compounds of the present disclosure are deemed to be within the scope of the present disclosure. For example, the synthesis of non-exemplified compounds according to the present disclosure may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the present disclosure.

The following abbreviations have been used in the examples:

| | |
|---|---|
| $AlCl_3$ | aluminum chloride |
| aq. | aqueous |
| $B_2Pin_2$ | bis(dinacolato)diboron |
| CDI | N,N'-carbonyldiimidazole |
| $CH_2Cl_2$ | dichloromethane |
| conc. | concentrated |
| $Cs_2CO_3$ | cesiumcarbonate |
| DCM | dichloromethane |
| DIEA or DIPEA | diisopropylethylamine |
| DMF | N,N-Dimethylformamide |
| EDCl | 1-ethyl-3-(3-dimethylaminopropyl)-carbodiimide |
| $Et_3N$ | triethylamine |
| EtOAc | ethyl acetate |
| $HNO_3$ | nitric acid |
| HOBt | 1-hydroxybenzotriazole |
| $H_2SO_4$ | sulfuric acid |
| hr(s) | hour(s) |
| $K_2CO_3$ | potassium carbonate |
| KOAc | potassium acetate |
| MeCN | acetonitrile |
| MeI | methyl iodide |
| MeOH | methanol |
| MsCl | p-anisolesulphonyl chloride |
| NaH | sodium hydride |
| $NaHCO_3$ | sodium bicarbonate |
| $NaNO_2$ | sodium nitrite |
| $Na_2SO_4$ | sodium sulfate |
| $Pd(dppf)Cl_2$ | [1,1'-bis(diphenylphosphino)ferrocene]dichloropalladium(II) |
| PE | petroleium ether |
| $POCl_3$ | phosphoric trichloride |
| PTSA | p-toluenesulfonic acid |
| r.t. | room temperature (~18-25° C.) |
| THF | tetrahydrofuran |

Example 1

7-fluoro-1-isopropyl-3-methyl-8-(6-(3-(piperidin-1-yl)propoxy)pyridin-3-yl)-1H-imidazo[4,5-c]cinnolin-2(3H)-one Compound of Example 1 was prepared according to the synthetic route shown in Scheme 1:

Scheme 1

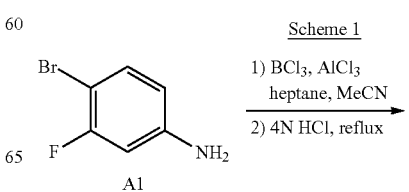

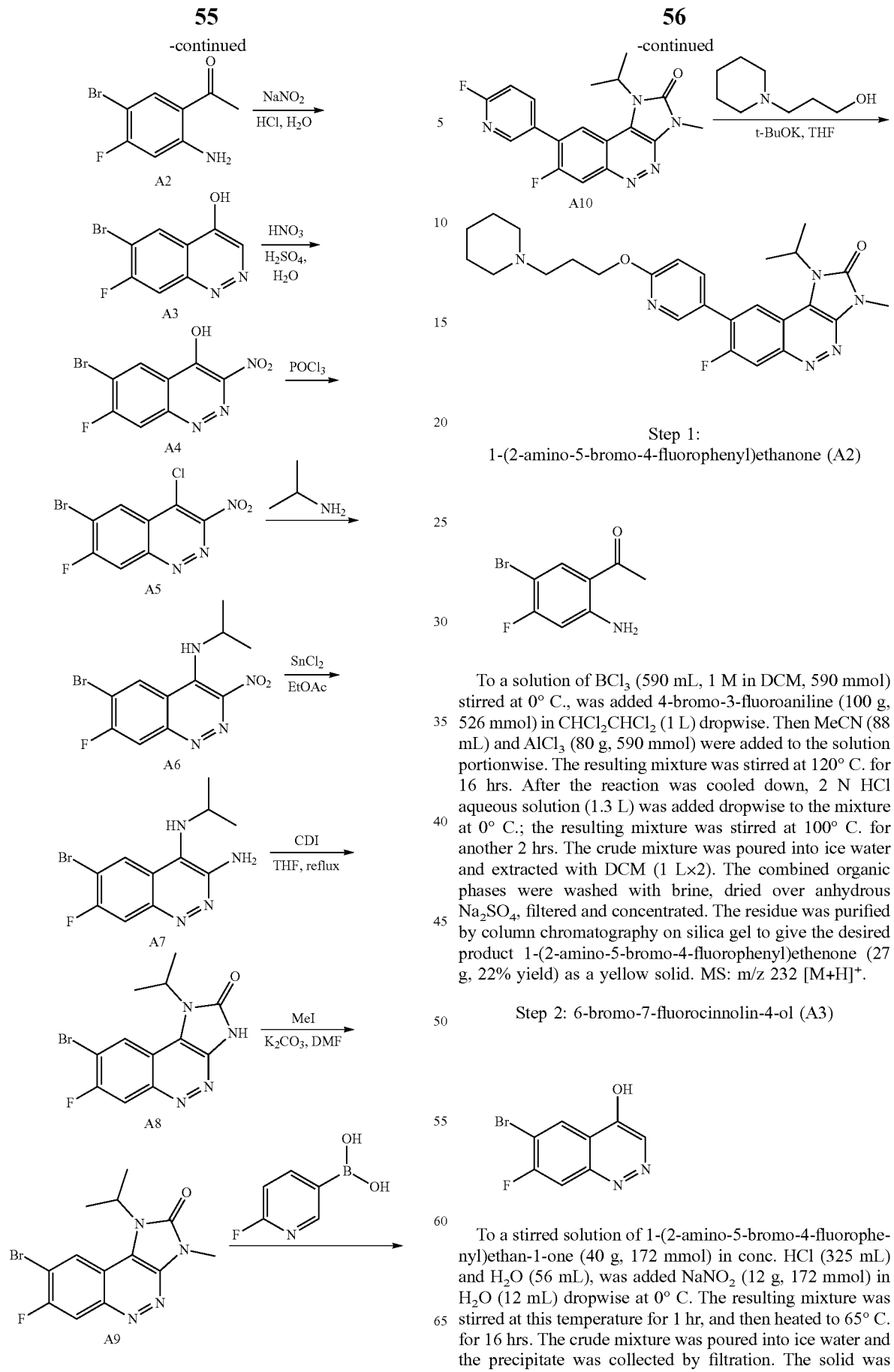

Step 1:
1-(2-amino-5-bromo-4-fluorophenyl)ethanone (A2)

To a solution of BCl$_3$ (590 mL, 1 M in DCM, 590 mmol) stirred at 0° C., was added 4-bromo-3-fluoroaniline (100 g, 526 mmol) in CHCl$_2$CHCl$_2$ (1 L) dropwise. Then MeCN (88 mL) and AlCl$_3$ (80 g, 590 mmol) were added to the solution portionwise. The resulting mixture was stirred at 120° C. for 16 hrs. After the reaction was cooled down, 2 N HCl aqueous solution (1.3 L) was added dropwise to the mixture at 0° C.; the resulting mixture was stirred at 100° C. for another 2 hrs. The crude mixture was poured into ice water and extracted with DCM (1 L×2). The combined organic phases were washed with brine, dried over anhydrous Na$_2$SO$_4$, filtered and concentrated. The residue was purified by column chromatography on silica gel to give the desired product 1-(2-amino-5-bromo-4-fluorophenyl)ethenone (27 g, 22% yield) as a yellow solid. MS: m/z 232 [M+H]$^+$.

Step 2: 6-bromo-7-fluorocinnolin-4-ol (A3)

To a stirred solution of 1-(2-amino-5-bromo-4-fluorophenyl)ethan-1-one (40 g, 172 mmol) in conc. HCl (325 mL) and H$_2$O (56 mL), was added NaNO$_2$ (12 g, 172 mmol) in H$_2$O (12 mL) dropwise at 0° C. The resulting mixture was stirred at this temperature for 1 hr, and then heated to 65° C. for 16 hrs. The crude mixture was poured into ice water and the precipitate was collected by filtration. The solid was washed with water and dried under vacuum to give the desired product (33 g, 79% yield) as a yellow solid. MS: m/z 243 [M+H]⁺.

Step 3: 6-bromo-7-fluoro-3-nitrocinnolin-4-ol (A4)

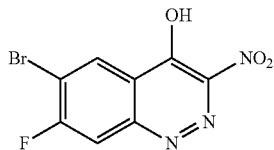

To a solution of 6-bromo-7-fluorocinnolin-4-ol (50 g, 206 mmol) in conc. $HNO_3$ (167 mL) stirred at 0° C., was carefully added conc. $H_2SO_4$ (50 mL) dropwise in 10 min. The resulting mixture was stirred at 60° C. for 3 hrs. After cooled down, the crude mixture was poured into ice water. The precipitate was collected by filtration, washed with water and dried under vacuum to give the desired product (40 g, 67% yield) as a yellow solid. MS: m/z 288 [M+H]⁺.

Step 4: 6-bromo-4-chloro-7-fluoro-3-nitrocinnoline (A5)

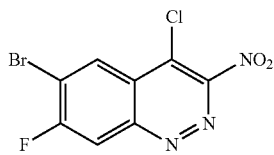

To a solution of 6-bromo-7-fluoro-3-nitrocinnolin-4-ol (40 g, 139 mmol) in DMF (200 mL) stirred at 0° C., was added $POCl_3$ (28 g, 180 mmol) dropwise. The resulting mixture was stirred at r.t. for 16 hrs. The crude mixture was poured in ice water and extracted with EtOAc (300 mL). The organic phase was washed with water and brine, dried over anhydrous $Na_2SO_4$, filtered and concentrated to give the crude product (32 g, 75% yield) as a red oil, which was used for next step without further purification.

Step 5: 6-bromo-7-fluoro-N-isopropyl-3-nitrocinnolin-4-amine (A6)

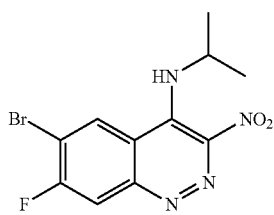 [SMILES: CC(C)Nc1c([N+](=O)[O-])nnc2cc(F)c(Br)cc12]

To a solution of 6-bromo-4-chloro-7-fluoro-3-nitrocinnoline (32 g, 104 mmol) and $Et_3N$ (31 g, 312 mmol) in DCM (500 mL) stirred at r.t., was added isopropylamine (12 g, 208 mmol). The resulting mixture was stirred at r.t. for 2 hrs. The crude mixture was then concentrated to dryness and the residue was purified by column chromatography on silica gel to give the desired product (30 g, 87% yield) as a yellow solid. MS: m/z 329 [M+H]⁺.

Step 6: 6-bromo-7-fluoro-N4-isopropylcinnoline-3,4-diamine (A7)

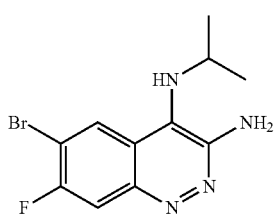

To a solution of 6-bromo-7-fluoro-N-isopropyl-3-nitrocinnolin-4-amine (44 g, 134 mmol) in EtOAc (10 mL) stirred at room temperature, was added $SnCl_2 \cdot 2H_2O$ (117 g, 536 mmol). The resulting mixture was stirred at 80° C. for 2 hrs. The crude mixture was basified with aq. $NaHCO_3$ to adjust pH=9 and then filtered. The filtrate was diluted with EtOAc (1 L). The organic phase was washed with water and brine, filtered and concentrated. The residue was purified by column chromatography on silica gel to give the desired product (26 g, 65% yield) as a yellow solid. MS: m/z 299 [M+H]⁺.

Step 7: 8-bromo-7-fluoro-1-isopropyl-1H-imidazo[4,5-c]cinnolin-2(3H)-one (A8)

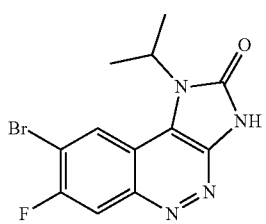 [SMILES: CC(C)n1c(=O)[nH]c2nnc3cc(F)c(Br)cc3c21]

To a solution of 6-bromo-7-fluoro-N4-isopropylcinnoline-3,4-diamine (26 g, 87 mmol) in THF (200 mL) stirred at room temperature, was added CDI (81 g, 500 mmol). The resulting mixture was stirred at 70° C. for 16 hrs. The crude mixture was concentrated and the residue was poured into ice water, extracted with EtOAc (1 L). The organic phase was washed with water and brine, dried over anhydrous $Na_2SO_4$, filtered and concentrated. The residue was purified by column chromatography on silica gel to give the desired product (21 g, 74% yield) as a yellow solid. MS: m/z 325 [M+H]⁺.

Step 8: 8-bromo-7-fluoro-1-isopropyl-3-methyl-1H-imidazo[4,5-c]cinnolin-2(3H)-one (A9)

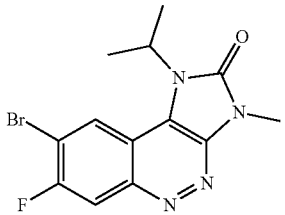 [SMILES: CC(C)n1c(=O)n(C)c2nnc3cc(F)c(Br)cc3c21]

To a solution of 8-bromo-7-fluoro-1-isopropyl-1H-imidazo[4,5-c]cinnolin-2(3H)-one (21 g, 64 mmol) in DMF (200 mL) stirred at r.t., was added K₂CO₃ (26 g, 194 mmol). The resulting mixture was stirred at 40° C. for 2 hrs and then cooled to 0° C. After dropwise addition of MeI (22 g, 161 mmol), the reaction was stirred at r.t. for 2 hrs. The crude mixture was then poured into ice water and the precipitate was collected by filtration. The solid was washed with water, dried under vacuum to give the desired product (13 g, 59% yield) as a yellow solid. MS: m/z 339 [M+H]⁺.

Step 9: 7-fluoro-8-(6-fluoropyridin-3-yl)-1-isopropyl-3-methyl-1H-imidazo[4,5-c]cinnolin-2(3H)-one (A10)

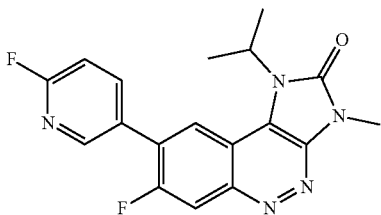 [SMILES: CC(C)n1c(=O)n(C)c2nnc3cc(F)c(-c4ccc(F)nc4)cc3c21]

To a mixture of (6-fluoropyridin-3-yl)boronic acid (2 g, 15 mmol) and 8-bromo-7-fluoro-1-isopropyl-3-methyl-1,3-dihydro-2H-imidazo[4,5-c]cinnolin-2-one (5 g, 15 mmol) in 1,4-dioxane (100 mL) and water (10 mL) was added Na₂CO₃ (125.4 mg, 1.18 mmol) followed by Pd(dppf)Cl₂ (1.1 g, 1.5 mmol). The reaction mixture was stirred at 100° C. for 16 hrs under N₂ protection. The mixture was partitioned with EtOAc and water. The organic layers were washed with brine, dried over anhydrous Na₂SO₄ and concentrated under reduced pressure. The residue was purified by chromatography on silica gel (DCM:MeOH=50:1) to give the desired product (5 g, 95% yield) as a yellow solid. MS: m/z 356 [M+H]⁺.

Step 10: 7-fluoro-1-isopropyl-3-methyl-8-(6-(3-(piperidin-1-yl)propoxy)pyridin-3-yl)-1H-imidazo[4,5-c]cinnolin-2(3H)-one

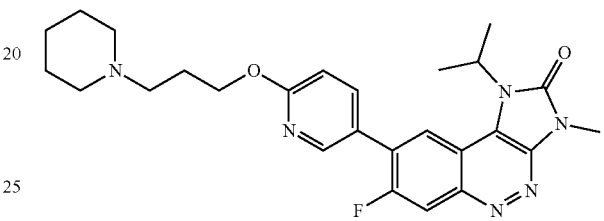

To a solution of 3-(piperidin-1-yl)propan-1-ol (1 g, 6.8 mmol) in THF (30 mL) was added t-BuOK (1 g, 9 mmol) at 0° C. After the reaction mixture was stirred at 0° C. for 30 min, 7-fluoro-8-(6-fluoropyridin-3-yl)-1-isopropyl-3-methyl-1H-imidazo[4,5-c]cinnolin-2(3H)-one (1.6 g, 4.5 mmol) was added thereto. The reaction mixture was stirred at r.t. for another 1 hr and poured into ice water. The resulting mixture was extracted with DCM twice. The combined organic layers were washed with brine, dried over anhydrous Na₂SO₄ and concentrated under reduced pressure. The residue was purified by chromatography on silica gel (DCM:MeOH=30:1) to give the desired product (530 mg, 25% yield) as white solid. MS: 479 [M+H]⁺. ¹H NMR (400 MHz, DMSO-d₆) δ 8.51 (t, J=1.9 Hz, 1H), 8.33 (d, J=7.8 Hz, 1H), 8.16 (d, J=11.5 Hz, 1H), 8.05 (d, J=8.7 Hz, 1H), 6.98 (d, J=8.6 Hz, 1H), 5.29-5.19 (m, 1H), 4.36 (t, J=6.6 Hz, 2H), 3.57 (s, 3H), 2.48-2.18 (m, 6H), 1.98-1.84 (m, 2H), 1.63 (d, J=6.7 Hz, 6H), 1.58-1.32 (m, 6H).

Compound of Example 1 was also prepared according to the synthetic route shown in Scheme 2:

Scheme 2

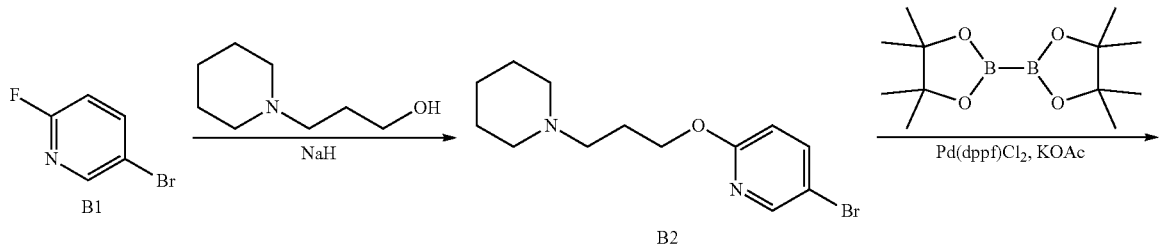

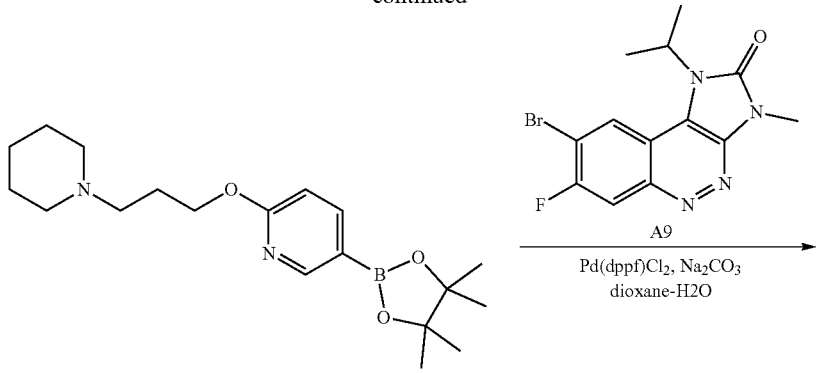

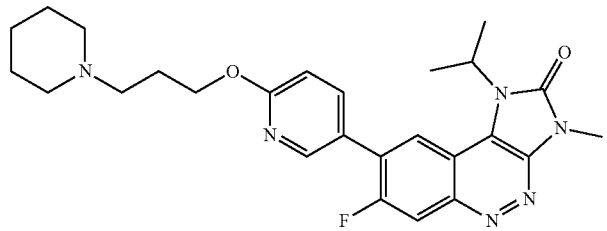 [SMILES: CC(C)n1c(=O)n(C)c2nnc3cc(F)c(-c4ccc(OCCCN5CCCCC5)nc4)cc3c21]

Step 1: 5-bromo-2-(3-(piperidin-1-yl)propoxy)pyridine (B2)

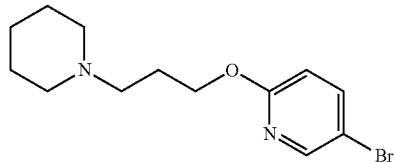 [SMILES: Brc1ccc(OCCCN2CCCCC2)nc1]

To a solution of 3-(piperidin-1-yl)propan-1-ol (4 g, 28.4 mmol) in DMF (50 mL) was added NaH (2.3 g, 56.8 mmol) at 0° C. and the reaction mixture was stirred at 0° C. for 30 min. Then to the mixture was added 5-bromo-2-fluoropyridine (5 g, 28.4 mmol) and the reaction mixture was stirred at r.t. overnight. The mixture was poured into ice water and extracted with EtOAc (200 mL×2). The combined organic layers were washed with brine, dried over anhydrous $Na_2SO_4$ and concentrated under reduced pressure. The residue was purified by chromatography on silica gel (PE:EtOAc=4:1 to 1:1) to give product (5.2 g, 61.2% yield) as brown oil. MS: m/z 299 [M+H]$^+$.

Step 2&3: 7-fluoro-1-isopropyl-3-methyl-8-(6-(3-(piperidin-1-yl)propoxy)pyridin-3-yl)-1H-imidazo[4,5-c]cinnolin-2(3H)-one

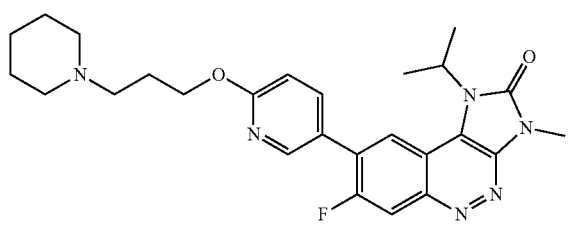 [SMILES: CC(C)n1c(=O)n(C)c2nnc3cc(F)c(-c4ccc(OCCCN5CCCCC5)nc4)cc3c21]

To a solution of 5-bromo-2-(3-(piperidin-1-yl)propoxy)pyridine (2.6 g, 8.7 mmol), 4,4,5,5-tetramethyl-2-(tetramethyl-1,3,2-dioxaborolan-2-yl)-1,3,2-dioxaborolane (2.2 g, 8.7 mmol) and KOAc (2.6 g, 26.1 mmol) in 1,4-dioxane (50 mL) stirred at r.t. under nitrogen, was added Pd(dppf)Cl$_2$ (0.7 g, 1.0 mmol), the resulting mixture was stirred at 90° C. under nitrogen overnight and cooled down. 8-bromo-7-fluoro-1-isopropyl-3-methyl-1,3-dihydro-2H-imidazo[4,5-c]cinnolin-2-one (2.9 g, 8.7 mmol), Na$_2$CO$_3$ (9.2 g, 8.7 mmol), H$_2$O (10 mL) and Pd(dppf)Cl$_2$ (640 mg, 0.87 mmol) were added to above mixture under nitrogen. The resulting mixture was stirred at 100° C. for 16 hrs. After cooled down, the crude mixture was filtered and the filtrate was concentrated to dryness. The residue was purified by chromatography on silica gel (DCM:MeOH=30:1) give the desired product (1.2 g, 29% yield) as a pale yellow solid. The analytical data was identical to the previous method.

Example 2

8-(6-(3-(dimethylamino)propoxy)pyridin-3-yl)-7-fluoro-1-isopropyl-3-methyl-1H-imidazo[4,5-c]cinnolin-2(3H)-one

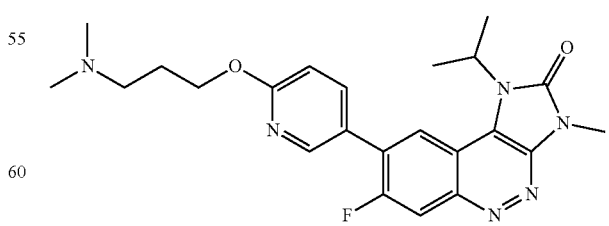

The title compound was synthesized directly from 8-bromo-7-fluoro-1-isopropyl-3-methyl-1,3-dihydro-2H-imidazo[4,5-c]cinnolin-2-one according to Scheme 2 in Example 1 to give the desired product (17% yield) as a yellow solid. MS: m/z 439 [M+H]⁺. ¹H NMR (400 MHz, CDCl₃) δ 8.40 (s, 1H), 5.16-5.10 (m, 2H), 7.91 (dt, J=8.6, 2.3 Hz, 1H), 6.91 (d, J=8.6 Hz, 1H), 5.20-5.07 (m, 1H), 4.52 (t, J=5.8 Hz, 2H), 3.75 (s, 3H), 3.20-3.14 (m, 2H), 2.81 (s, 6H), 2.43-2.36 (m, 2H), 1.76 (d, J=6.9 Hz, 6H).

Example 3

7-fluoro-1-isopropyl-3-methyl-8-(6-(3-(pyrrolidin-1-yl)propoxy)pyridin-3-yl)-1H-imidazo[4,5-c]cinnolin-2(3H)-one

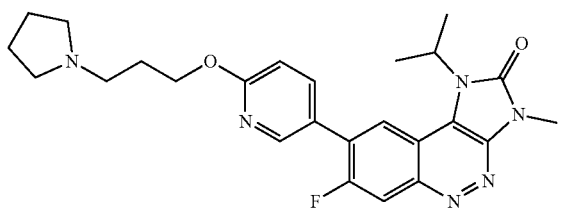 [SMILES: CC(C)n1c(=O)n(C)c2nnc3cc(F)c(-c4ccc(OCCCN5CCCC5)nc4)cc3c21]

The title compound was synthesized according to Scheme 1 in Example 1 to give the desired product (41% yield) as a white solid. MS: m/z 465 [M+H]⁺. ¹H NMR (400 MHz, CD₃OD) δ 8.45 (t, J=2.1 Hz, 1H), 8.31 (d, J=7.6 Hz, 1H), 8.10-7.94 (m, 2H), 6.95 (d, J=8.6 Hz, 1H), 5.35-5.17 (m, 1H), 4.43 (t, J=6.3 Hz, 2H), 3.67 (s, 3H), 2.73-2.53 (m, 6H), 2.14-2.01 (m, 2H), 1.84 (p, J=3.2 Hz, 4H), 1.74 (d, J=6.8 Hz, 6H).

The title compound was also synthesized according to Scheme 2 in Example 1 to give the desired product (53% yield) as a white solid with the analytical data identical to those obtained above.

Example 4

8-(6-(4-(dimethylamino)piperidin-1-yl)pyridin-3-yl)-7-fluoro-1-isopropyl-3-methyl-1H-imidazo[4,5-c]cinnolin-2(3H)-one

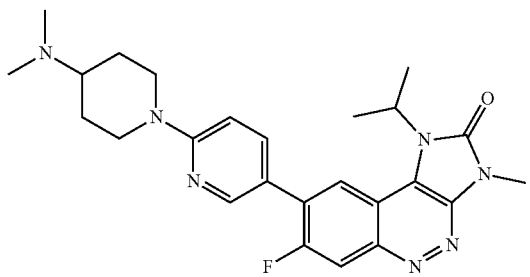

To a mixture of 7-fluoro-8-(6-fluoropyridin-3-yl)-1-isopropyl-3-methyl-1,3-dihydro-2H-imidazo[4,5-c]cinnolin-2-one (23 mg, 0.06 mmol) and N,N-dimethylpiperidin-4-amine (11.1 mg, 0.09 mmol) in acetonitrile (4 mL) was added Cs₂CO₃ (75.5 mg, 0.23 mmol) and the reaction mixture was stirred at 100° C. overnight. The mixture was filtered and the filtrate was evaporated under reduced pressure. The residue was purified by Prep-TLC (DCM:MeOH=10:1) to give the desired product (15 mg, 51% yield) as yellow solid. MS: m/z 464 [M+H]⁺. ¹H NMR (400 MHz, CDCl₃) δ 8.46 (s, 1H), 8.10 (t, J=9.2 Hz, 2H), 7.83 (dt, J=8.9, 2.4 Hz, 1H), 6.82 (d, J=9.0 Hz, 1H), 5.21-5.06 (m, 1H), 4.60-4.56 (m, 2H), 3.74 (s, 3H), 3.01-2.94 (m, 3H), 2.60 (s, 6H), 2.22-2.19 (m, 2H), 1.76-1.70 (m, 8H).

Example 5

8-(6-(3-((dimethylamino)methyl)pyrrolidin-1-yl)pyridin-3-yl)-7-fluoro-1-isopropyl-3-methyl-1H-imidazo[4,5-c]cinnolin-2(3H)-one

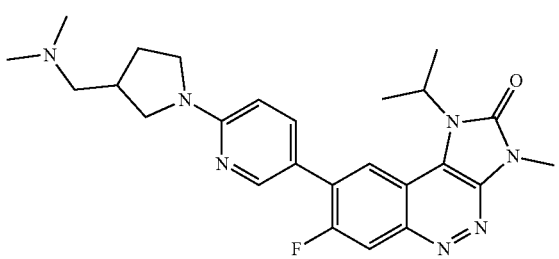

The title compound was prepared using similar procedure as in Example 4. MS: m/z 464 [M+H]⁺. ¹H NMR (400 MHz, CDCl₃) δ 8.45 (s, J=2.3 Hz, 1H), 8.11-8.07 (m, 2H), 7.80 (dt, J=8.8, 2.6 Hz, 1H), 6.52 (d, J=8.9 Hz, 1H), 5.20-5.10 (m, 1H), 3.78-3.69 (m, 5H), 3.57-3.52 (m, 1H), 3.29-3.25 (m, 1H), 2.65-2.58 (m, 1H), 2.47-2.45 (m, 1H), 2.35 (s, 6H), 2.28-2.20 (m, 1H), 1.86-1.81 (m, 2H), 1.75 (d, J=7.0 Hz, 6H).

Example 6

8-(6-((2-(dimethylamino)ethoxy)methyl)pyridin-3-yl)-7-fluoro-1-isopropyl-3-methyl-1H-imidazo[4,5-c]cinnolin-2(3H)-one Compound of Example 6 was prepared according to the synthetic route shown in Scheme 3.

Scheme 3

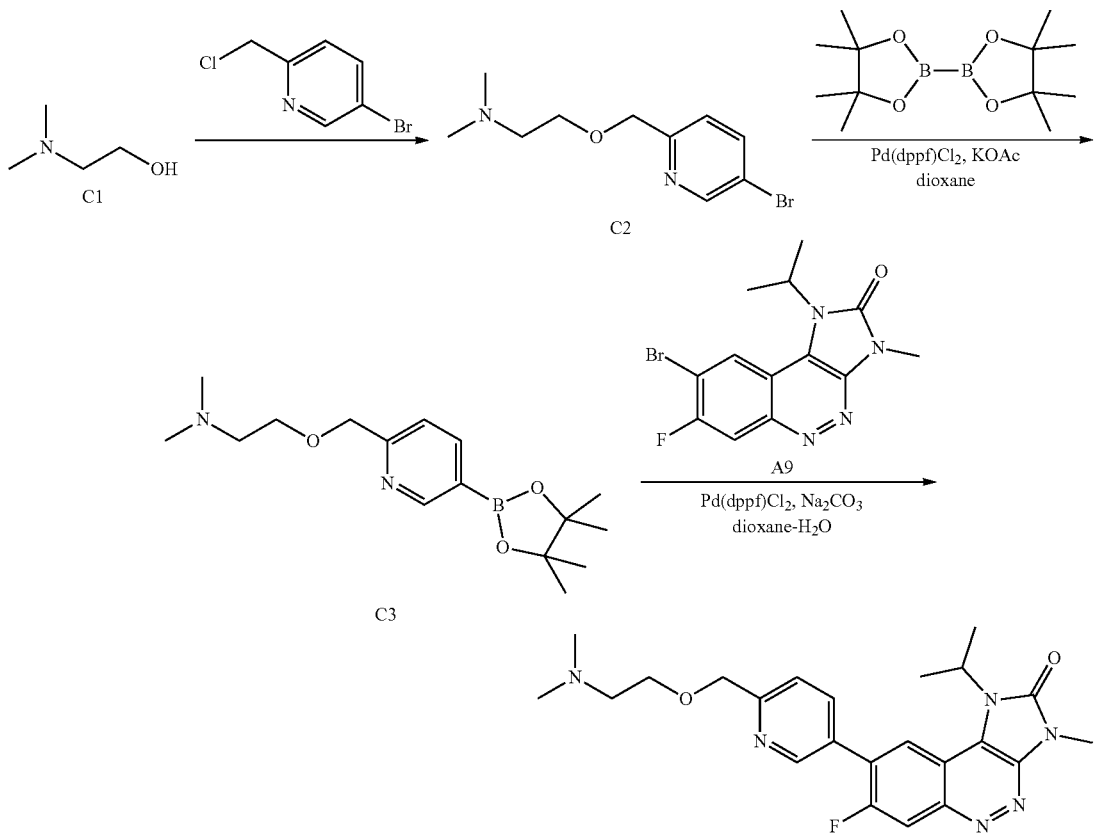

Step 1: 2-((5-bromopyridin-2-yl)methoxy)-N,N-dimethylethanamine (C2)

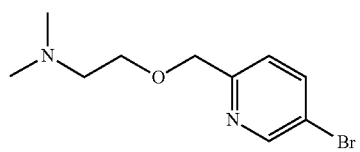

To a solution of 2-(dimethylamino)ethanol (267 mg, 3.0 mmol) in DMF (20 mL) stirred at 0° C. under nitrogen, was added NaH (60%, 120 mg, 3.0 mmol). The resulting mixture was stirred at 0° C. for another 30 min, and then 5-bromo-2-(chloromethyl)pyridine (300 mg, 1.5 mmol) was added thereto. After stirred at r.t. for 2 hrs, the crude mixture was poured into ice water and extracted with EtOAc (10 mL×2). The combined organic layers were washed with water and brine, dried over anhydrous $Na_2SO_4$, filtered and then concentrated to give the crude product (350 mg) as brown oil, which was used for next step without further purification. MS: m/z 259 [M+H]$^+$.

Step 2&3: 8-(6-((2-(dimethylamino)ethoxy)methyl)pyridin-3-yl)-7-fluoro-1-isopropyl-3-methyl-1H-imidazo[4,5-c]cinnolin-2(3H)-one To a solution of 2-((5-bromopyridin-2-yl)methoxy)-N,N-dimethylethan-1-amine (350 mg, 1.4 mmol), KOAc (392 mg, 4.0 mmol) and 4,4,5,5-tetramethyl-2-(tetramethyl-1,3,2-dioxaborolan-2-yl)-1,3,2-dioxaborolane (343 mg, 1.4 mmol) in 1,4-dioxane (20 mL) stirred at r.t. under nitrogen, was added Pd(dppf)Cl$_2$ (100 mg, 0.1 mmol). The resulting mixture was stirred at 90° C. under nitrogen protection for 16 hrs. After the reaction was cooled down, 8-bromo-7-fluoro-1-isopropyl-3-methyl-1,3-dihydro-2H-imidazo[4,5-c]cinnolin-2-one (475 mg, 1.4 mmol), $K_2CO_3$ (276 mg, 2 mmol) and $H_2O$ (1 mL) were added, followed by Pd(dppf)Cl$_2$ (100 mg, 0.1 mmol). After stirred at 100° C. under nitrogen protection for 4 hrs, the crude mixture was cooled down, diluted with EtOAc (20 mL), washed with water and brine, dried over anhydrous $Na_2SO_4$, filtered and concentrated. The residue was purified by column chromatography on silica gel (DCM:MeOH=20:1 to 10:1) to give the crude product, which was further purified by Prep-TLC (DCM:MeOH=10:1) to give the desired product (30 mg, 5% yield) as a light yellow solid. MS: m/z 439[M+H]+. 1H NMR (400 MHz, CDCl3) δ 8.86 (s, 1H), 8.18 (d, J=11.1 Hz, 3H), 7.62 (s, 1H), 5.15 (s, 1H), 4.83 (s, 2H), 4.05 (t, J=5.0 Hz, 2H), 3.76 (s, 3H), 3.15 (s, 2H), 2.77 (s, 6H), 1.76 (s, 6H).

Example 7

7-fluoro-1-isopropyl-3-methyl-8-(6-((2-(piperidin-1-yl)ethoxy)methyl)pyridin-3-yl)-1H-imidazo[4,5-c]cinnolin-2(3H)-one

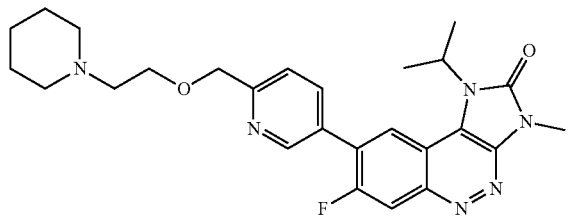 [SMILES: CC(C)n1c(=O)n(C)c2nnc3cc(F)c(-c4ccc(COCCN5CCCCC5)nc4)cc3c21]

The title compound was prepared using similar procedure as in Example 6 to give the desired product (5% yield) as a yellow solid. MS: 479 [M+H]+. 1H NMR (400 MHz, CDCl3) δ 8.85 (s, 1H), 8.24-8.15 (m, 2H), 8.03 (dt, J=8.2, 2.2 Hz, 1H), 7.61 (d, J=8.1 Hz, 1H), 5.20-5.10 (m, 1H), 4.78 (s, 2H), 4.14 (t, J=4.8 Hz, 2H), 3.76 (s, 3H), 3.27-3.04 (m, 6H), 2.01 (s, 4H), 1.76 (d, J=6.9 Hz, 6H), 1.63 (s, 2H).

Example 8

7-fluoro-1-isopropyl-3-methyl-8-(6-((2-(pyrrolidin-1-yl)ethoxy)methyl)pyridin-3-yl)-1H-imidazo[4,5-c]cinnolin-2(3H)-one

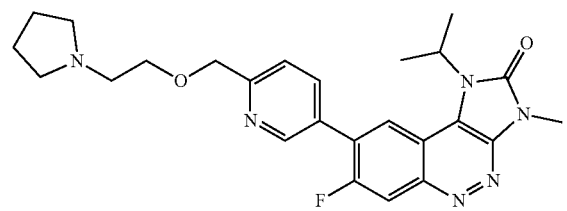

The title compound was prepared using similar procedure as in Example 6 to give the desired product (5% yield) as a yellow solid. MS: 465[M+H]+. 1H NMR (400 MHz, CDCl3) δ 8.87 (s, 1H), 8.19 (dd, J=9.3, 6.7 Hz, 2H), 8.05 (dt, J=8.3, 2.2 Hz, 1H), 7.65 (d, J=8.1 Hz, 1H), 5.24-5.08 (m, 1H), 4.82 (s, 2H), 4.15 (t, J=4.7 Hz, 2H), 3.76 (s, 3H), 3.38 (t, J=4.8 Hz, 6H), 2.16 (d, J=6.7 Hz, 4H), 1.76 (d, J=7.0 Hz, 6H).

Example 9

(R)-7-fluoro-8-(6-((2-(3-fluoropyrrolidin-1-yl)ethoxy)methyl)pyridin-3-yl)-1-isopropyl-3-methyl-1H-imidazo[4,5-c]cinnolin-2(3H)-one

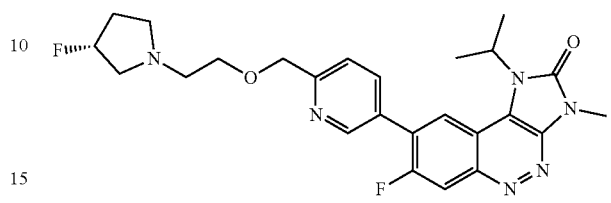

The title compound was prepared using similar procedure as in Example 6 to give the desired product (3% yield) as a yellow solid. MS: 483[M+H]+. 1H NMR (400 MHz, CDCl3) δ 8.84 (s, 1H), 8.19 (d, J=10.8 Hz, 2H), 8.04 (s, 1H), 7.65 (d, J=6.9 Hz, 1H), 5.38-5.06 (m, 2H), 4.80 (s, 2H), 3.91 (s, 2H), 3.76 (s, 3H), 3.37-2.89 (m, 6H), 2.19 (d, J=23.4 Hz, 2H), 1.76 (d, J=7.0 Hz, 6H).

Example 10

7-fluoro-8-(6-((2-(4-fluoropiperidin-1-yl)ethoxy)methyl)pyridin-3-yl)-1-isopropyl-3-methyl-1H-imidazo[4,5-c]cinnolin-2(3H)-one

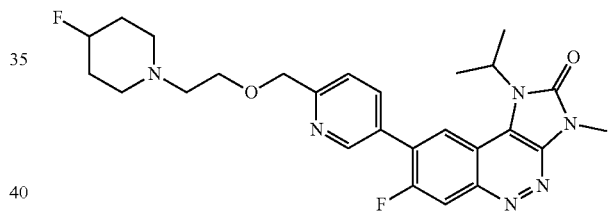

The title compound was prepared using similar procedure as in Example 6 to give the desired product (5% yield) as a yellow solid. MS: 497[M+H]+. 1H NMR (400 MHz, CDCl3) δ 8.84 (s, 1H), 8.25-8.12 (m, 2H), 8.03 (dt, J=8.2, 2.3 Hz, 1H), 7.63 (d, J=8.1 Hz, 1H), 5.22-5.08 (m, 1H), 4.78 (s, 3H), 3.94 (s, 2H), 3.76 (s, 3H), 2.92 (d, J=21.1 Hz, 6H), 2.18 (s, 2H), 2.01 (s, 2H), 1.76 (d, J=6.9 Hz, 6H).

Example 11

8-(6-((2-(3-azabicyclo[3.1.0]hexan-3-yl)ethoxy)methyl)pyridin-3-yl)-7-fluoro-1-isopropyl-3-methyl-1H-imidazo[4,5-c]cinnolin-2(3H)-one

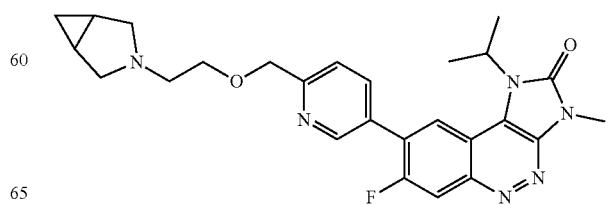

The title compound was prepared using similar procedure as in Example 6 to give the desired product (5% yield) as a yellow solid. MS: 477 [M+H]$^+$. $^1$H NMR (400 MHz, CDCl$_3$) δ 8.85 (s, 1H), 8.21-8.17 (m, 2H), 8.04 (dt, J=8.1, 2.2 Hz, 1H), 7.60 (d, J=8.1 Hz, 1H), 5.23-5.09 (m, 1H), 4.78 (s, 2H), 4.08 (s, 2H), 3.76 (s, 5H), 3.14 (d, J=54.5 Hz, 4H), 1.77 (d, J=6.9 Hz, 10H).

The following compounds were prepared according to the above described methods using different starting materials.

| Ex # | Structure | Name | MS m/z |
|---|---|---|---|
| 26 | 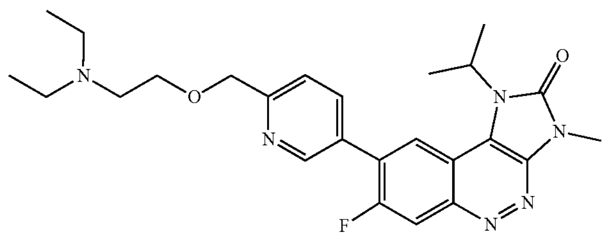 [SMILES: CCN(CC)CCOCc1ccc(-c2cc3c(cc2F)nnc2c3n(C(C)C)c(=O)n2C)cn1] | 8-(6-((2-(diethylamino)ethoxy)methyl)pyridin-3-yl)-7-fluoro-1-isopropyl-3-methyl-1,3-dihydro-2H-imidazo[4,5-c]cinnolin-2-one | 467 (M + H)$^+$ |
| 27 | 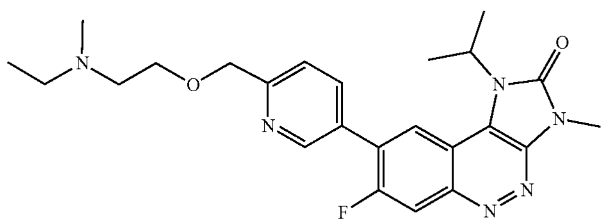 [SMILES: CCN(C)CCOCc1ccc(-c2cc3c(cc2F)nnc2c3n(C(C)C)c(=O)n2C)cn1] | 8-(6-((2-(ethyl(methyl)amino)ethoxy)methyl)pyridin-3-yl)-7-fluoro-1-isopropyl-3-methyl-1,3-dihydro-2H-imidazo[4,5-c]cinnolin-2-one | 453 (M + H)$^+$ |
| 28 | 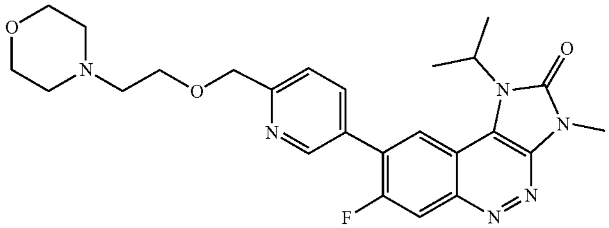 [SMILES: CC(C)n1c(=O)n(C)c2nnc3cc(F)c(-c4ccc(COCCN5CCOCC5)nc4)cc3c21] | 7-fluoro-1-isopropyl-3-methyl-8-(6-((2-morpholinoethoxy)methyl)pyridin-3-yl)-1,3-dihydro-2H-imidazo[4,5-c]cinnolin-2-one | 481 (M + H)$^+$ |
| 29 | 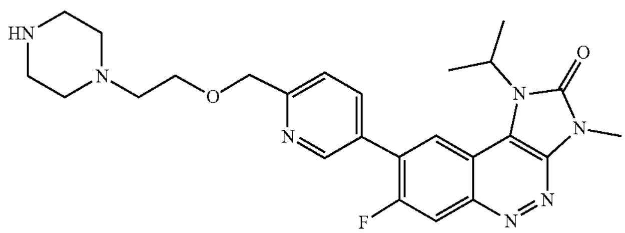 [SMILES: CC(C)n1c(=O)n(C)c2nnc3cc(F)c(-c4ccc(COCCN5CCNCC5)nc4)cc3c21] | 7-fluoro-1-isopropyl-3-methyl-8-(6-((2-(piperazin-1-yl)ethoxy)methyl)pyridin-3-yl)-1,3-dihydro-2H-imidazo[4,5-c]cinnolin-2-one | 480 (M + H)$^+$ |
| 30 | 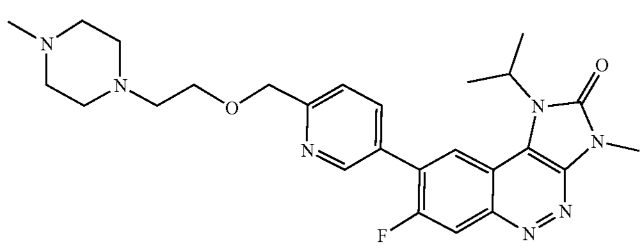 | 7-fluoro-1-isopropyl-3-methyl-8-(6-((2-(4-methylpiperazin-1-yl)ethoxy)methyl)pyridin-3-yl)-1,3-dihydro-2H-imidazo[4,5-c]cinnolin-2-one | 494 (M + H)$^+$ |

-continued

| Ex # | Structure | Name | MS m/z |
|---|---|---|---|
| 31 | 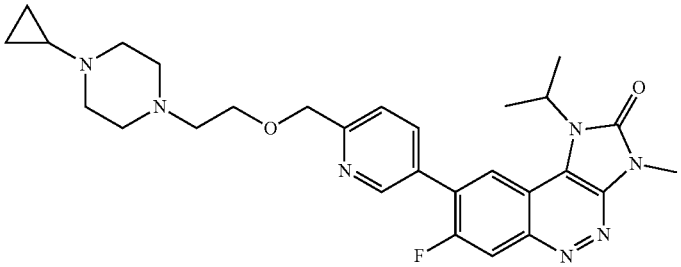 [SMILES: CC(C)n1c(=O)n(C)c2nnc3cc(F)c(-c4ccc(COCCN5CCN(C6CC6)CC5)nc4)cc3c21] | 8-(6-((2-(4-cyclopropylpiperazin-1-yl)ethoxy)methyl)pyridin-3-yl)-7-fluoro-1-isopropyl-3-methyl-1,3-dihydro-2H-imidazo[4,5-c]cinnolin-2-one | 520 (M + H)+ |
| 32 | 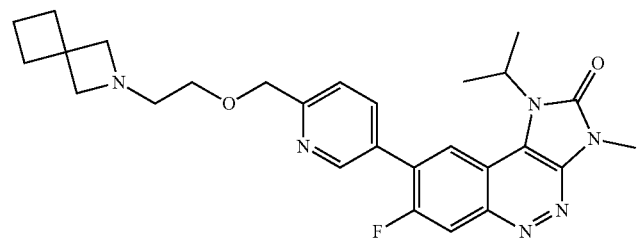 [SMILES: CC(C)n1c(=O)n(C)c2nnc3cc(F)c(-c4ccc(COCCN5CC6(CCC6)C5)nc4)cc3c21] | 8-(6-((2-(2-azaspiro[3.3]heptan-2-yl)ethoxy)methyl)pyridin-3-yl)-7-fluoro-1-isopropyl-3-methyl-1,3-dihydro-2H-imidazo[4,5-c]cinnolin-2-one | 491 (M + H)+ |
| 33 | 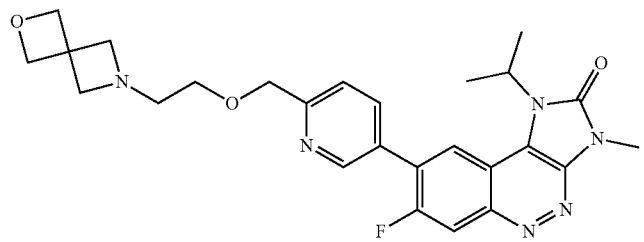 [SMILES: CC(C)n1c(=O)n(C)c2nnc3cc(F)c(-c4ccc(COCCN5CC6(COC6)C5)nc4)cc3c21] | 8-(6-((2-(2-oxa-6-azaspiro[3.3]heptan-6-yl)ethoxy)methyl)pyridin-3-yl)-7-fluoro-1-isopropyl-3-methyl-1,3-dihydro-2H-imidazo[4,5-c]cinnolin-2-one | 493 (M + H)+ |
| 34 | 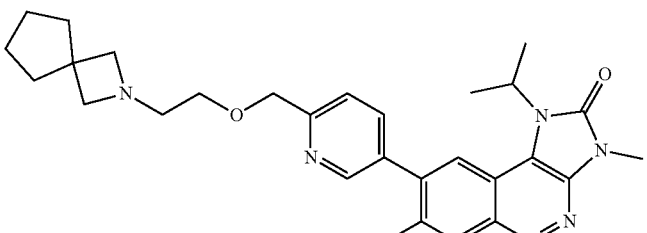 | 8-(6-((2-(2-azaspiro[3.4]octan-2-yl)ethoxy)methyl)pyridin-3-yl)-7-fluoro-1-isopropyl-3-methyl-1,3-dihydro-2H-imidazo[4,5-c]cinnolin-2-one | 505 (M + H)+ |
| 35 | 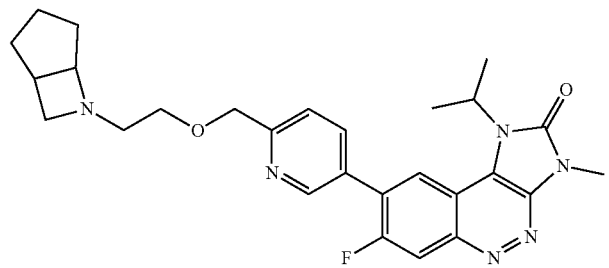 [SMILES: CC(C)n1c(=O)n(C)c2nnc3cc(F)c(-c4ccc(COCCN5CC6CCCC65)nc4)cc3c21] | 8-(6-((2-(6-azabicyclo[3.2.0]heptan-6-yl)ethoxy)methyl)pyridin-3-yl)-7-fluoro-1-isopropyl-3-methyl-1,3-dihydro-2H-imidazo[4,5-c]cinnolin-2-one | 491 (M + H)+ |

Example 12

N-(2-(dimethylamino)ethyl)-5-(7-fluoro-1-isopropyl-3-methyl-2-oxo-2,3-dihydro-1H-imidazo[4,5-c]cinnolin-8-yl)picolinamide Compound of Example 12 was prepared according to the synthetic route shown in Scheme 4:

Scheme 4

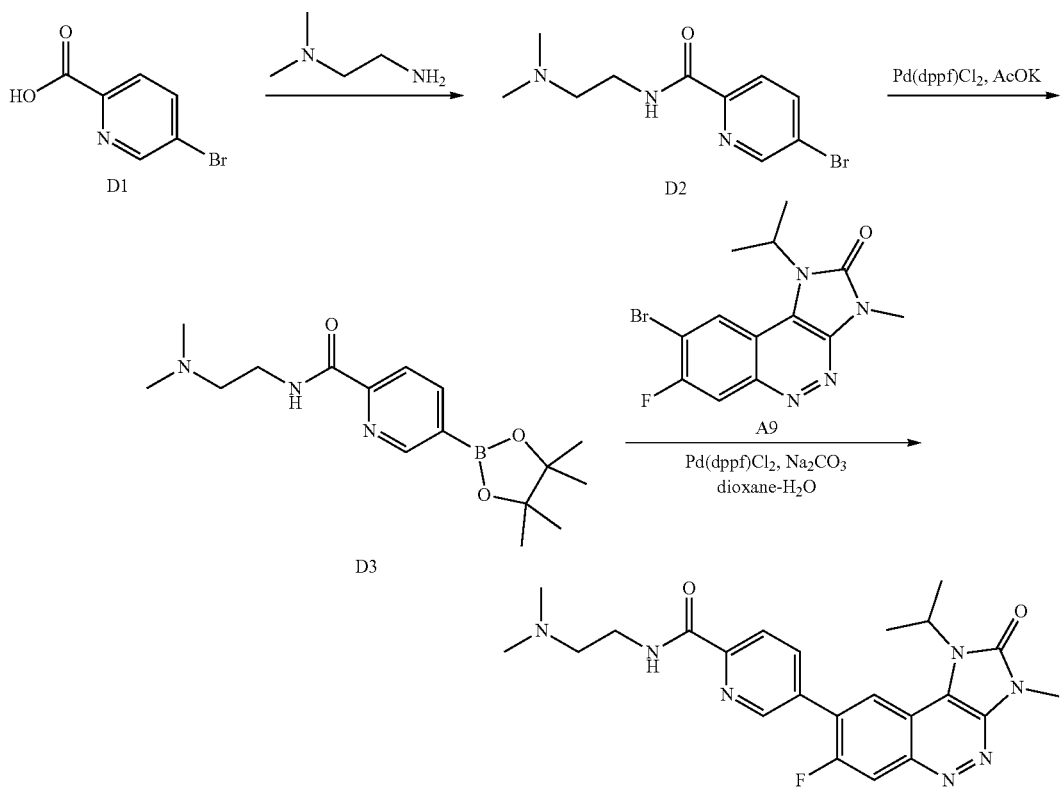

Step 1: 5-bromo-N-(2-(dimethylamino)ethyl)picolinamide (D2)

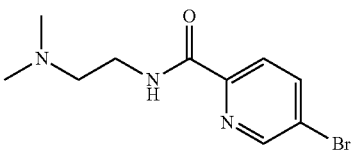

To a solution of 5-bromopicolinic acid (250 mg, 1.2 mmol) in DMF (20 mL) was added HOBt (140 mg, 1.2 mmol), EDCI (400 mg, 2 mmol) and DIPEA (330 mg, 3 mmol), and the reaction mixture was stirred at r.t. for 30 min. Then to the mixture was added N',N'-dimethylethane-1,2-diamine (170 mg, 2 mmol). The reaction mixture was stirred at r.t. for 12 hrs and then poured into ice water. The resulting mixture was extracted with EtOAc twice. The combined organic layers were washed with brine, dried over anhydrous Na$_2$SO$_4$ and concentrated under reduced pressure to give crude product (250 mg) as brown oil, which was used for next step without further purification. MS: m/z 272 [M+H]$^+$.

Step 2&3: N-(2-(dimethylamino)ethyl)-5-(7-fluoro-1-isopropyl-3-methyl-2-oxo-2,3-dihydro-1H-imidazo[4,5-c]cinnolin-8-yl)picolinamide

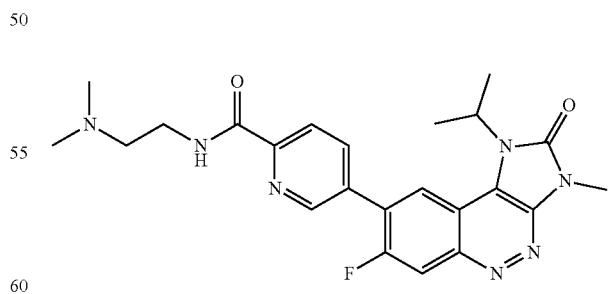

To a mixture of 5-bromo-N-(2-(dimethylamino)ethyl)picolinamide (50 mg, 0.2 mmol) and 4,4,5,5-tetramethyl-2-(tetramethyl-1,3,2-dioxaborolan-2-yl)-1,3,2-dioxaborolane (44 mg, 0.2 mmol) in 1,4-dioxane (20 mL) were added KOAc (60 mg, 0.6 mmol) and Pd(dppf)Cl$_2$ (20 mg, 0.02 mmol). The reaction mixture was stirred at 90° C. under N$_2$ protection for 12 hrs. After the mixture was cooed down, water (1 mL), 8-bromo-7-fluoro-1-isopropyl-3-methyl-1,3-dihydro-2H-imidazo[4,5-c]cinnolin-2-one (68 mg, 0.2 mmol), $K_2CO_3$ (180 mg, 1 mmol) and Pd(dppf)$Cl_2$ (20 mg, 0.05 mmol) were added to the mixture. The reaction mixture was stirred at 100° C. for another 4 hrs and then filtered. The filtrate was partitioned with EtOAc and water. The separated organic layer was washed with brine, dried over anhydrous $Na_2SO_4$ and concentrated under reduced pressure. The residue was purified by chromatography on silica gel (DCM: MeOH=20:1 to 10:1) to give crude product, which was further purified by Prep-TLC (DCM:MeOH=10:1 to EtOAc: MeOH=1:1) to give desired product (16 mg, 19% yield) as a light yellow solid. MS: m/z 452[M+H]$^+$. $^1$H NMR (400 MHz, CDCl$_3$) δ 8.84 (d, J=1.9 Hz, 1H), 8.53 (t, J=5.7 Hz, 1H), 8.35 (d, J=8.1 Hz, 1H), 8.22-8.11 (m, 3H), 5.23-5.05 (m, 1H), 3.76 (s, 3H), 3.71 (q, J=6.0 Hz, 2H), 2.76 (t, J=6.0 Hz, 2H), 2.45 (s, 6H), 1.76 (d, J=7.0 Hz, 6H).

Example 13

7-fluoro-8-(6-(3-(4-fluoropiperidin-1-yl)propoxy) pyridin-3-yl)-1-isopropyl-3-methyl-1H-imidazo[4,5-c]cinnolin-2(3H)-one Compound of Example 13 was prepared according to the synthetic route shown in Scheme 5:

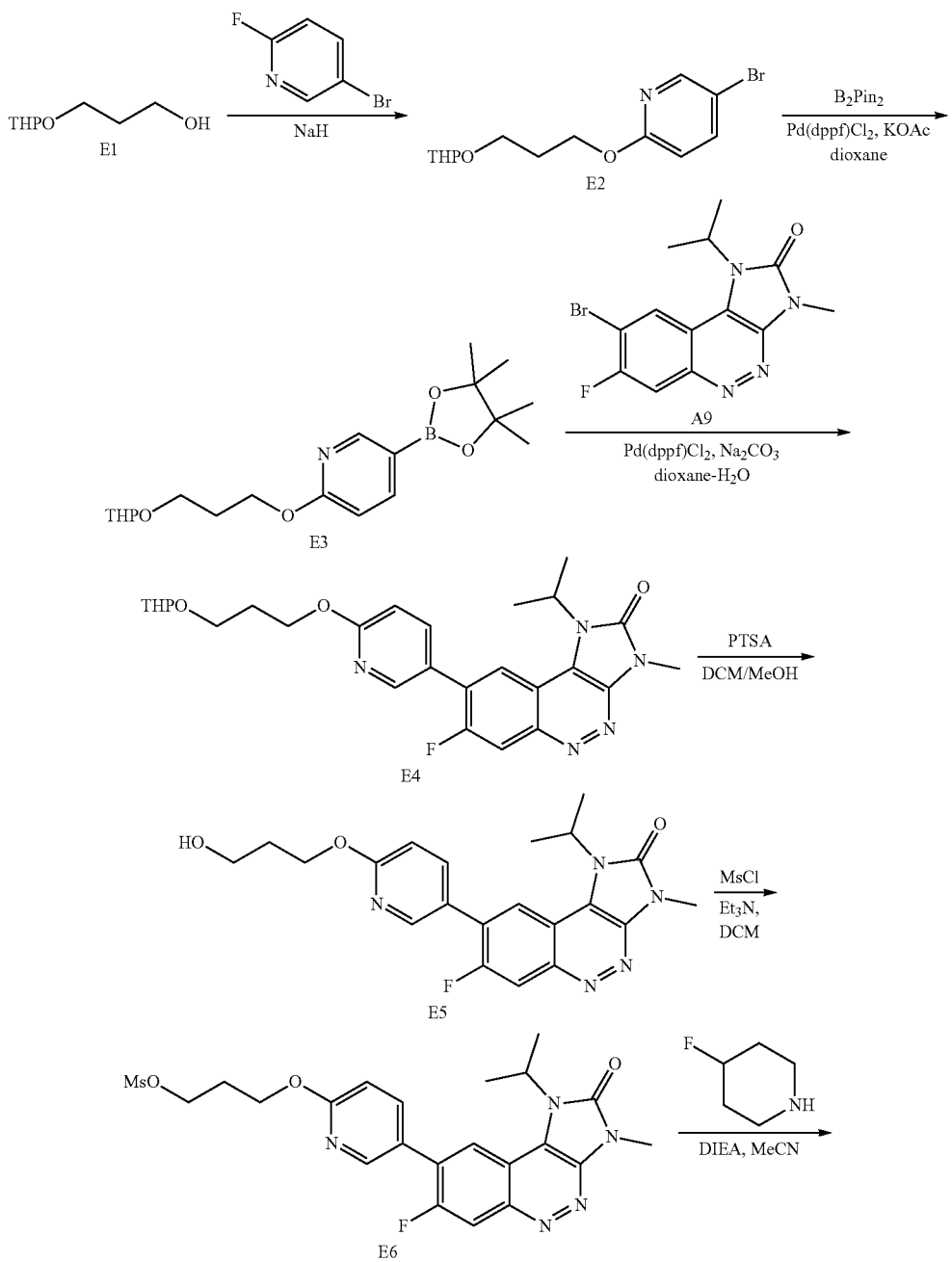

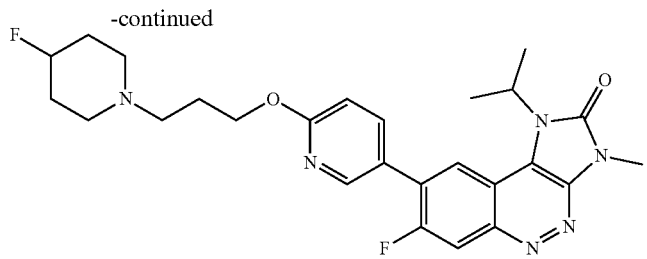

Step 1: 3-((tetrahydro-2H-pyran-2-yl)oxy)propan-1-ol (E2)

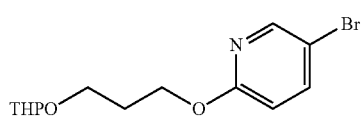

To a solution of 3-((tetrahydro-2H-pyran-2-yl)oxy)propan-1-ol (1.9 g, 11.9 mmol) in anhydrous THF (20 mL) stirred at 0° C. under nitrogen, was added NaH (477 mg, 11.9 mmol) portionwise. The resulting mixture was stirred at r.t. for 30 min, and then 5-bromo-2-fluoropyridine (1 g, 6 mmol) was added thereto. After stirred at r.t. for 16 hrs, the crude mixture was then poured in ice water and extracted with EtOAc (50 mL×2). The combined organic phases were washed with water and brine, dried over anhydrous Na$_2$SO$_4$, filtered and concentrated. The residue was purified by column chromatography on silica gel to give the desired product 3-((tetrahydro-2H-pyran-2-yl)oxy)propan-1-ol (1.2 g, 63% yield). MS: 316 [M+H]$^+$.

Step 2&3: 7-fluoro-1-isopropyl-3-methyl-8-(6-(3-((tetrahydro-2H-pyran-2-yl)oxy)propoxy)pyridin-3-yl)-1H-imidazo[4,5-c]cinnolin-2(3H)-one (E4)

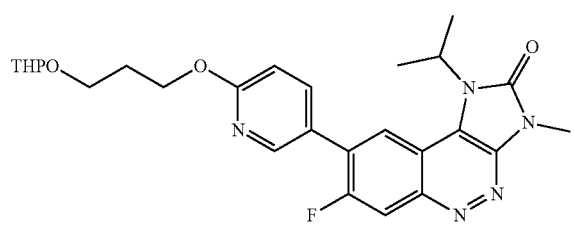

To a solution of 5-bromo-2-(3-((tetrahydro-2H-pyran-2-yl)oxy)propoxy)pyridine (200 mg, 0.635 mmol), B$_2$Pin$_2$ (194 mg, 0.76 mmol), and KOAc (187 mg, 1.9 mmol) in dioxane (5 mL) stirred at r.t. under nitrogen, was added Pd(dppf)Cl$_2$·CH$_2$Cl$_2$ (52 mg, 0.064 mol). The resulting mixture was stirred at 80° C. under N$_2$ protection for 16 hrs. After the reaction was cooled down, 8-bromo-7-fluoro-1-isopropyl-3-methyl-1,3-dihydro-2H-imidazo[4,5-c]cinnolin-2-one (215 mg, 0.635 mmol), Pd(dppf)Cl$_2$·CH$_2$Cl$_2$ (52 mg, 0.064 mmol), Na$_2$CO$_3$ (200 mg, 1.9 mmol) and H$_2$O (1 mL) were added. The resulting mixture was stirred at 100° C. under N$_2$ protection for another 4 hrs. The crude mixture was concentrated to dryness and the residue was purified by column chromatography on silica gel to give the desired product (280 mg, 89% yield) as a dark solid. MS: 496 [M+H]$^+$.

Step 4: 7-fluoro-8-(6-(3-hydroxypropoxy)pyridin-3-yl)-1-isopropyl-3-methyl-1H-imidazo[4,5-c]cinnolin-2(3H)-one (E5)

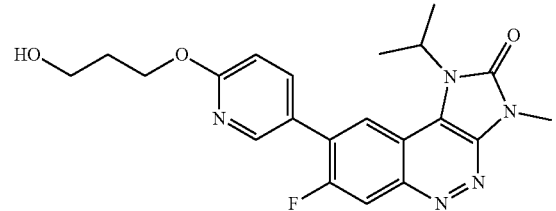 [SMILES: CC(C)n1c(=O)n(C)c2nnc3cc(F)c(-c4ccc(OCCCO)nc4)cc3c21]

To a solution of 7-fluoro-1-isopropyl-3-methyl-8-(6-(3-((tetrahydro-2H-pyran-2-yl)oxy)propoxy)pyridin-3-yl)-1,3-dihydro-2H-imidazo[4,5-c]cinnolin-2-one (332 mg, 0.67 mmol) in DCM/MeOH (3 mL/3 mL) stirred at r.t., was added PTSA (255 mg, 1.34 mmol). The resulting mixture was stirred at r.t. for 4 hrs. The crude mixture was diluted with DCM (20 mL), washed with aq. NaHCO$_3$, water and brine. The organic layer was dried over anhydrous Na$_2$SO$_4$, filtered and concentrated to give the desired product (220 mg, 80% yield), which was used for next step without further purification. LCMS: 412 [M+H]$^+$.

Step 4: 3-((5-(7-fluoro-1-isopropyl-3-methyl-2-oxo-2,3-dihydro-1H-imidazo[4,5-c]cinnolin-8-yl)pyridin-2-yl)oxy)propyl methanesulfonate (E6)

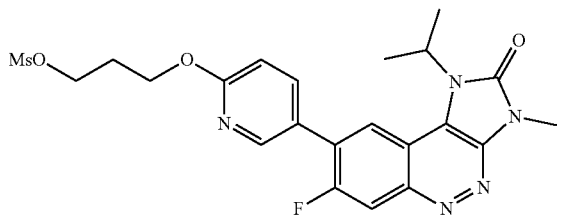 [SMILES: CC(C)n1c(=O)n(C)c2nnc3cc(F)c(-c4ccc(OCCCOS(C)(=O)=O)nc4)cc3c21]

To a solution of 7-fluoro-8-(6-(3-hydroxypropoxy)pyridin-3-yl)-1-isopropyl-3-methyl-1,3-dihydro-2H-imidazo[4,5-c]cinnolin-2-one (201 mg, 0.49 mmol) and Et$_3$N (150 mg, 1.47 mmol) in DCM (3 mL) was added MsCl (112 mg, 0.97 mmol) dropwise at 0° C. The resulting mixture was stirred at r.t. for 60 min and then diluted with DCM (15 mL). The organic phase was washed with water and brine, dried over anhydrous Na$_2$SO$_4$, filtered and concentrated to give the crude product (340 mg, 100% yield), which was used for next step without further purification. MS: 490 [M+H]⁺.

Step 5: 7-fluoro-8-(6-(3-(4-fluoropiperidin-1-yl)propoxy)pyridin-3-yl)-1-isopropyl-3-methyl-1H-imidazo[4,5-c]cinnolin-2(3H)-one

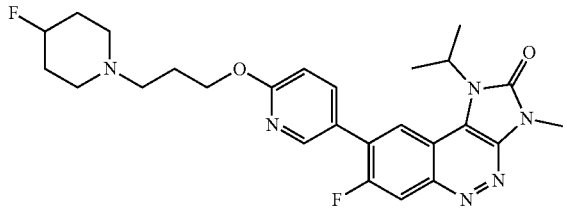 [SMILES: CC(C)n1c(=O)n(C)c2nnc3cc(F)c(-c4ccc(OCCCN5CCC(F)CC5)nc4)cc3c21]

To a solution of 3-((5-(7-fluoro-1-isopropyl-3-methyl-2-oxo-2,3-dihydro-1H-imidazo[4,5-c]cinnolin-8-yl)pyridin-2-yl)oxy)propyl methanesulfonate (170 mg, 0.32 mmol) and DIEA (206 mg, 1.6 mmol) in MeCN (5 mL) stirred at r.t., was added 4-fluoropiperidine (180 mg, 1.28 mmol) in one portion. The resulting mixture was stirred at r.t. for 16 hrs and then diluted DCM (20 mL). The organic phase was washed with water and brine, dried over anhydrous Na₂SO₄, filtered and concentrated. The residue was purified by prep-TLC to give the desired product (10 mg, 6% yield) as a yellow solid. MS: 497 [M+H]⁺. ¹H NMR (400 MHz, CD₃OD) δ 8.31 (d, J=7.7 Hz, 1H), 8.21 (d, J=2.6 Hz, 1H), 8.00 (d, J=11.5 Hz, 1H), 7.91 (dt, J=9.4, 2.3 Hz, 1H), 6.71 (d, J=9.4 Hz, 1H), 5.37-5.21 (m, 1H), 4.79-4.65 (m, 1H), 4.21 (t, J=7.0 Hz, 2H), 3.66 (s, 3H), 2.95-2.62 (m, 6H), 2.14 (t, J=7.2 Hz, 2H), 2.08-1.85 (m, 5H), 1.75 (d, J=6.8 Hz, 6H).

Example 14

(S)-7-fluoro-8-(6-(3-(3-fluoropyrrolidin-1-yl)propoxy)pyridin-3-yl)-1-isopropyl-3-methyl-1H-imidazo[4,5-c]cinnolin-2(3H)-one

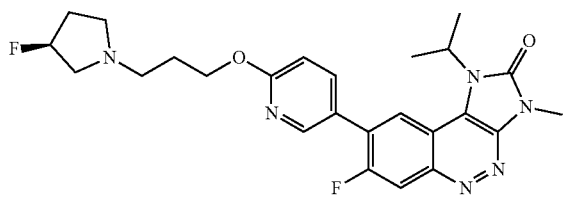 [SMILES: CC(C)n1c(=O)n(C)c2nnc3cc(F)c(-c4ccc(OCCCN5CC[C@@H](F)C5)nc4)cc3c21]

The title compound was prepared using similar procedure as in Example 13 to give the desired product (20% yield) as a yellow solid. MS: 482 [M+H]⁺. ¹H NMR (400 MHz, CD₃OD) δ 8.30 (d, J=7.6 Hz, 1H), 8.21 (d, J=2.5 Hz, 1H), 7.98 (d, J=11.5 Hz, 1H), 7.91 (dt, J=9.4, 2.3 Hz, 1H), 6.71 (d, J=9.4 Hz, 1H), 5.35-5.19 (m, 2H), 4.22 (t, J=7.0 Hz, 2H), 3.66 (s, 3H), 3.23 (td, J=12.0, 10.1, 7.2 Hz, 2H), 3.08-2.83 (m, 4H), 2.31-2.09 (m, 4H), 1.75 (d, J=6.8 Hz, 6H).

Example 15

(R)-7-fluoro-8-(6-(3-(3-fluoropyrrolidin-1-yl)propoxy)pyridin-3-yl)-1-isopropyl-3-methyl-1H-imidazo[4,5-c]cinnolin-2(3H)-one

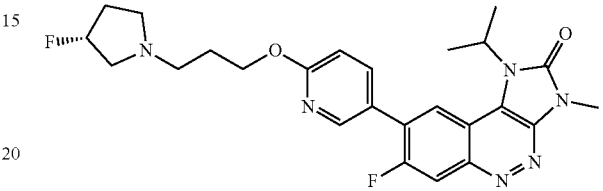

The title compound was prepared using similar procedure as in Example 13 to give the desired product (21% yield) as a yellow solid. LCMS: 482 [M+H]⁺. H NMR (400 MHz, CD₃OD) δ 8.30 (d, J=7.7 Hz, 1H), 8.21 (d, J=2.6 Hz, 1H), 7.98 (d, J=11.5 Hz, 1H), 7.90 (dt, J=9.4, 2.4 Hz, 1H), 6.70 (d, J=9.4 Hz, 1H), 5.34-5.22 (m, 2H), 4.22 (t, J=7.0 Hz, 2H), 3.66 (s, 3H), 3.24-3.12 (m, 2H), 2.99-2.74 (m, 4H), 2.28-2.05 (m, 4H), 1.75 (d, J=6.8 Hz, 6H).

Example 16

8-(6-(3-(3-azabicyclo[3.1.0]hexan-3-yl)propoxy)pyridin-3-yl)-7-fluoro-1-isopropyl-3-methyl-1H-imidazo[4,5-c]cinnolin-2(3H)-one

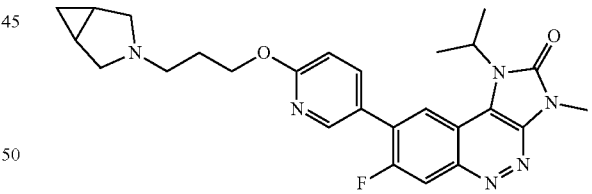

The title compound was prepared using similar procedure as in Example 13 to give the desired product (24% yield) as a yellow solid. MS: 477 [M+H]⁺. ¹H NMR (400 MHz, CD₃OD) δ 8.32 (d, J=7.6 Hz, 1H), 8.19 (d, J=2.6 Hz, 1H), 8.00 (d, J=11.5 Hz, 1H), 7.93 (dt, J=9.4, 2.3 Hz, 1H), 6.73 (d, J=9.4 Hz, 1H), 5.29 (h, J=6.7 Hz, 1H), 4.22 (t, J=6.9 Hz, 2H), 3.66 (s, 3H), 3.44 (d, J=10.5 Hz, 2H), 3.13-2.98 (m, 4H), 2.24-2.14 (m, 2H), 1.75 (d, J=6.8 Hz, 8H), 0.72 (t, J=5.0 Hz, 2H).

The following compounds were prepared according to the above described methods using different starting materials.

| Ex # | Structure | Name | MS m/z |
|---|---|---|---|
| 36 | 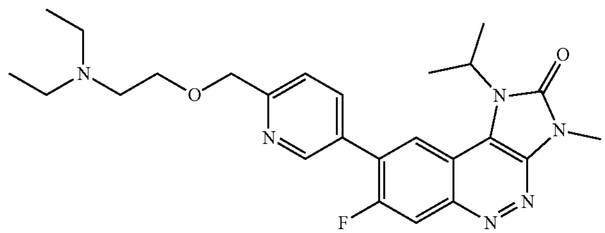 [SMILES: CCN(CC)CCOCc1ccc(-c2cc3c(cc2F)nnc2c3n(C(C)C)c(=O)n2C)cn1] | 8-(6-(3-(diethylamino)propoxy)pyridin-3-yl)-7-fluoro-1-isopropyl-3-methyl-1,3-dihydro-2H-imidazo[4,5-c]cinnolin-2-one | 467 (M + H)+ |
| 37 | 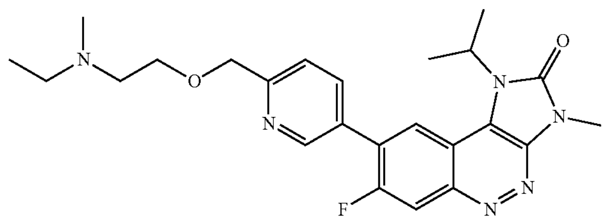 [SMILES: CCN(C)CCOCc1ccc(-c2cc3c(cc2F)nnc2c3n(C(C)C)c(=O)n2C)cn1] | 8-(6-(3-(ethyl(methyl)amino)propoxy)pyridin-3-yl)-7-fluoro-1-isopropyl-3-methyl-1,3-dihydro-2H-imidazo[4,5-c]cinnolin-2-one | 453 (M + H)+ |
| 38 | 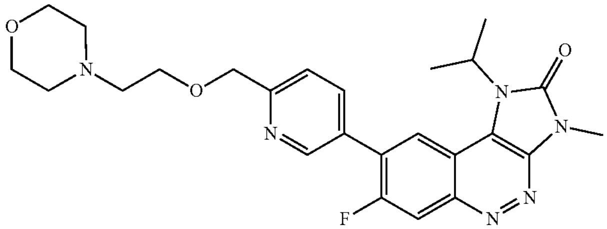 [SMILES: CC(C)n1c(=O)n(C)c2nnc3cc(F)c(-c4ccc(COCCN5CCOCC5)nc4)cc3c21] | 7-fluoro-1-isopropyl-3-methyl-8-(6-(3-morpholinopropoxy)pyridin-3-yl)-1,3-dihydro-2H-imidazo[4,5-c]cinnolin-2-one | 481 (M + H)+ |
| 39 | 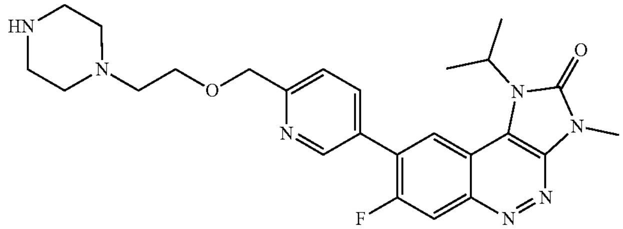 [SMILES: CC(C)n1c(=O)n(C)c2nnc3cc(F)c(-c4ccc(COCCN5CCNCC5)nc4)cc3c21] | 7-fluoro-1-isopropyl-3-methyl-8-(6-(3-(piperazin-1-yl)propoxy)pyridin-3-yl)-1,3-dihydro-2H-imidazo[4,5-c]cinnolin-2-one | 480 (M + H)+ |
| 40 | 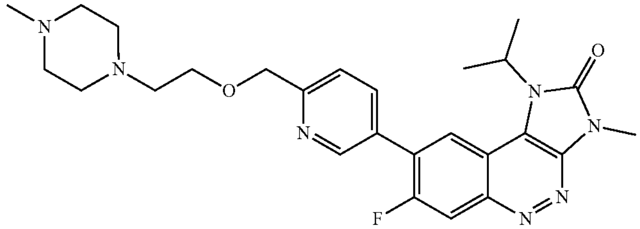 | 7-fluoro-1-isopropyl-3-methyl-8-(6-(3-(4-methylpiperazin-1-yl)propoxy)pyridin-3-yl)-1,3-dihydro-2H-imidazo[4,5-c]cinnolin-2-one | 494 (M + H)+ |
| 41 | 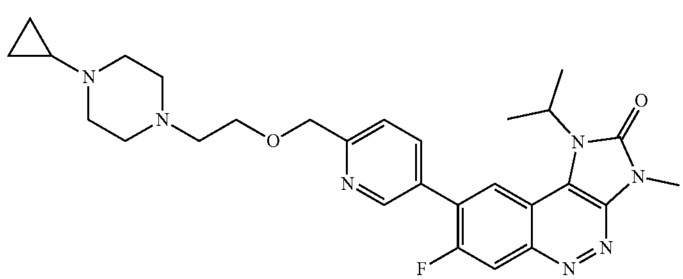 [SMILES: CC(C)n1c(=O)n(C)c2nnc3cc(F)c(-c4ccc(COCCN5CCN(C6CC6)CC5)nc4)cc3c21] | 8-(6-(3-(4-cyclopropylpiperazin-1-yl)propoxy)pyridin-3-yl)-7-fluoro-1-isopropyl-3-methyl-1,3-dihydro-2H-imidazo[4,5-c]cinnolin-2-one | 520 (M + H)+ |

-continued

| Ex # | Structure | Name | MS m/z |
|---|---|---|---|
| 42 | 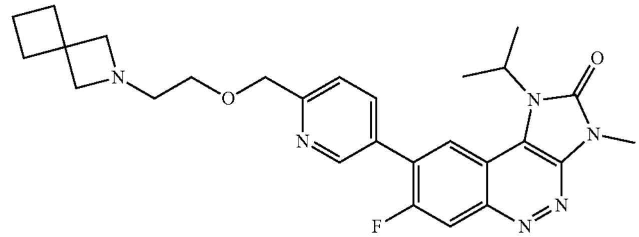 [SMILES: CC(C)n1c(=O)n(C)c2nnc3cc(F)c(-c4ccc(COCCN5CC6(CCC6)C5)nc4)cc3c21] | 8-(6-(3-(2-azaspiro[3.3]heptan-2-yl)propoxy)pyridin-3-yl)-7-fluoro-1-isopropyl-3-methyl-1,3-dihydro-2H-imidazo[4,5-c]cinnolin-2-one | 491 (M + H)+ |
| 43 | 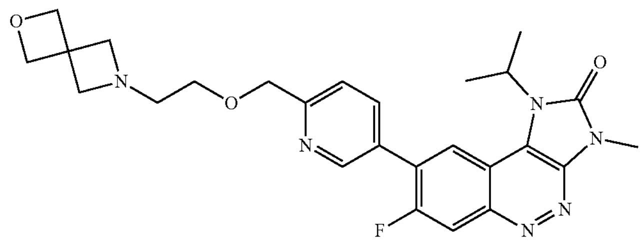 [SMILES: CC(C)n1c(=O)n(C)c2nnc3cc(F)c(-c4ccc(COCCN5CC6(COC6)C5)nc4)cc3c21] | 8-(6-(3-(2-oxa-6-azaspiro[3.3]heptan-6-yl)propoxy)pyridin-3-yl)-7-fluoro-1-isopropyl-3-methyl-1,3-dihydro-2H-imidazo[4,5-c]cinnolin-2-one | 493 (M + H)+ |
| 44 | 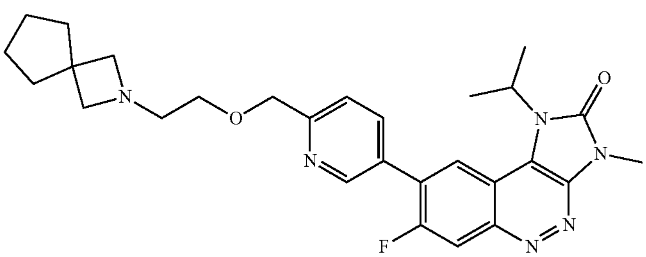 [SMILES: CC(C)n1c(=O)n(C)c2nnc3cc(F)c(-c4ccc(COCCN5CC6(CCCC6)C5)nc4)cc3c21] | 8-(6-(3-(2-azaspiro[3.4]octan-2-yl)propoxy)pyridin-3-yl)-7-fluoro-1-isopropyl-3-methyl-1,3-dihydro-2H-imidazo[4,5-c]cinnolin-2-one | 505 (M + H)+ |
| 45 | 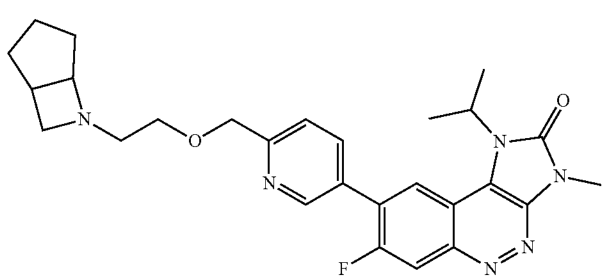 [SMILES: CC(C)n1c(=O)n(C)c2nnc3cc(F)c(-c4ccc(COCCN5CC6CCCC65)nc4)cc3c21] | 8-(6-(3-(6-azabicyclo[3.2.0]heptan-6-yl)propoxy)pyridin-3-yl)-7-fluoro-1-isopropyl-3-methyl-1,3-dihydro-2H-imidazo[4,5-c]cinnolin-2-one | 491 (M + H)+ |

Example 17

8-(6-(3-(dimethylamino)propoxy)-2-fluoropyridin-3-yl)-7-fluoro-1-isopropyl-3-methyl-1,3-dihydro-2H-imidazo[4,5-c]cinnolin-2-one

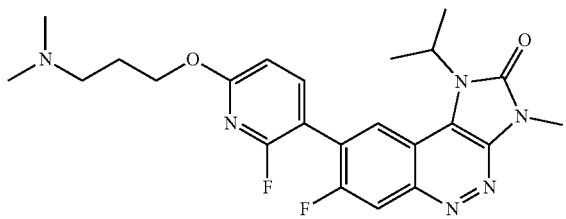

The title compound was prepared using similar procedure as in Example 1. MS: m/z 457[M+H]$^+$. $^1$H NMR (400 MHz, CDCl$_3$) δ 8.22 (d, J=7.2 Hz, 1H), 8.16 (d, J=10.8 Hz, 1H), 7.88 (ddd, J=10.0, 8.4, 2.0 Hz, 1H), 6.91-6.74 (m, 1H), 5.27-5.01 (m, 1H), 4.43 (t, J=6.4 Hz, 2H), 3.76 (s, 3H), 2.52 (t, J=7.4 Hz, 2H), 2.32 (s, 6H), 2.08-1.98 (m, 2H), 1.75 (d, J=7.0 Hz, 6H).

Example 18

7-fluoro-3-methyl-8-(6-(3-(piperidin-1-yl)propoxy)pyridin-3-yl)-1-(tetrahydro-2H-pyran-4-yl)-1H-imidazo[4,5-c]cinnolin-2(3H)-one Compound of Example 18 was prepared according to the synthetic route shown in Scheme 6:

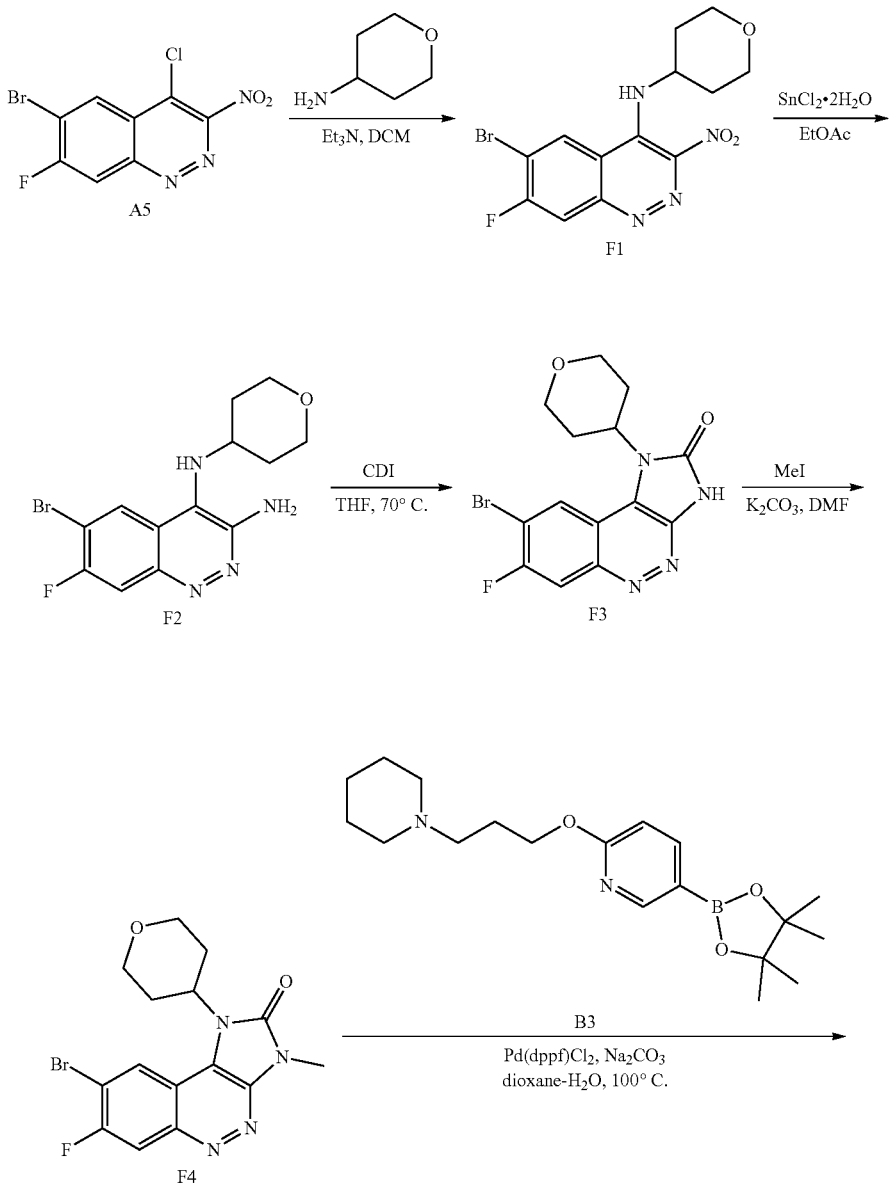

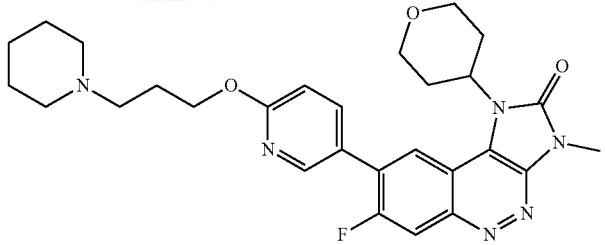

Step 1: 6-bromo-7-fluoro-3-nitro-N-(tetrahydro-2H-pyran-4-yl)cinnolin-4-amine (F1)

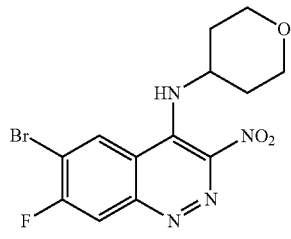 [SMILES: O=[N+]([O-])c1nnc2cc(F)c(Br)cc2c1NC1CCOCC1]

To a solution of 6-bromo-4-chloro-7-fluoro-3-nitrocinnoline (1 g, 3.28 mmol) and Et₃N (1.4 mL, 9.8 mmol) in DCM (15 mL) stirred at r.t., was added tetrahydro-2H-pyran-4-amine (497 mg, 4.9 mmol). The resulting mixture was stirred at r.t. for 16 hrs and concentrated. The residue was purified by chromatography on silica gel to give the desired product (800 mg, 65% yield) as a yellow solid. MS: m/z 371 [M+H]⁺.

Step 2: 6-bromo-7-fluoro-N4-(tetrahydro-2H-pyran-4-yl)cinnoline-3,4-diamine (F2)

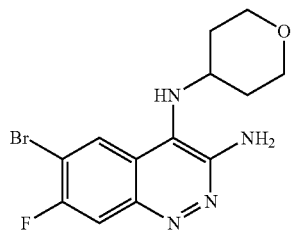

To a solution of 6-bromo-7-fluoro-3-nitro-N-(tetrahydro-2H-pyran-4-yl)cinnolin-4-amine (900 mg, 2.43 mmol) in EtOAc (20 mL) stirred at r.t., was added SnCl₂·2H₂O (2.2 g, 9.7 mmol). The resulting mixture was stirred at 80° C. for 2 hrs. The crude mixture was basified with aq. NaHCO₃ to adjust pH=9 and then the precipitate was filtered off. The filtrate was diluted with EtOAc (20 mL) and the organic phase was washed with water and brine, filtered and concentrated. The residue was purified by column chromatography on silica gel to give the desired product (750 mg, 90% yield) as a yellow solid. MS: m/z 341 [M+H]⁺.

Step 3: 8-bromo-7-fluoro-1-(tetrahydro-2H-pyran-4-yl)-1H-imidazo[4,5-c]cinnolin-2(3H)-one (F3)

To a solution of 6-bromo-7-fluoro-N4-(tetrahydro-2H-pyran-4-yl)cinnoline-3,4-diamine (900 mg, 2.65 mmol) in THF (20 mL) stirred at r.t., was added CDI (2.2 g, 13.3 mmol). The resulting mixture was stirred at 70° C. for 16 hrs and then concentrated. The residue was poured into ice water, and then the precipitate was collected by filtration. The solid was washed with water, dried under vacuum to give the desired product (800 mg, 82% yield) as a yellow solid. MS: m/z 367 [M+H]⁺.

Step 4: 8-bromo-7-fluoro-3-methyl-1-(tetrahydro-2H-pyran-4-yl)-1H-imidazo[4,5-c]cinnolin-2(3H)-one (F4)

To a solution of 8-bromo-7-fluoro-1-(tetrahydro-2H-pyran-4-yl)-1H-imidazo[4,5-c]cinnolin-2(3H)-one (800 mg, 2.18 mmol) in DMF (3 mL) stirred at r.t., was added K₂CO₃ (905 mg, 6.56 mmol), the resulting mixture was stirred at 40° C. for 2 hrs. The reaction mixture was cooled to 0° C., MeI (774 mg, 5.45 mmol) was added thereto dropwise. The resulting mixture was stirred at r.t. for another 2 hrs and then poured into ice water. The precipitate was collected by filtration, washed with water and dried under vacuum to give the desired product (500 mg, 60% yield) as a yellow solid. MS: m/z 381 [M+H]⁺.

Step 5: 7-fluoro-1-isopropyl-3-methyl-8-(6-(3-(piperidin-1-yl)propoxy)pyridin-3-yl)-1H-imidazo[4,5-c]cinnolin-2(3H)-one

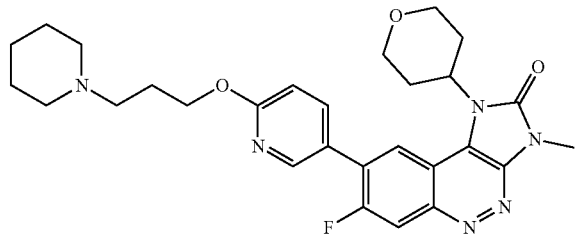 [SMILES: Cn1c(=O)n(C2CCOCC2)c2c3cc(-c4ccc(OCCCN5CCCCC5)nc4)c(F)cc3nnc21]

To a solution of 8-bromo-7-fluoro-3-methyl-1-(tetrahydro-2H-pyran-4-yl)-1H-imidazo[4,5-c]cinnolin-2(3H)-one (50 mg, 0.132 mmol), 2-(3-(piperidin-1-yl)propoxy)-5-(4,4,5,5-tetramethyl-1,3,2-dioxaborolan-2-yl)pyridine (46 mg, 0.132 mmol) and Na$_2$CO$_3$ (42 mg, 0.4 mmol) in dioxane/H$_2$O (2 mL/0.5 mL) stirred at r.t. under nitrogen, was added Pd(dppf)Cl$_2$ (11 mg, 0.0132 mmol). The resulting mixture was stirred at 100° C. for 16 hrs. The crude mixture was then filtered and the filtrate was concentrated. The residue was purified by prep-TLC to give the desired product (18 mg, 26% yield) as a yellow solid. MS: 521 [M+H]$^+$. $^1$H NMR (400 MHz, CDCl$_3$) δ 8.44 (s, 1H), 8.26 (d, J=7.4 Hz, 1H), 8.17 (d, J=11.2 Hz, 1H), 7.93 (d, J=8.8 Hz, 1H), 6.90 (d, J=8.8 Hz, 1H), 5.02 (s, 1H), 4.51 (t, J=5.8 Hz, 2H), 4.24 (m, 2H), 3.78 (s, 3H), 3.61 (t, J=11.8 Hz, 2H), 3.17 (t, J=8.4 Hz, 2H), 2.85-2.70 (m, 2H), 2.51-2.46 (m, 2H), 2.22-1.63 (m, 12H).

Example 19

8-(6-(3-(dimethylamino)propoxy)pyridin-3-yl)-7-fluoro-3-methyl-1-(tetrahydro-2H-pyran-4-yl)-1H-imidazo[4,5-c]cinnolin-2(3H)-one

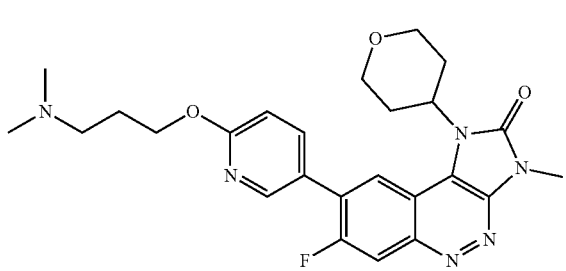

The title compound was prepared using similar procedure as in Example 18. MS: 481[M+H]$^+$. $^1$H NMR (400 MHz, CDCl$_3$) δ 8.44 (s, 1H), 8.27 (d, J=7.4 Hz, 1H), 8.18 (d, J=11.2 Hz, 1H), 7.93 (dt, J=8.7, 2.3 Hz, 1H), 6.91 (d, J=8.7 Hz, 1H), 5.02 (s, 1H), 4.52 (t, J=5.9 Hz, 2H), 4.24 (dd, J=11.9, 4.9 Hz, 2H), 3.78 (s, 3H), 3.60 (dd, J=12.9, 10.8 Hz, 2H), 3.13 (s, 2H), 2.77 (m, 8H), 2.38 (s, 2H), 1.98-1.91 (m, 2H).

Example 20

7-fluoro-3-methyl-8-(6-(3-(pyrrolidin-1-yl)propoxy)pyridin-3-yl)-1-(tetrahydro-2H-pyran-4-yl)-1H-imidazo[4,5-c]cinnolin-2(3H)-one

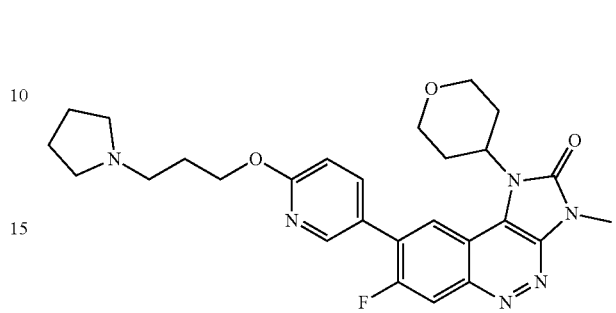

The title compound was prepared using similar procedure as in Example 18. MS: m/z 507 [M+H]$^+$. $^1$H NMR (400 MHz, CDCl$_3$) δ 8.44 (s, 1H), 8.27 (d, J=7.3 Hz, 1H), 8.18 (d, J=11.1 Hz, 1H), 7.97-7.90 (m, 1H), 6.91 (d, J=8.7 Hz, 1H), 5.02 (s, 1H), 4.51 (t, J=5.8 Hz, 2H), 4.24 (dd, J=11.8, 4.8 Hz, 2H), 3.78 (s, 3H), 3.60 (t, J=11.9 Hz, 2H), 3.28 (d, J=8.1 Hz, 2H), 2.80 (d, J=11.8 Hz, 2H), 2.52-2.44 (m, 2H), 2.18 (s, 4H), 1.95-1.80 (m, 6H).

Example 21

8-(6-(3-((dimethylamino)methyl)pyrrolidin-1-yl)pyridin-3-yl)-7-fluoro-3-methyl-1-(tetrahydro-2H-pyran-4-yl)-1H-imidazo[4,5-c]cinnolin-2(3H)-one

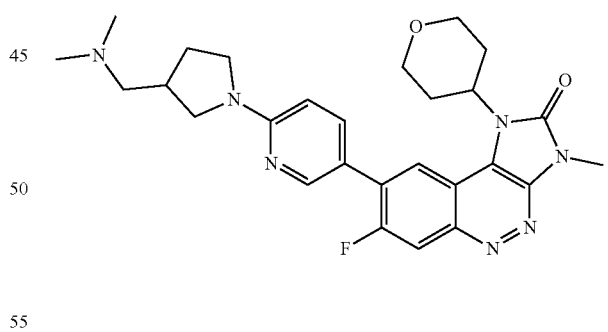

The title compound was prepared using similar procedure as in Example 18. MS: m/z 506 [M+H]$^+$. $^1$H NMR (400 MHz, CDCl$_3$) δ 8.49 (t, J=1.8 Hz, 1H), 8.19 (d, J=7.5 Hz, 1H), 8.11 (d, J=11.4 Hz, 1H), 7.80 (dt, J=8.9, 2.4 Hz, 1H), 6.54 (d, J=8.9 Hz, 1H), 4.99 (s, 1H), 4.24 (dd, J=11.8, 4.8 Hz, 2H), 3.76 (s, 5H), 3.63-3.50 (m, 3H), 3.27 (dd, J=10.4, 7.2 Hz, 1H), 2.83 (d, J=14.1 Hz, 2H), 2.61 (p, J=7.4 Hz, 1H), 2.46 (s, 1H), 2.35 (s, 6H), 2.29-2.18 (m, 1H), 1.94-1.89 (m, 2H), 1.85-1.80 (m, 2H).

Example 22

8-(6-(4-(dimethylamino)piperidin-1-yl)pyridin-3-yl)-7-fluoro-3-methyl-1-(tetrahydro-2H-pyran-4-yl)-1H-imidazo[4,5-c]cinnolin-2(3H)-one

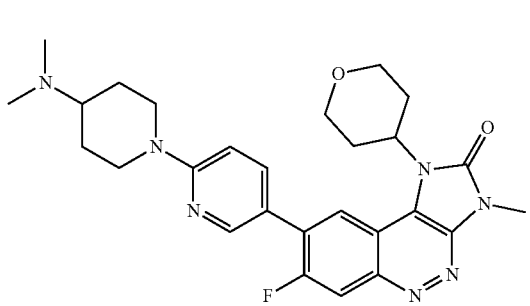

The title compound was prepared using similar procedure as in Example 18. MS: m/z 506 [M+H]⁺. ¹H NMR (400 MHz, CDCl₃) δ 8.51 (s, 1H), 8.24 (d, J=7.4 Hz, 1H), 8.14 (d, J=11.4 Hz, 1H), 7.86 (dt, J=8.9, 2.4 Hz, 1H), 6.83 (d, J=9.0 Hz, 1H), 5.04-5.01 (m, 1H), 4.64-4.61 (m, 2H), 4.27-4.23 (m, 2H), 3.77 (s, 3H), 4.64-3.58 (m, 2H), 3.12-3.08 (m, 1H), 3.01-2.95 (m, 2H), 2.83-2.80 (m, 2H), 2.67 (s, 6H), 2.27-2.23 (m, 2H), 1.95-1.92 (m, 2H), 1.78-1.74 (m, 2H).

Example 23

8-(6-((2-(dimethylamino)ethoxy)methyl)pyridin-3-yl)-7-fluoro-3-methyl-1-(tetrahydro-2H-pyran-4-yl)-1H-imidazo[4,5-c]cinnolin-2(3H)-one

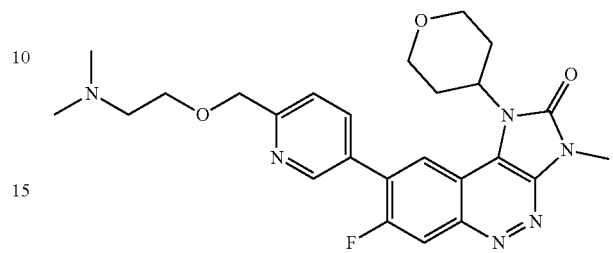

The title compound was prepared using similar procedure as in Example 18. MS: m/z 481[M+H]⁺. ¹H NMR (400 MHz, CDCl₃) δ 8.86 (s, 1H), 8.34 (d, J=7.3 Hz, 1H), 8.20 (d, J=11.1 Hz, 1H), 8.06 (s, 1H), 7.63 (s, 1H), 5.00 (s, 1H), 4.79 (s, 2H), 4.24-4.20 (m, 2H), 3.97 (t, J=5.3 Hz, 2H), 3.77 (s, 3H), 3.63-3.59 (m, 2H), 3.03 (t, J=5.2 Hz, 2H), 2.83-2.79 (d, J=14.0 Hz, 2H), 2.65 (s, 6H), 1.96-1.91 (m, 2H).

Example 24

7-fluoro-8-(6-(3-(4-fluoropiperidin-1-yl)propoxy)pyridin-3-yl)-3-methyl-1-(tetrahydro-2H-pyran-4-yl)-1H-imidazo[4,5-c]cinnolin-2(3H)-one Compound of Example 24 was prepared according to the synthetic route shown in Scheme 7:

Scheme 7

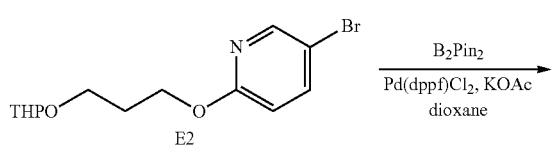

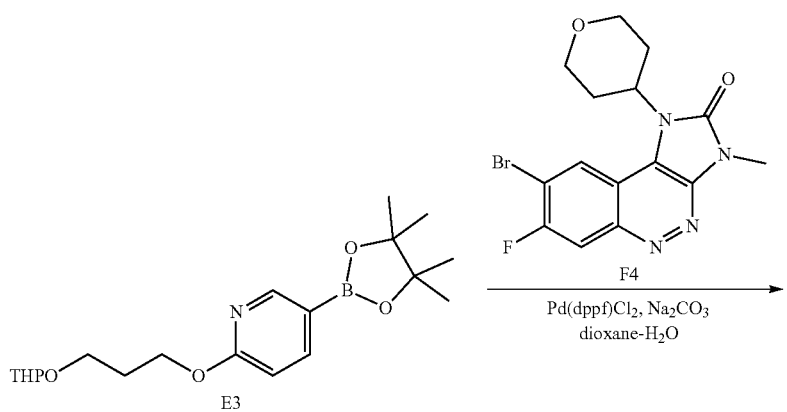

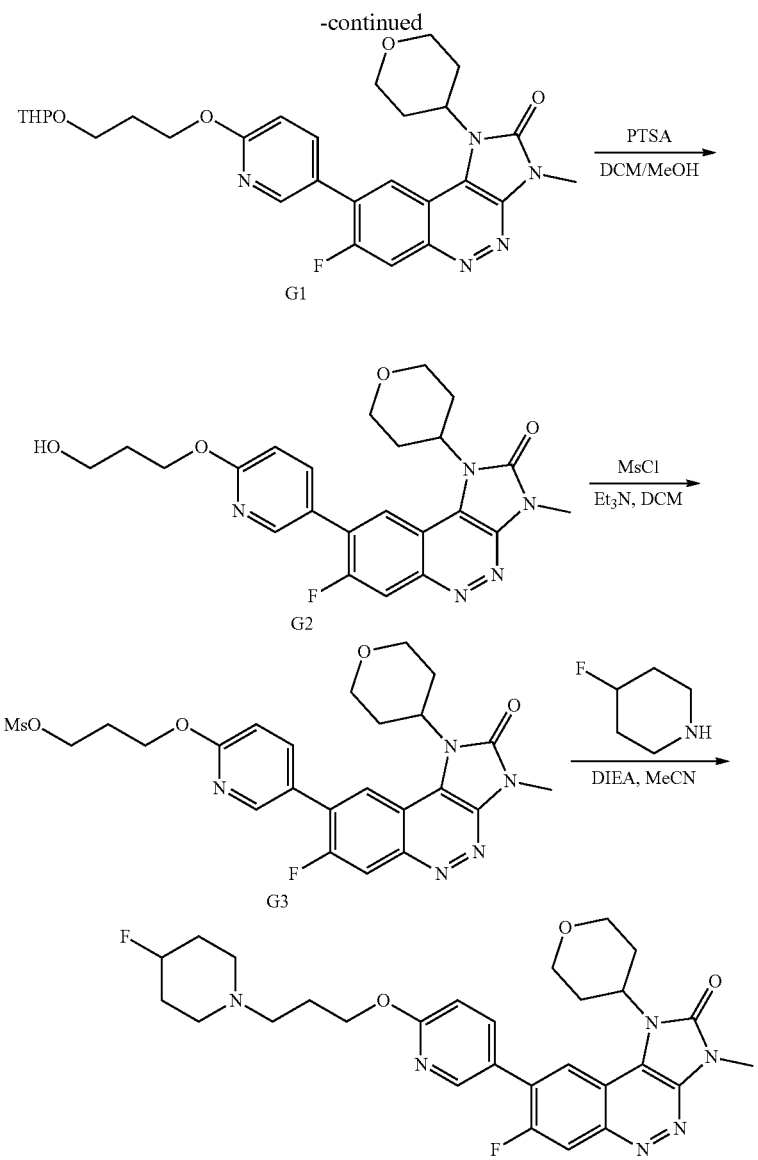

Step 1: 7-fluoro-3-methyl-8-(6-(3-((tetrahydro-2H-pyran-2-yl)oxy)propoxy)pyridin-3-yl)-1-(tetrahydro-2H-pyran-4-yl)-1H-imidazo[4,5-c]cinnolin-2(3H)-one (G1)

To a solution of 5-bromo-2-(3-((tetrahydro-2H-pyran-2-yl)oxy)propoxy)pyridine (200 mg, 0.635 mmol), $B_2Pin_2$ (194 mg, 0.76 mmol), and KOAc (187 mg, 1.9 mmol) in dioxane (5 mL) stirred at r.t. under nitrogen, was added $Pd(dppf)Cl_2 \cdot CH_2Cl_2$ (52 mg, 0.064 mol). The resulting mixture was stirred at 100° C. under $N_2$ for 16 hrs. After the reaction was cooled down, 8-bromo-7-fluoro-3-methyl-1-(tetrahydro-2H-pyran-4-yl)-1,3-dihydro-2H-imidazo[4,5-c]cinnolin-2-one (241 mg, 0.635 mmol), $Pd(dppf)Cl_2 \cdot CH_2Cl_2$ (52 mg, 0.064 mmol), $Na_2CO_3$ (200 mg, 1.9 mmol) and $H_2O$ (1 mL) were added. The resulting mixture was stirred at 100° C. under $N_2$ protection for another 4 hrs and concentrated to dryness. The residue was purified by column chromatography on silica gel to give the desired product (320 mg, 94% yield) as a dark solid. MS: 538 [M+H]⁺.

Step 2: 7-fluoro-8-(6-(3-hydroxypropoxy)pyridin-3-yl)-3-methyl-1-(tetrahydro-2H-pyran-4-yl)-1H-imidazo[4,5-c]cinnolin-2(3H)-one (G2)

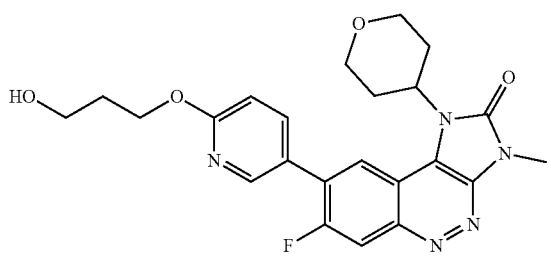 [SMILES: Cn1c(=O)n(C2CCOCC2)c2c3cc(-c4ccc(OCCCO)nc4)c(F)cc3nnc21]

To a solution of 7-fluoro-3-methyl-8-(6-(3-((tetrahydro-2H-pyran-2-yl)oxy)propoxy)pyridin-3-yl)-1-(tetrahydro-2H-pyran-4-yl)-1H-imidazo[4,5-c]cinnolin-2(3H)-one (360 mg, 0.67 mmol) in DCM/MeOH (3 mL/3 mL) stirred at r.t., was added PTSA (255 mg, 1.34 mmol). The resulting mixture was stirred at r.t. for 4 hrs and diluted with DCM (20 mL). The mixture was washed with aq. NaHCO$_3$, water and brine, dried over anhydrous Na$_2$SO$_4$, filtered and concentrated to give the desired product (220 mg, 72% yield), which was used for next step without further purification. MS: 454 [M+H]$^+$.

Step 3: 3-((5-(7-fluoro-3-methyl-2-oxo-1-(tetrahydro-2H-pyran-4-yl)-2,3-dihydro-1H-imidazo[4,5-c]cinnolin-8-yl)pyridin-2-yl)oxy)propyl methanesulfonate (G3)

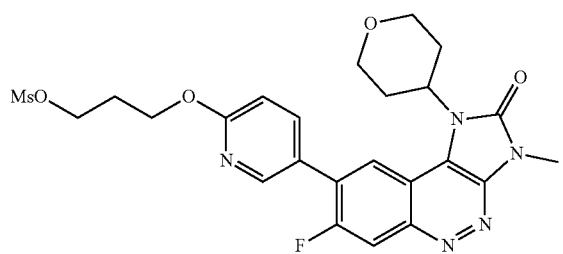 [SMILES: Cn1c(=O)n(C2CCOCC2)c2c3cc(-c4ccc(OCCCOS(C)(=O)=O)nc4)c(F)cc3nnc21]

To a solution of 7-fluoro-8-(6-(3-hydroxypropoxy)pyridin-3-yl)-3-methyl-1-(tetrahydro-2H-pyran-4-yl)-1H-imidazo[4,5-c]cinnolin-2(3H)-one (220 mg, 0.49 mmol) and Et$_3$N (150 mg, 1.47 mmol) in DCM (3 mL) was added MsCl (112 mg, 0.97 mmol) dropwise at 0° C. The resulting mixture was stirred at r.t. for 1 h and diluted with DCM (15 mL). The organic phase was washed with water and brine, dried over anhydrous Na$_2$SO$_4$, filtered and concentrated to give the crude product (340 mg, 100% yield), which was used for next step without further purification. MS: 532 [M+H]$^+$.

Step 4: 7-fluoro-8-(6-(3-(4-fluoropiperidin-1-yl)propoxy)pyridin-3-yl)-3-methyl-1-(tetrahydro-2H-pyran-4-yl)-1H-imidazo[4,5-c]cinnolin-2(3H)-one

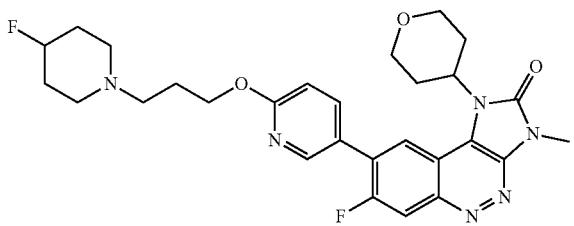 [SMILES: Cn1c(=O)n(C2CCOCC2)c2c3cc(-c4ccc(OCCCN5CCC(F)CC5)nc4)c(F)cc3nnc21]

To a solution of 3-((5-(7-fluoro-3-methyl-2-oxo-1-(tetrahydro-2H-pyran-4-yl)-2,3-dihydro-1H-imidazo[4,5-c]cinnolin-8-yl)pyridin-2-yl)oxy)propyl methanesulfonate (170 mg, 0.32 mmol) and DIEA (206 mg, 1.6 mmol) in MeCN (5 mL) stirred at r.t., was added 4-fluoropiperidine (180 mg, 1.28 mmol) in one portion. The resulting mixture was stirred at r.t. for 16 hrs and diluted DCM (20 mL). The organic phase was washed with water and brine, dried over anhydrous Na$_2$SO$_4$, filtered and concentrated. The residue was purified by prep-TLC to give the desired product (42 mg, 24% yield) as a yellow solid. MS: 539 [M+H]$^+$. $^1$H NMR (400 MHz, CD$_3$OD) δ 8.42 (d, J=7.6 Hz, 1H), 8.23 (d, J=2.5 Hz, 1H), 8.05 (d, J=11.6 Hz, 1H), 7.97 (dt, J=9.5, 2.4 Hz, 1H), 6.73 (d, J=9.4 Hz, 1H), 5.19-5.08 (m, 1H), 4.80-4.61 (m, 1H), 4.22-4.15 (m, 4H), 3.75-3.68 (m, 5H), 2.82-2.75 (m, 4H), 2.74-2.66 (m, 4H), 2.25-2.12 (m, 2H), 2.10-1.85 (m, 6H).

Example 25

(R)-7-fluoro-8-(6-(3-(3-fluoropyrrolidin-1-yl)propoxy)pyridin-3-yl)-3-methyl-1-(tetrahydro-2H-pyran-4-yl)-1H-imidazo[4,5-c]cinnolin-2(3H)-one

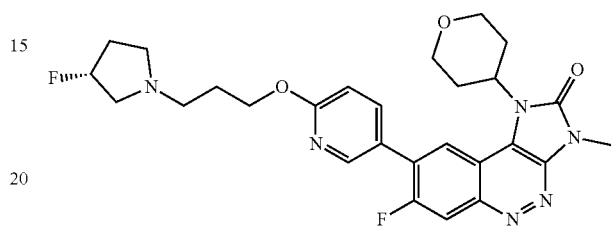

This material was synthesized from (R)-3-fluoropyrrolidine using similar procedure as in Example 24 to give the desired product (14% yield) as a yellow solid. MS: 525[M+H]$^+$. $^1$H NMR (400 MHz, CDCl$_3$) δ 8.30 (s, 1H), 8.14 (d, J=11.8 Hz, 1H), 7.98 (s, 1H), 7.74 (d, J=9.6 Hz, 1H), 6.72 (d, J=9.6 Hz, 1H), 5.21-5.07 (m, 2H), 4.29-4.14 (m, 4H), 3.78 (s, 3H), 3.63 (t, J=12.0 Hz, 2H), 2.98-2.89 (m, 2H), 2.78-2.62 (m, 4H), 2.18-1.87 (m, 8H).

Example 26

Biological Assays

The efficacy of the compounds of the present disclosure can be determined by a number of pharmacological assays known in the art. The exemplified pharmacological assays, which follow herein, were carried out with the compounds of the present disclosure as well as a control compound 8-[6-(3-dimethylamino-propoxy)-pyridin-3-yl]-3-methyl-1-(tetrahydro-2H-pyran-4-yl)-1H-imidazo[4,5-c]cinnolin-2 (3H)-one (Reference compound 1): a) ATM biochemical potency assay; b) PI3K biochemical potency assay; c) mTOR biochemical potency assay; d) ATR biochemical potency assay, and e) ATM SN-38 HT-29 cellular potency assay. During the description of the assays, generally:

i. The following abbreviations have been used: 4NQO=4-Nitroquinoline N-oxide; Ab=Antibody; BSA=Bovine Serum Albumin; CO$_2$=Carbon Dioxide; DMEM=Dulbecco's Modified Eagle Medium; DMSO=Dimethyl Sulphoxide; EDTA=Ethylenediaminetetraacetic Acid; EGTA=Ethylene Glycol Tetraacetic Acid; ELISA=Enzyme-linked Immunosorbent Assay; EMEM=Eagle's Minimal Essential Medium; FBS=Foetal Bovine Serum; h=Hour(s); HRP=Horseradish Peroxidase; i.p.=intraperitoneal; PBS=Phosphate buffered saline; PBST=Phosphate buffered saline/Tween; TRIS=Tris(Hydroxymethyl) aminomethane; MTS reagent: [3-(4,5-dimethylthiazol-2-yl)-5-(3-carboxymethoxyphenyl)-2-(4-sulfophenyl)-2H-tetrazolium, inner salt, and an electron coupling reagent (phenazine methosulfate) PMS; s.c.=subcutaneously.

ii. IC$_{50}$ values were calculated using a smart fitting model in Genedata. The IC$_{50}$ value was the concentration of test compound that inhibited 50% of biological activity.

Assay a): ATM Biochemical Potency

ATM (Millipore, Cat. No. 14-933) enzyme solution was prepared in 1× kinase base buffer. 10 µl of 2× enzyme solution was transferred to each well of the 384-well assay plate containing 100 nl compounds added by Echo. The plate was incubated at room temperature for 10 minutes. 2× peptide solution was prepared with FAM-labeled peptide and ATP in the 1× kinase base buffer (final concentration: 1.5 nM). 10 µl of 2× peptide solution was added to each well of the 384-well assay plate which was incubated at 37° C. for 210 min before 40 µl stop buffer was added to stop reaction. Data was collected by Caliper.

Assay b): ATR Biochemical Potency

ATR enzyme was made by ChemPartner (batch: CP-ATR-20161102-M2). 2× enzyme solutions were prepared in 1× kinase base buffer. 10 µl of 2× enzyme solution (final concentration: 2.5 nM) was added to each well of the 384-well assay plate containing 60 nl compound in each well. The plate was incubated at room temperature for 10 minutes. 2× peptide solutions were prepared with FAM-labeled peptide and ATP in the 1× kinase base buffer. 10 µl of 2× peptide solution was added to each well of the 384-well assay plate, which was incubated at 28° C. for 240 min. 40 µl of stop buffer was added to stop reaction. Data were collected by Caliper.

Assay c): PI3K Biochemical Potency

PI3Kα (p110α/p85a), PIK3C δ, PIK3Cβ (p110β), PIK3Cγ (pp110γ) kinase reaction solutions of PI3Kα (Invitrogen, Cat. No. PV4788), PIK3Cδ (Invitrogen, Cat. No. PV6452), PIK3Cβ (Millipore, Cat. No. 14-603-K), PIK3Cγ (Invitrogen, Cat. No. PR8641C) enzymes were prepared in 1× kinase buffer at 4-fold of the final concentration (final concentration: PI3Kα 0.7 nM, PIK3Cδ 3 nM, PIK3Cβ 4.8 nM, PIK3Cγ 11 nM) of each reagent in the assay. 2.5 µl of kinase solution was added to each well of the 384-well assay plate, which contains 2.5 µl of compounds with serially diluted concentration. 2× substrate solution was prepared with PIP2 substrate and ATP in 1× kinase reaction buffer at 2-fold of the final concentration of each reagent in the assay. 5 µl of substrate solution was added to each well of the assay plate to start reaction. The assay plate was incubated at room temperature for 1 hour. 5 µl reaction mix was transferred to a new 384 well plate. 5 µl of ADP-Glo reagent (Promega, Cat. No. v9102/3, Lot. No. 0000176563) was added to each well of the new assay plate to stop the reaction. The plate was shaken slowly and equilibrated for 40 minutes. 10 µl kinase detection reagents was added to each well, which was equilibrated for 60 minutes before read on a plate reader (Envision) for luminescence.

Assay d): mTOR Biochemical Potency

Solution of mTOR enzymes (Millipore, Cat. No. 14-770, Lot. No. 2052551) was prepared in 1× kinase buffer at 4-fold of the final concentration (final concentration: 6 nM) in the assay. 2.5 µl of kinase solution was added to each well of the 384-well assay plate, which contains 2.5 µl of compounds with serially diluted concentration. 2× substrate solution was prepared with ULight-4E-BP1 (Thr37/46) Peptide (PE, Cat. No. TRF0128-M, Lot. No. 1695274) and ATP in 1× kinase reaction buffer at 2-fold of the final concentration of each reagent in the assay. 5 µl of substrate solution was added to each well of the assay plate to start reaction. The assay plate was incubated at room temperature for 30 minutes. Detection solution of kinase quench buffer (EDTA) and Eu-anti-phospho-4E-BP1 antibody (Thr37/46) (PE, Cat. No. TRF0216-M, Lot. No. 1571838) were prepared at 2-fold the desired final concentrations of each reagent in Lance detection buffer. 10 µl of detection solution buffer was added to each well of the assay plate. The assay plate was equilibrated for 60 minutes at room temperature before read on a plate reader (Lance signal (665 nm) from Envision program).

Assay e): ATM SN-38 BT-29 Cellular Potency

Rationale:

SN38 is an active metabolite of irinotecan, a topoisomerase-I inhibitor. SN38 causes single strand DNA breaks (SSBs) which are converted to double strand breaks (DSBs) during replication. ATM plays role of repairing DSBs. Inhibition of ATM was evaluated in SN38 treated HT-29 cells (ATCC, Cat #HTB-38) by high-Content Imaging System Experimental Details HT-29 cells were trypsinized and approximately 10,000 cells were seeded per well to 96-well microplates which were incubated overnight at 37° C. and 5% CO$_2$. Test compounds were added to the 96-well plates which were incubated at 37° C. and 5% CO$_2$ for 1 hour. SN38 (MCE, Cat #HY-13704) at final concentration of 30 nM was then added to the 96-well plates, which were incubated at 37° C. and 5% CO$_2$ for 1 hour. After medium removal, cells were fixed by the addition of 50 µl 3.7% formaldehyde in PBSA and incubated for 20 minutes at room temperature. After the plates were rinsed 3 times with PBSA, 50 µl permeabilization buffer (0.1% Triton-X 100 in PBSA) was added and the plates were incubated for 20 minutes at room temperature. After the plates were rinsed once with PBSA, 50 µl primary antibody solution was added and the plates were incubated in at 4° C. overnight. The primary antibody solution was prepared by diluting primary antibody (anti-phospho-ATM (Ser1981) antibody, (Merck Millipore, Cat #05-740) at 1/10,000th in antibody buffer (3% BSA, 0.05% Tween in PBSA). The plates were rinsed 3 times with PBST (0.05% Tween in PBSA). 50 µl secondary antibody solution was added to the plates which were incubated at room temperature for 1 hour away from light. The secondary antibody solution was prepared by diluting secondary antibody (Goat anti-Mouse IgG (H+L) Cross-Adsorbed Secondary Antibody, Alexa Fluor 488, Invitrogen, Cat #A11001) at 1/500th and Hoechst at 1/10,000th in antibody buffer. The plates were rinsed with PBST 3 times and then 100 µl PBSA were added per well. The plates were sealed with black plate seals.

| Data Capture | |
| --- | --- |
| Instrument | High-Content Imaging System, ImageXpress (Molecular Devices) |
| Software | ImageXpress (5.1.0.3) |
| Plate | 96-well cell culture plate, µ clear - Grenier - 655090 |
| Objective | 10X |
| Well | 9 sites/well |
| | 300 µM between images in X direction and 300 µM in Y direction |
| Wavelength | 2 Wavelengths — W1 DAPI (Nuclei) Auto Exposure; W2 FITC (pATM) Auto Exposure |
| Focus | Focusing each well — Autofocus at each site in well |

| Data Analysis | |
| --- | --- |
| Software | MetaXpress (5.1.0.41) |
| Module | Cell Scoring |

-continued

| Data Analysis | |
|---|---|
| Parameters | Measures positive cells in assay with a nuclear stain and a probe of interest "Cell Number" & "Positive Cells Area" |

After image analysis, further statistics were done by Excel 2013 (Microsoft). The graphical views were then generated using Prism 7.0 (Graphpad).

The compounds synthesized in Examples 1-45 and Reference compound 1 were tested in Assays a)-e) as described above. The $IC_{50}$ results are provided in Table 2 for some representative compounds. From Table 2, it can be found that the compounds of the present disclosure not only have very good inhibition of ATM kinase, they are also very selective for ATM kinase over other kinases (PI3Kα, PI3Kβ, PI3Kγ, PI3Kδ, mTor and ATR) in PIKK family. For the other Example compounds for which the results are not shown, all have an $IC_{50}$ against ATM kinase of no more than 1000 nM. Some of these compounds have an $IC_{50}$ against ATM kinase of no more than 500 nM, some no more than 400 nM, some no more than 300 nM, some no more than 200 nM, or no more than 100 nM, or even no more than 50 nM. In addition, some of the Example compounds for which the results are not shown show $IC_{50}$ against other kinases (PI3Kα, PI3Kβ, PI3Kγ, PI3Kδ, mTor and ATR) in PIKK family of more than 1 μM, some more than 3 μM, more than 5 μM, more than 7 μM, or even more than 10 μM.

TABLE 2

Potency Data for representative compounds in Assays a)-e)

| Example | ATM $IC_{50}$ (nM) | ATR $IC_{50}$ (μM) | PI3Kα $IC_{50}$ (μM) | PI3Kβ $IC_{50}$ (μM) | PI3Kγ $IC_{50}$ (μM) | PI3Kδ $IC_{50}$ (μM) | mTor $IC_{50}$ (μM) | SN-38 HT-29 cellular $IC_{50}$ (nM) |
|---|---|---|---|---|---|---|---|---|
| 1 | 1.9 | >10 | >10 | >10 | >10 | >10 | >10 | 1.5 |
| 2 | 4.3 | >10 | >10 | >10 | >10 | >10 | >10 | 270 |
| 3 | 4.8 | >10 | >10 | >10 | >10 | >10 | >10 | 11 |
| 4 | 10 | >10 | >10 | >10 | >10 | >10 | >10 | |
| 5 | 65 | >10 | >10 | >10 | >10 | >10 | >10 | |
| 6 | 100 | >10 | >10 | >10 | >10 | >10 | >10 | 71 |
| 7 | 26 | >10 | >10 | >10 | >10 | >10 | >10 | 274 |
| 8 | 51 | >10 | >10 | >10 | >10 | >10 | >10 | |
| 9 | 35 | >10 | >10 | >10 | >10 | >10 | >10 | |
| 10 | 25 | >10 | >10 | >10 | >10 | >10 | >10 | 273 |
| 11 | 37 | >10 | >10 | >10 | >10 | >10 | >10 | 18 |
| 12 | 363 | >10 | >10 | >10 | >10 | >10 | >10 | |
| 13 | >1000 | >10 | >10 | >10 | >10 | >10 | >10 | 27 |
| 14 | >1000 | >10 | >10 | >10 | >10 | >10 | >10 | |
| 15 | >1000 | >10 | >10 | >10 | >10 | >10 | >10 | 15 |
| 16 | >1000 | >10 | >10 | >10 | >10 | >10 | >10 | 18.5 |
| 17 | 7 | | | | | | | |
| 18 | 4.8 | | | | | | | |
| 19 | 13 | | | | | | | |
| 20 | 6 | | | | | | | |
| 21 | 97 | | | | | | | |
| 24 | >1000 | | | | | | | |
| 25 | >1000 | | | | | | | |
| Ref. Comp. 1 | 2.9 | | | | | | | 112 |

Example 27

DMPK and hERG Inhibition Studies

DMPK and hERG inhibition studies were carried out with the compounds of the present disclosure as well as Reference compound 1, Reference compound 2 (AZD0156) and Reference compound 3 (AZD1390) using the following assays: f): MDCK-MDR1 Pgp assessment, g) Caco-2 BCRP assessment, and h) hERG inhibition assessment.

Assay f): MDCK-MDR1 Pgp Assessment

Efflux transport mediated by P-glycoprotein (Pgp) was assessed by MDCK-MDR1 cells. The final concentrations of test compounds and control compound were at 1 μM. The multiwell insert plate was incubated at 37° C. for 2 hours.

Assay g): Caco-2 BCRP Assessment

Caco-2 cells was used to study efflux transport mediated by BCRP. Rate of drug transport by BCRP was determined in the presence and absence of novobiocin, a strong inhibitor of BCRP, which was added to both apical and basolateral compartments at a final concentration of 30 μM. The final concentrations of test compounds and control compound were at 1 μM. The multiwell insert plate was incubated at 37° C. for 2 hours. Efflux ratio (−inhibitor/+inhibitor)>2 was considered to be a BCRP substrate.

Assay h): hERG Safety Assessment

Inhibition of hERG channel was conducted in HEK 293 cell line stably expressing hERG channel by manual patch clamp.

Results of some representative compounds of the present disclosure and Reference compounds 1-3 in assay f), g), and h) are shown in Table 3.

TABLE 3

Results of representative compounds and Reference compounds 1-3 in assay f)-h)

| | Ex. 1 | Ex. 3 | Ex. 4 | Ex. 5 | Ref. Comp. 1 | Ref. Comp. 2 | Ref. Comp. 3 |
|---|---|---|---|---|---|---|---|
| MDCK-MDR1 efflux ratio (ER) | 2.3 | 1.4 | 1.4 | 1.4 | 5.6 | 7.2 | 1.7 |
| Caco-2 BCRP efflux ratio | 0.91 | 0.71 | <1 | <1 | 0.62 | N/A | 0.89 |
| hERG inhibition @10 μM | 57% | 41% | N/A* | N/A | 58% | 25% | 79% |

*Not available.

From Table 3, it is demonstrated that Reference compound 2 turned out to be a Pgp substrate. Reference compound 3 is not a Pgp substrate, however, it shows significant hERG inhibition. By comparison, representative compounds of Examples 1 and 3-5 are not Pgp substrate and BCRP substrates, indicating that they are brain penetratable. Furthermore, compounds of Examples 1 and 3 show significant improvement of hERG liability compared to Reference compound 3.

For the other Example compounds for which the results are not shown, all show similar DMPK and hERG results as the exemplary compounds of Examples 1 and 3-5.

Example 28

AO Activity Study

AO activity study was carried out with the compounds of the present disclosure and Reference compounds 2, 3, 4 (Zaleplon, an AO assay positive control) and 5 (PF-04217903, a weak AO substrate) using the following assay i) Aldehyde oxidase assay.

Assay i): Aldehyde Oxidase Assay

AO activity was assessed in human liver cytosol. The incubation system was composed of 25 mM phosphate buffer, 1 mg/mL human liver cytosol and 0.5 µM of test compounds or positive controls. The reaction was stopped at 0.5, 5, 10, 20, 30 and 60 minutes by the addition of 5 volumes of cold acetonitrile with internal standard. Samples were centrifuged at 3,220 g for 30 minutes. Aliquot of 100 µL of the supernatant was mixed with 100 µL of ultra-pure H₂O and then used for LC/MS/MS analysis.

All calculations were carried out using Microsoft Excel. Peak areas were determined from extracted ion chromatograms. The slope value, k, was determined by linear regression of the natural logarithm of the remaining percentage of the parent drug vs. incubation time curve. The in vitro half-life (in vitro $t_{1/2}$) was determined from the slope value using the following equation:

$$\text{in vitro } t_{1/2} = -(0.693/k)$$

Conversion of the in vitro $t_{1/2}$ (min) into the in vitro intrinsic clearance (in vitro $CL_{int}$, in µL/min/mg protein) was done using the following equation (mean of duplicate):

$$\text{in vitro } CL_{int} = \left(\frac{0.693}{(t_{1/2})}\right) + \left(\frac{\text{volume of incubation } (\mu L)}{\text{amount of proteins (mg)}}\right).$$

The compounds synthesized in Examples 1-25 and Reference compounds 2-4 were tested in Assay i) as described above. Results of representative compounds of the present disclosure and Reference compounds 2-5 are shown in Table 4.

TABLE 4

Results of representative compounds and Reference compounds 2-5 in assay i)

| Example | AO intrinsic clearance (µL/min/mg protein) |
| --- | --- |
| 1 | 0.84 |
| 3 | 0.29 |
| 4 | <1 |
| 5 | <1 |
| 6 | 1.0 |
| 7 | 0.0 |
| 8 | 0.36 |
| 9 | 1.2 |
| 10 | 1.0 |
| 11 | 0.82 |
| 13 | 0.96 |
| 15 | 0.0 |
| 23 | 0.9 |
| Ref. Comp. 2 | 4.65 |
| Ref. Comp. 3 | 7.2 |
| Ref. Comp. 4 | 3.1 |
| Ref. Comp. 5 | 1.8 |

It is demonstrated Reference compounds 2 and 3 are shown to be strong AO substrates with intrinsic clearance of 4.65 and 7.2 µL/min/mg protein, higher than that of Reference compound 4 (3.1 µL/min/mg protein). Reference compound 4 showed high clearance in humans at 16 mL/min/kg corresponding to ~80% liver blood flow (Zientek, M. et al, Drug Metab Dispos 2010, 1322-7). In contrast, the compounds of the present disclosure show an intrinsic clearance lower than that of Reference compound 5 (1.8 µL/min/mg protein). Reference compound 5 showed low to moderate clearance in humans at 6 mL/min/kg corresponding to ~30% liver blood flow. This indicates that the compounds of the present disclosure are not AO substrates.

For the other Example compounds for which the results are not shown, all show intrinsic clearance of no more than 2 µL/min/mg protein, no more than 1.8 µL/min/mg protein, no more than 1.6 µL/min/mg protein, no more than 1.4 µL/min/mg protein, no more than 1.2 µL/min/mg protein, no more than 1 µL/min/mg protein, no more than 0.9 µL/min/mg protein, no more than 0.8 µL/min/mg protein, no more than 0.7 µL/min/mg protein, no more than 0.6 µL/min/mg protein, or even no more than 0.5 µL/min/mg protein.

The foregoing description is considered as illustrative only of the principles of the present disclosure. Further, since numerous modifications and changes will be readily apparent to those skilled in the art, it is not desired to limit the invention to the exact construction and process shown as described above. Accordingly, all suitable modifications and equivalents maybe considered to fall within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:

1. A compound of formula (I):

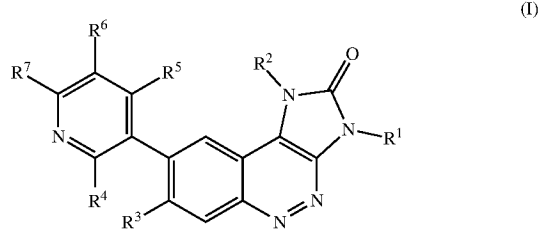

or a pharmaceutically acceptable salt thereof,
wherein:
$R^1$ is hydrogen or methyl;
$R^2$ is isopropyl or tetrahydropyranyl;
$R^3$ is hydrogen or fluoro;
$R^4$, $R^5$ and $R^6$ are each independently selected from hydrogen or fluoro;
$R^7$ is -L-NR$^8$R$^9$, wherein L is selected from —(CH$_2$)$_m$O(CH$_2$)$_n$— or —CONR$^{10}$(CH$_2$)$_p$—, wherein said —(CH$_2$)$_m$O(CH$_2$)$_n$— and —CONR$^{10}$(CH$_2$)$_p$— are optionally substituted by one or more $R^{11}$;
$R^8$ and $R^9$ are each independently selected from the group consisting of hydrogen, alkyl, alkenyl, alkynyl, saturated or unsaturated cycloalkyl, and saturated or unsaturated heterocyclyl, wherein said alkyl, alkenyl, alkynyl, saturated or unsaturated cycloalkyl, and saturated or unsaturated heterocyclyl are optionally substituted with one or more $R^{12}$; or
$R^8$ and $R^9$ together with the nitrogen atom to which they are attached form a saturated or unsaturated heterocyclyl optionally containing one or more additional heteroatoms selected from N, O and S and optionally substituted with one or more $R^{13}$;
$R^{10}$ is selected from the group consisting of hydrogen, alkyl, cycloalkyl, and saturated or unsaturated heterocyclyl which is carbon linked, wherein said heterocyclyl optionally contains one or more additional heteroatoms selected from N, O and S and is optionally substituted with one or more $R^{13}$;
$R^{11}$ is selected from the group consisting of hydrogen, halogen, alkyl, cycloalkyl, alkoxyl, and saturated or unsaturated heterocyclyl optionally containing one or more additional heteroatoms selected from N, O and S and optionally substituted with one or more $R^{13}$;

$R^{12}$ is selected from the group consisting of hydrogen, halogen, cyano, nitro, hydroxyl, alkyl, alkenyl, alkynyl, and alkoxy;

$R^{13}$ is selected from the group consisting of acyl, alkyl, alkenyl, alkynyl, alkoxy, amide, amino, aryl, cyano, cycloalkyl, halogen, haloalkyl, haloalkoxy, heteroaryl, hydroxy, nitro, and $-(CH_2)_qNR^{14}R^{15}$;

$R^{14}$ and $R^{15}$ are each independently selected from the group consisting of hydrogen, alkyl, and cycloalkyl; or $R^{14}$ and $R^{15}$ together with the nitrogen atom to which they are attached form a saturated or unsaturated heterocyclyl optionally containing one or more additional heteroatoms selected from N, O and S and optionally substituted with one or more $R^{16}$;

$R^{16}$ is selected from the group consisting of acyl, alkyl, alkenyl, alkynyl, alkoxy, amide, amino, aryl, cyano, cycloalkyl, halogen, haloalkyl, haloalkoxy, heteroaryl, hydroxy, and nitro;

m is 1 or 2;

n is an integer in the range of 2 to 4;

p is an integer in the range of 2 to 4; and q is 0, 1 or 2.

2. The compound of Formula (I) or a pharmaceutically acceptable salt thereof, as claimed in claim 1, wherein $R^1$ is methyl.

3. The compound of Formula (I) or a pharmaceutically acceptable salt thereof, as claimed in claim 1, wherein $R^2$ is isopropyl.

4. The compound of Formula (I) or a pharmaceutically acceptable salt thereof, as claimed in claim 1, wherein $R^3$ is fluoro.

5. The compound of Formula (I) or a pharmaceutically acceptable salt thereof, as claimed in claim 1, wherein $R^4$, $R^5$ and $R^6$ are hydrogen.

6. The compound of Formula (I) or a pharmaceutically acceptable salt thereof, as claimed in claim 1, wherein $R^7$ is -L-$NR^8R^9$ and L is $-CONR^{10}(CH_2)_p-$, $R^8$ and $R^9$ are each independently selected from $C_{1-6}$ alkyl optionally substituted with one or more $R^{12}$, and $R^{10}$ is hydrogen.

7. The compound of Formula (I) or a pharmaceutically acceptable salt thereof, as claimed in claim 1, wherein:

$R^1$ is methyl;

$R^2$ is isopropyl or tetrahydropyranyl;

$R^3$ is hydrogen or fluoro;

$R^4$, $R^5$ and $R^6$ are hydrogen;

$R^7$ is -L-$NR^8R^9$ and

L is $-(CH_2)_mO(CH_2)_n-$ optionally substituted by one or more $R^{11}$;

$R^8$ and $R^9$ are each independently selected from $C_{1-6}$ alkyl optionally substituted with one or more $R^{12}$; or $R^8$ and $R^9$ together with the nitrogen atom to which they are attached form

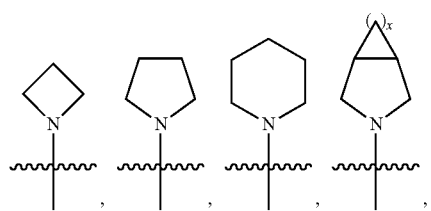

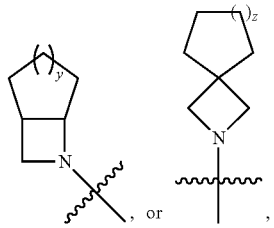

each of which is optionally substituted with one or more $R^{13}$, wherein x is 1, 2, 3 or 4; y is 0, 1 or 2; and z is 0, 1 or 2;

$R^{11}$ is methyl or ethyl;

$R^{12}$ is hydrogen;

$R^{13}$ is halogen;

m is 1 or 2;

n is an integer in the range of 2 to 4.

8. The compound of Formula (I) or a pharmaceutically acceptable salt thereof, as claimed in claim 1, wherein the compound is selected from the group consisting of:

8-(6-((2-(dimethylamino)ethoxy)methyl)pyridin-3-yl)-7-fluoro-1-isopropyl-3-methyl-1,3-dihydro-2H-imidazo[4,5-c]cinnolin-2-one;

7-fluoro-1-isopropyl-3-methyl-8-(6-((2-(piperidin-1-yl)ethoxy)methyl)pyridin-3-yl)-1,3-dihydro-2H-imidazo[4,5-c]cinnolin-2-one;

7-fluoro-1-isopropyl-3-methyl-8-(6-((2-(pyrrolidin-1-yl)ethoxy)methyl)pyridin-3-yl)-1,3-dihydro-2H-imidazo[4,5-c]cinnolin-2-one;

(R)-7-fluoro-8-(6-((2-(3-fluoropyrrolidin-1-yl)ethoxy)methyl)pyridin-3-yl)-1-isopropyl-3-methyl-1,3-dihydro-2H-imidazo[4,5-c]cinnolin-2-one;

7-fluoro-8-(6-((2-(4-fluoropiperidin-1-yl)ethoxy)methyl)pyridin-3-yl)-1-isopropyl-3-methyl-1,3-dihydro-2H-imidazo[4,5-c]cinnolin-2-one;

8-(6-((2-(3-azabicyclo[3.1.0]hexan-3-yl)ethoxy)methyl)pyridin-3-yl)-7-fluoro-1-isopropyl-3-methyl-1,3-dihydro-2H-imidazo[4,5-c]cinnolin-2-one;

N-(2-(dimethylamino)ethyl)-5-(7-fluoro-1-isopropyl-3-methyl-2-oxo-2,3-dihydro-1H-imidazo[4,5-c]cinnolin-8-yl) picolinamide;

8-(6-((2-(dimethylamino)ethoxy)methyl)pyridin-3-yl)-7-fluoro-3-methyl-1-(tetrahydro-2H-pyran-4-yl)-1,3-dihydro-2H-imidazo[4,5-c]cinnolin-2-one;

8-(6-((2-(diethylamino)ethoxy)methyl)pyridin-3-yl)-7-fluoro-1-isopropyl-3-methyl-1,3-dihydro-2H-imidazo[4,5-c]cinnolin-2-one;

8-(6-((2-(ethyl(methyl)amino)ethoxy)methyl)pyridin-3-yl)-7-fluoro-1-isopropyl-3-methyl-1,3-dihydro-2H-imidazo[4,5-c]cinnolin-2-one;

7-fluoro-1-isopropyl-3-methyl-8-(6-((2-morpholinoethoxy)methyl)pyridin-3-yl)-1,3-dihydro-2H-imidazo[4,5-c]cinnolin-2-one;

7-fluoro-1-isopropyl-3-methyl-8-(6-((2-(piperazin-1-yl)ethoxy)methyl)pyridin-3-yl)-1,3-dihydro-2H-imidazo[4,5-c]cinnolin-2-one;

7-fluoro-1-isopropyl-3-methyl-8-(6-((2-(4-methylpiperazin-1-yl)ethoxy)methyl)pyridin-3-yl)-1,3-dihydro-2H-imidazo[4,5-c]cinnolin-2-one;

8-(6-((2-(4-cyclopropylpiperazin-1-yl)ethoxy)methyl) pyridin-3-yl)-7-fluoro-1-isopropyl-3-methyl-1,3-dihydro-2H-imidazo[4,5-c]cinnolin-2-one;

8-(6-((2-(2-azaspiro[3.3]heptan-2-yl)ethoxy)methyl)pyridin-3-yl)-7-fluoro-1-isopropyl-3-methyl-1,3-dihydro-2H-imidazo[4,5-c]cinnolin-2-one;

8-(6-((2-(2-oxa-6-azaspiro[3.3]heptan-6-yl)ethoxy) methyl)pyridin-3-yl)-7-fluoro-1-isopropyl-3-methyl-1, 3-dihydro-2H-imidazo[4,5-c]cinnolin-2-one;

8-(6-((2-(2-azaspiro[3.4]octan-2-yl)ethoxy)methyl)pyridin-3-yl)-7-fluoro-1-isopropyl-3-methyl-1,3-dihydro-2H-imidazo[4,5-c]cinnolin-2-one;

8-(6-((2-(6-azabicyclo[3.2.0]heptan-6-yl)ethoxy)methyl) pyridin-3-yl)-7-fluoro-1-isopropyl-3-methyl-1,3-dihydro-2H-imidazo[4,5-c]cinnolin-2-one.

9. The compound of Formula (I) or a pharmaceutically acceptable salt thereof, as claimed in claim 1, wherein the compound has an AO intrinsic clearance value of less than 1.8 µL/min/mg protein in human liver cytosol system.

10. A pharmaceutical composition comprising a compound of Formula (I) or a pharmaceutically acceptable salt thereof, as claimed in claim 1, and at least one pharmaceutically acceptable excipient.

11. The compound of Formula (I) or a pharmaceutically acceptable salt thereof, as claimed in claim 1, wherein $R^7$ is -L-$NR^8R^9$ and L is —$(CH_2)_mO(CH_2)_n$— optionally substituted by one or more $R^{11}$, wherein m is 1 or 2, n is an integer in the range of 2 to 4, wherein $R^{11}$ is selected from the group consisting of hydrogen, halogen, alkyl, cycloalkyl, alkoxyl, and saturated or unsaturated heterocyclyl.

12. The compound of Formula (I) or a pharmaceutically acceptable salt thereof, as claimed in claim 11, wherein $R^8$ and $R^9$ are independently selected from methyl, ethyl, propyl, or butyl; or $R^8$ and $R^9$ together with the nitrogen atom to which they are attached form:

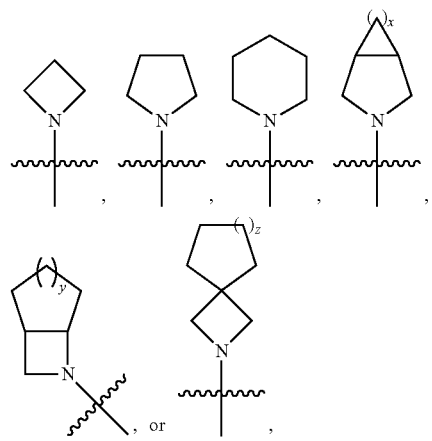

each of which is optionally substituted with one or more $R^{13}$, wherein x is 1, 2, 3 or 4; y is 0, 1 or 2; and z is 0, 1 or 2.

13. The compound of Formula (I) or a pharmaceutically acceptable salt thereof, as claimed in claim 11, wherein $R^{11}$ is hydrogen, halogen, methyl, ethyl, isopropyl, cyclopropyl and cyclobutyl.

14. The compound of Formula (I) or a pharmaceutically acceptable salt thereof, as claimed in claim 11, wherein m is 1.

15. The compound of Formula (I) or a pharmaceutically acceptable salt thereof, as claimed in claim 11, wherein n is 2.

16. The compound of Formula (I) or a pharmaceutically acceptable salt thereof, as claimed in claim 11, wherein m is 1 and n is 2.

* * * * *